United States Patent
Neidlein et al.

(10) Patent No.: US 6,713,436 B1
(45) Date of Patent: Mar. 30, 2004

(54) 1-CYCLOALKYLPYRAZOLYL-BENZOYL DERIVATIVES

(75) Inventors: Ulf Neidlein, Mannheim (DE); Norbert Götz, Worms (DE); Ulf Misslitz, Neustadt (DE); Roland Götz, Neulussheim (DE); Ernst Baumann, Dudenhofen (DE); Wolfgang von Deyn, Neustadt (DE); Steffen Kudis, Mannheim (DE); Klaus Langemann, Worms (DE); Guido Mayer, Neustadt (DE); Matthias Witschel, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/048,949

(22) PCT Filed: Dec. 1, 1999

(86) PCT No.: PCT/EP99/09342

§ 371 (c)(1),
(2), (4) Date: Feb. 6, 2002

(87) PCT Pub. No.: WO01/10864

PCT Pub. Date: Feb. 15, 2001

(30) Foreign Application Priority Data

Aug. 6, 1999 (DE) .......................... 199 36 518

(51) Int. Cl.⁷ ............... A01N 43/80; C07D 413/10
(52) U.S. Cl. ................... 504/271; 548/247
(58) Field of Search ............... 504/271; 548/240

(56) References Cited

U.S. PATENT DOCUMENTS 5,846,907 A    12/1998   Von Deyn et al.

FOREIGN PATENT DOCUMENTS

| CA | 2277893 | 7/1998 |
|----|---------|--------|
| CA | 2278331 | 7/1998 |
| EP | 1 031 573 | 8/2000 |
| WO | 96/26206 | 8/1996 |
| WO | 98/42678 | 10/1998 |
| WO | 98/52926 | 11/1998 |

*Primary Examiner*—Alan L. Rotman
*Assistant Examiner*—Sonya Wright
(74) *Attorney, Agent, or Firm*—Keil & Weinkauf

(57) ABSTRACT

The present invention relates to 1-cycloalkylpyrazolylbenzoyl derivatives of the formula I

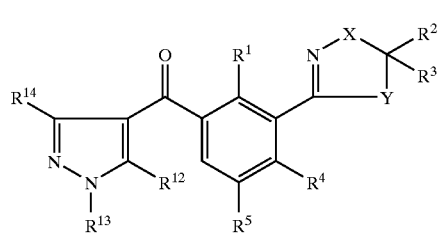

wherein all variables are as defined in the specification, their agriculturally useful salts, processes for their preparation, and for the use of these compounds or compositions comprising them, for controlling undesirable plants.

7 Claims, No Drawings

1-CYCLOALKYLPYRAZOLYL-BENZOYL DERIVATIVES

This application is a 371 of PCT/EP99/09342 filed Dec. 1, 1999.

The present invention relates to 1-cycloalkylpyrazolylbenzoyl derivatives of the formula I

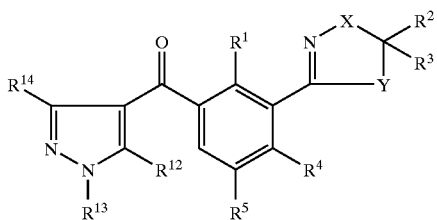

where:

X is O, $NR^6$ or $CR^7R^8$;

Y is O, S, $NR^9$ or $CR^{10}R^{11}$;

$R^1$ is nitro, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, $C_1-C_4$-alkylsulfonyl or $C_1-C_4$-haloalkylsulfonyl;

$R^2,R^3,R^7,R^8,R^{10},R^{11}$ are hydrogen, $C_1-C_4$-alkyl or $C_1-C_4$-haloalkyl;

or $R^3$ and $R^6$ or $R^3$ and $R^8$ or $R^3$ and $R^9$ or $R^3$ and $R^{11}$ together form a bond;

$R^4$ is halogen, nitro, $C_1-C_4$-haloalkyl, $C_1-C_4$-alkoxy, $C_1-C_4$-haloalkoxy, $C_1-C_4$-alkylthio, $C_1-C_4$-haloalkylthio, $C_1-C_4$-alkylsulfonyl or $C_1-C_4$-haloalkylsulfonyl;

$R^5$ is hydrogen, halogen or $C_1-C_4$-alkyl;

$R^6,R^9$ are hydrogen or $C_1-C_6$-alkyl;

$R^{12}$ is hydroxyl, $C_1-C_6$-alkoxy, $C_3-C_6$-alkenyloxy, $C_1-C_6$-alkylsulfonyloxy, $C_1-C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1-C_4$-alkyl, $C_1-C_4$-haloalkyl, $C_1-C_4$-alkoxy or $C_1-C_4$-haloalkoxy;

$R^{13}$ is a cyclic ring system containing 3 to 14 ring atoms which may be partially or fully halogenated and/or may carry one to three of the following groups: $C_1-C_4$-alkyl, $C_1-C_4$-alkoxy, $C_1-C_4$-haloalkyl or $C_1-C_4$-haloalkoxy;

$R^{14}$ is hydrogen or $C_1-C_4$-alkyl;

and their agriculturally useful salts.

Moreover, the invention relates to processes for preparing compounds of the formula I, to compositions comprising them and to the use of these derivatives or of compositions comprising them for controlling harmful plants.

Cycloalkyl-substituted pyrazolylbenzoyl derivatives which are substituted in the 3-position of the benzoyl radical by an N-bonded heterocycle or by phenyl are disclosed in the literature, for example in WO 98/42678 and WO 98/52926.

However, the herbicidal properties of the prior art compounds and their compatibility with crop plants may not be entirely satisfactory.

It is an object of the present invention to provide novel, in particular herbicidally active, compounds having improved properties.

We have found that this object is achieved by the 1-cycloalkylpyrazolylbenzoyl derivatives of the formula I and their herbicidal action.

Furthermore, we have found herbicidal compositions which comprise the compounds I and have very good herbicidal action. Moreover, we have found processes for preparing these compositions and methods for controlling undesirable vegetation using the compounds I.

Depending on the substitution pattern, the compounds of the formula I may contain one or more chiral centers, in which case they are present as enantiomers or mixtures of diastereomers. The invention provides both the pure enantiomers or diastereomers and their mixtures.

The compounds of the formula I can also be present in the form of their agriculturally useful salts, the kind of salt usually being immaterial. In general, the salts of those cations or the acid addition salts of those acids are suitable whose cations and anions, respectively, do not adversely affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced here by $C_1-C_4$-alkyl, hydroxy-$C_1-C_4$-alkyl, $C_1-C_4$-alkoxy-$C_1-C_4$-alkyl, hydroxy-$C_1-C_4$-alkoxy-$C_1-C_4$-alkyl, phenyl or benzyl, preferably ammonium, dimethylassonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1-C_4$-alkyl)sulfonium, and sulfoxonium ions, preferably tri($C_1-C_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1-C_4$-alkanoic acids, preferably formate, acetate, propionate and butyrate.

The organic molecular moieties mentioned for the substituents $R^1$–$R^{12}$ or as radicals on phenyl rings are collective terms for individual enumerations of the individual group members. All hydrocarbon chains, i.e. all alkyl, alkylcarbonyl, haloalkyl, alkoxy, haloalkoxy, alkylcarbonyloxy, alkylsulfonyloxy, alkylthio, haloalkylthio, alkylsulfonyl, haloalkylsulfonyl, alkenyl and alkenyloxy moieties can be straight-chain or branched. Unless indicated otherwise, halogenated substituents preferably carry one to five identical or different halogen atoms. The term halogen represents in each case fluorine, chlorine, bromine or iodine.

Examples of other meanings are:

$C_1-C_4$-alkyl, and the alkyl moieties of $C_1-C_4$-alkylcarbonyl and $C_1-C_4$-alkylcarbonyloxy: for example methyl, ethyl, propyl, 1-methylethyl, butyl, 1-methylpropyl, 2-methylpropyl and 1,1-dimethylethyl;

$C_1-C_6$-alkyl, and the alkyl moieties of $C_1-C_6$-alkylcarbonyl and $C_1-C_6$-alkylcarbonyloxy: $C_1-C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3- dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoramethyl, dichlorofluoromethyl, chlorodifluoromethyl, bromoethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy: for example methoxy, ethoxy, propoxy, 1-methylethoxy, butoxy, 1-methylpropoxy, 2-methylpropoxy and 1,1-dimethylethoxy;

$C_1$–$C_6$-alkoxy: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylthio: for example methylthio, ethylthio, propylthio, 1-methylethylthio, butylthio, 1-methylpropylthio, 2-methylpropylthio and 1,1-dimethylethylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_4$-alkylsulfonyl ($C_1$–$C_4$-alkyl-S(=O)$_2$-), and the alkylsulfonyl moieties of $C_1$–$C_4$-alkylsulfonyloxy: for example methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl, and the alkylsulfonyl moieties of $C_1$–$C_6$-alkylsulfonyloxy: a $C_1$–$C_4$-alkylsulfonyl radical as mentioned above, and also, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl and nonafluorobutylsulfonyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy; 1-ethyl-1-methylprop-2-en-1-yloxy, 1-ethyl-2-methylprop-1-en-1-yloxy and 1-ethyl-2-methylprop-2-en-1-yloxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl.

The term "cyclic ring system having 3 to 14 ring atoms" denotes: $C_3$–$C_8$-cycloalkyl, $C_3$–$C_8$-cycloalkenyl, a bi- or tricyclic carbocyclic or heterocyclic ring system having up to 14 ring atoms, where the ring system may be saturated or contain one, two or three double bonds and, in the case of the heterocyclic rings, may contain one to three heteroatoms selected from the group consisting of oxygen, nitrogen and sulfur. The "cyclic ring systems having 3 to 14 ring atoms" may be partially or fully halogenated and/or may carry one to three of the following groups:

$C_1$–$C_4$-alkyl, $C_1$–$C_4$-alkoxy, $C_1$–$C_4$-haloalkyl or $C_1$–$C_4$-haloalkoxy.

Examples of other meanings are:

$C_3$–$C_6$-cycloalkyl: cyclopropyl, cyclobutyl, cyclopentyl or cyclohexyl;

$C_3$–$C_8$-cycloalkyl: $C_3$–$C_6$-cycloalkyl as mentioned above, and also cycloheptyl or cyclooctyl;

$C_5$–$C_6$-cycloalkenyl: cyclopentenyl or cyclohexenyl;

$C_3$–$C_6$-cycloalkenyl: $C_5$–$C_6$-cycloalkenyl as mentioned above, and also cyclopropenyl or cyclobutenyl;

$C_3$–$C_8$-cycloalkenyl: $C_3$–$C_6$-cycloalkenyl as mentioned above, and also cycloheptenyl or cyclooctenyl;

bi- or tricyclic ring system: for example adamantyl, norbornyl, camphyl, camphenyl or norbornenyl.

The phenyl rings are preferably unsubstituted or carry one to three halogen atoms and/or one nitro group, one cyano group, one or two methyl, trifluoromethyl, methoxy or trifluoromethoxy groups.

Emphasis is given to the 1-cycloalkylpyrazolylbenzoyl derivatives of the formula I where the variables both on their own and in combination with one another have the following meanings:

X is O, $NR^6$ or $CR^7R^8$;

Y is O, S, $NR^9$ or $CR^{10}R^{11}$;

$R^1$ is nitro, halogen, $C_1$–$C_4$-alkyl or $C_1$–$C_4$-alkoxy; particularly preferably halogen, such as fluorine, chlorine or bromine, $C_1$–$C_4$-alkyl, such as methyl or ethyl, or $C_1$–$C_4$-alkoxy, such as methoxy or ethoxy; with very particular preference chlorine, methyl or methoxy;

$R^2, R^3, R^7, R^8, R^{10}, R^{11}$ are hydrogen, $C_1$–$C_4$-alkyl or $C_1$–$C_4$-haloalkyl; particularly preferably hydrogen, methyl, ethyl, propyl, 1-methylethyl, fluoromethyl or chloromethyl; with very particular preference hydrogen, methyl, ethyl or chloromethyl;

or $R^3$ and $R^6$ or $R^3$ and $R^8$ or $R^3$ and $R^9$ or $R^3$ and $R^{11}$ together form a bond;

$R^4$ is halogen, nitro, $C_1$–$C_4$-haloalkyl, $C_1$–$C_4$-alkoxy, $C_1$–$C_4$-haloalkoxy, $C_1$–$C_4$-alkylthio or $C_1$–$C_4$-alkylsulfonyl; particularly preferably halogen, such as chlorine or bromine, nitro, $C_1$–$C_2$-haloalkyl, such as difluoromethyl or trifluoromethyl, $C_1$–$C_2$-alkoxy, such as methoxy or ethoxy, $C_1$–$C_2$-haloalkoxy, such as difluoromethoxy, chlorodifluoromethoxy or trifluoromethoxy, $C_1$–$C_3$-alkylthio, such as methylthio, ethylthio or 1-methyl-1-ethylthio, or $C_1$–$C_3$-alkylsulfonyl, such as methylsulfonyl, ethylsulfonyl, 1-methylethylsulfonyl or propylsulfonyl;

$R^5$ is hydrogen, halogen or methyl or ethyl; particularly preferably hydrogen, chlorine or methyl; with very particular preference hydrogen;

$R^6$, $R^9$ are hydrogen or $C_1$–$C_4$-alkyl; particularly preferably hydrogen, methyl or ethyl; with very particular preference methyl;

$R^{12}$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl, $C_1$–$C_4$-alkoxy, $C_3$–$C_6$-alkenyloxy, $C_1$–$C_4$-alkylsulfonyloxy, $C_1$–$C_4$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_3$–$C_8$-cycloalkyl, $C_3$–$C^8$-cycloalkenyl, a bi- or tricyclic carbocyclic or heterocyclic ring system having up to 14 ring atoms, where the ring system may be saturated or contain one, two or three double bonds and, in the case of the heterocyclic rings, may contain one to three heteroatoms selected from the group consisting of oxygen, nitrogen and sulfur. The "cyclic ring systems having 3 to 14 ring atoms" may be partially or fully halogenated and/or may carry one to three of the following groups: $C_1$–$C_4$-alkyl, $C_1$–$C_4$-alkoxy, $C_1$–$C_4$-haloalkyl or $C_1$–$C_4$-haloalkoxy;

particularly preferably $C_3$–$C_8$-cycloalkyl, $C_3$–$C_8$-cycloalkenyl or a bi- or tricyclic carbocyclic ring system which contains up to 14 ring atoms and is saturated or contains one, two or three double bonds, and where the radicals mentioned may be partially or fully halogenated and/or may carry one to three of the following groups: $C_1$–$C_4$-alkyl, $C_1$–$C_4$-alkoxy, $C_1$–$C_4$-haloalkyl or $C_1$–$C_4$-haloalkoxy; with very particular preference $C_3$–$C_6$-cycloalkyl, $C_5$–$C_6$-cycloalkenyl or a bi- or tricyclic carbocyclic ring system selected from the group consisting of: adamantyl, norbornyl, camphyl, camphenyl or norbornenyl; more preferably $C_3$–$C_6$-cycloalkyl; with most preference cyclopropyl;

$R^{14}$ is hydrogen or $C_1$–$C_4$-alkyl; particularly preferably hydrogen or methyl.

Preference is given to the 1-cycloalkylpyrazolylbenzoyl derivatives of the formula I where:

X is O;

$R^1$ is nitro, halogen, $C_1$–$C_4$-alkyl or $C_1$–$C_4$-alkoxy; particularly preferably halogen, $C_1$–$C_4$-alkyl or $C_1$–$C_4$-alkoxy; with particular preference halogen, such as fluorine, chlorine or bromine, methyl or ethyl or methoxy or ethoxy; with very particular preference chlorine, methyl or methoxy;

$R^4$ is halogen, nitro, $C_1$–$C_4$-haloalkyl, $C_1$–$C_4$-alkoxy, $C_1$–$C_4$-haloalkoxy, $C_1$–$C_4$-alkylthio or $C_1$–$C_4$-alkylsulfonyl; particularly preferably halogen, such as chlorine or bromine, nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy, chlorodifluoromethoxy or trifluoromethoxy, $C_1$–$C_2$-alkylthio, such as methylthio or ethylthio, or $C_1$–$C_2$-alkylsulfonyl, such as methylsulfonyl or ethylsulfonyl.

Particular preference is given to the 1-cycloalkylpyrazolylbenzoyl derivatives of the formula I where X is O;

Y is $CR^{10}R^{11}$;

$R^1$ is halogen, $C_1$–$C_4$-alkyl or $C_1$–$C_4$-alkoxy; particularly preferably halogen, such as fluorine, chlorine or bromine, methyl or ethyl or methoxy or ethoxy; with very particular preference chlorine, methyl or methoxy;

$R^2,R^3,R^{10},R^{11}$ are hydrogen, $C_1$–$C_4$-alkyl; or $R^3$ and $R^{11}$ together form a bond; particularly preferably hydrogen, methyl or ethyl; or $R^3$ and $R^{11}$ together form a bond;

$R^4$ is nitro, $C_1$–$C_4$-haloalkyl, $C_1$–$C_4$-alkoxy or $C_1$–$C_4$-haloalkoxy; particularly preferably nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy;

$R^5$ is hydrogen;

$R^{12}$ is hydroxyl, $C_1$–$C_6$-alkylsulfonyloxy, $C^1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^{13}$ is $C_3$–$C_6$-cycloalkyl, $C_5$–$C_6$-cycloalkenyl or a bi- or tricyclic carbocyclic ring system selected from the group consisting of: adamantyl, norbornyl, camphyl, camphenyl and norbornenyl; particularly preferably $C_3$–$C_6$-cycloalkyl; with very particular preference cyclopropyl.

Most preference is given to the 1-cycloalkylpyrazolylbenzoyl derivatives of the formula I where X is O;

Y is $CR^{10}R^{11}$;

$R^2,R^3,R^{10},R^{11}$ are hydrogen or methyl or ethyl; preferably hydrogen or methyl.

Most preference is also given to the 1-cycloalkylpyrazolylbenzoyl derivatives of the formula I where X is O;

Y is $CR^{10}R^{11}$;

$R^2,R^{10}$ are hydrogen or methyl or ethyl; preferably hydrogen or methyl;

$R^3$ and $R^{11}$ together form a bond.

Particular preference is also given to the 1-cycloalkylpyrazolylbenzoyl derivatives of the formula I where X is O;

Y is $CR^{10}R^{11}$;

$R^1$ is halogen, $C_1$–$C_4$-alkyl or $C_1$–$C_4$-alkoxy; particularly preferably halogen, such as fluorine, chlorine or bromine, methyl or ethyl or methoxy or ethoxy; with particular preference chlorine, methyl or methoxy;

$R^2,R^3,R^{10},R^{11}$ are hydrogen or $C_1$–$C_4$-alkyl; or $R^3$ and $R^{11}$ together form a bond; particularly preferably hydrogen, methyl or ethyl; or $R^3$ and $R^{11}$ together form a bond;

$R^4$ is halogen, $C_1$–$C_4$-alkylthio or $C_1$–$C_4$-alkylsulfonyl; particularly preferably chlorine or bromine, methylthio, ethylthio or 1-methyl-1-ethylthio or methylsulfonyl, ethylsulfonyl, 1-methylethylsulfonyl or propylsulfonyl;

$R^5$ is hydrogen;

$R^{12}$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^{13}$ is $C_3$–$C_6$-cycloalkyl, $C_5$–$C_6$-cycloalkenyl or a bi- or tricyclic ring system selected from the group consisting of: adamantyl, norbornyl, camphyl, camphenyl and norbornenyl; particularly preferably $C_3$–$C_6$-cycloalkyl; with particular preference cyclopropyl.

Most preference is given to the 1-cycloalkylpyrazolylbenzoyl derivatives of the formula I where X is O;

Y is $CR^{10}R^{11}$;

$R^2, R^3, R^{10}, R^{11}$ are hydrogen or methyl or ethyl; preferably hydrogen or methyl.

Most preference is also given to the 1-cycloalkylpyrazolylbenzoyl derivatives of the formula I where X is O;

Y is $CR^{10}R^{11}$;

$R^2, R^{10}$ are hydrogen or methyl or ethyl; preferably hydrogen or methyl;

$R^3$ and $R^{11}$ together form a bond.

Preference is also given to the 1-cycloalkylpyrazolylbenzoyl derivatives of the formula I where the variables have the following meanings:

X is $NR^6$;

$R^1$ is nitro, halogen, $C_1$–$C_4$-alkyl or $C_1$–$C_4$-alkoxy; particularly preferably halogen, $C_1$–$C_4$-alkyl or $C_1$–$C_4$-alkoxy; with particular preference halogen, such as fluorine, chlorine or bromine, methyl or ethyl or methoxy or ethoxy; with very particular preference chlorine, methyl or methoxy;

$R^4$ is halogen, nitro, $C_1$–$C_4$-haloalkyl, $C_1$–$C_4$-alkoxy, $C_1$–$C_4$-haloalkoxy, $C_1$–$C_4$-alkylthio or $C_1$–$C_4$-alkylsulfonyl; particularly preferably halogen, such as chlorine or bromine, nitro, $C_1$–$C_2$-haloalkyl, such as difluoromethyl or trifluoromethyl, $C_1$–$C_2$-alkoxy, such as methoxy or ethoxy, $C_1$–$C_2$-haloalkoxy, such as difluoromethoxy, chlorodifluoromethoxy or trifluoromethoxy, $C_1$–$C_2$-alkylthio, such as methylthio or ethylthio, or $C_1$–$C_2$-alkylsulfonyl, such as methylsulfonyl or ethylsulfonyl.

Particular preference is given to the 1-cycloalkylpyrazolylbenzoyl derivatives of the formula I where X is $N(C_1$–$C_6$-alkyl); particularly preferably N-methyl, N-ethyl, N-(1-methyl-1-ethyl) or N-propyl;

Y is $NR^9$ or $CR^{10}R^{11}$;

$R^1$ is halogen, $C_1$–$C_4$-alkyl or $C_1$–$C_4$-alkoxy; particularly preferably halogen, such as fluorine, chlorine or bromine, methyl or ethyl or methoxy or ethoxy; with particular preference chlorine, methyl or methoxy;

$R^2, R^3, R^{10}, R^{11}$ are hydrogen or $C_1$–$C_4$-alkyl; or $R^3$ and $R^9$ or $R^3$ and $R^{11}$ together form a bond; particularly preferably hydrogen, methyl or ethyl; or $R^3$ and $R^9$ or $R^3$ and $R^{11}$ together form a bond;

$R^4$ is nitro, $C_1$–$C_4$-haloalkyl, $C_1$–$C_4$-alkoxy or $C_1$–$C_4$-haloalkoxy; particularly preferably nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy;

$R^5$ is hydrogen;

$R^9$ is hydrogen or $C_1$–$C_4$-alkyl; particularly preferably $C_1$–$C_4$-alkyl; with particular preference methyl or ethyl;

$R^{12}$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^{13}$ is $C_3$–$C_6$-cycloalkyl, $C_5$–$C_6$-cycloalkenyl or a bi- or tricyclic carbocyclic ring system selected from the group consisting of: adamantyl, norbornyl, camphyl, camphenyl and norbornenyl; particularly preferably $C_3$–$C_6$-cycloalkyl; with particular preference cyclopropyl.

Most preference is given to the 1-cycloalkylpyrazolylbenzoyl derivatives of the formula I where X is $N$-$(C_1$–$C_6$-alkyl); particularly preferably N-methyl, N-ethyl, N-(1-methyl-1-ethyl) or N-propyl;

Y is $CR^{10}R^{11}$;

$R^2, R^3, R^{10}, R^{11}$ are hydrogen or $C_1$–$C_4$-alkyl; preferably hydrogen, methyl or ethyl; particularly preferably hydrogen or methyl.

Most preference is also given to the 1-cycloalkylpyrazolylbenzoyl derivatives of the formula I where X is $N$-$(C_1$–$C_6$-alkyl); particularly preferably N-methyl, N-ethyl, N-(1-methyl-1-ethyl) or N-propyl;

Y is $NR^9$ or $CR^{10}R^{11}$;

$R^2, R^{10}$ are hydrogen or $C_1$–$C_4$-alkyl; preferably hydrogen, methyl or ethyl; with particular preference hydrogen or methyl;

$R^3$ and $R^9$ or $R^3$ and $R^{11}$ together form a bond.

Particular preference is also given to the 1-cycloalkylpyrazolylbenzoyl derivatives of the formula I where X is $N$-$(C_1$–$C_6$-alkyl); particularly preferably N-methyl, N-ethyl, N-(1-methyl-1-ethyl) or N-propyl;

Y is $NR^9$ or $CR^{10}R^{11}$;

$R^1$ is halogen, $C_1$–$C_4$-alkyl or $C_1$–$C_4$-alkoxy; particularly preferably halogen, such as fluorine, chlorine or bromine, methyl or ethyl or methoxy or ethoxy; with particular preference chlorine, methyl or methoxy;

$R^2, R^3, R^{10}, R^{11}$ are hydrogen or $C_1$–$C_4$-alkyl; or $R^3$ and $R^9$ or $R^3$ and $R^{11}$ together form a bond; particularly preferably hydrogen, methyl or ethyl; or $R^3$ and $R^9$ or $R^3$ and $R^{11}$ together form a bond;

$R^4$ is halogen, $C_1$–$C_4$-alkylthio or $C_1$–$C_4$-alkylsulfonyl; particularly preferably chlorine or bromine, methylthio, ethylthio or 1-methyl-1-ethylthio or methylsulfonyl, ethylsulfonyl, 1-methylethylsulfonyl or propylsulfonyl;

$R^5$ is hydrogen;

$R^9$ is hydrogen or $C_1$–$C_4$-alkyl; particularly preferably $C_1$–$C_4$-alkyl; with particular preference methyl or ethyl;

$R^{12}$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^{13}$ is $C_3$–$C_6$-cycloalkyl, $C_5$–$C_6$-cycloalkenyl or a bi- or tricyclic carbocyclic ring system, selected from the group consisting of: adamantyl, norbornyl, camphyl, camphenyl and norbornenyl; particularly preferably $C_1$–$C_6$-cycloalkyl; with particular preference cyclopropyl.

Most preference is given to the 1-cycloalkylpyrazolylbenzoyl derivatives of the formula I where X is N-($C_1$–$C_6$-alkyl); particularly preferably N-methyl, N-ethyl, N-(1-methyl-1-ethyl) or N-propyl;

Y is $CR^{10}R^{11}$;

$R^2, R^3, R^{10}, R^{11}$ are hydrogen or $C_1$–$C_4$-alkyl; preferably hydrogen, methyl or ethyl; with particular preference hydrogen or methyl.

Most preference is also given to the 1-cycloalkylpyrazolylbenzoyl derivatives of the formula I where X is N-($C_1$–$C_6$-alkyl); particularly preferably N-methyl, N-ethyl, N-(1-methyl-1-ethyl) or N-propyl;

Y is $NR^9$ or $CR^{10}R^{11}$;

$R^2, R^{10}$ are hydrogen or $C_1$–$C_4$-alkyl; preferably hydrogen, methyl or ethyl; with particular preference hydrogen or methyl;

$R^3$ and $R^9$ or $R^3$ and $R^{11}$ together form a bond.

Particular preference is also given to the 1-cycloalkylpyrazolylbenzoyl derivatives of the formula I where X is $NR^6$;

Y is O, S or N-($C_1$–$C_6$-alkyl); particularly preferably O, S or N-methyl, N-ethyl, N-(1-methyl-1-ethyl) or N-propyl;

$R^1$ is halogen, $C_1$–$C_4$-alkyl or $C_1$–$C_4$-alkoxy; particularly preferably halogen, such as fluorine, chlorine or bromine, methyl or ethyl or methoxy or ethoxy; with particular preference chlorine, methyl or methoxy;

$R^2$ is hydrogen or $C_1$–$C_4$-alkyl; particularly preferably hydrogen, methyl or ethyl;

$R^3$ and $R^6$ together form a bond;

$R^5$ is hydrogen;

$R^{12}$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^{13}$ is $C_3$–$C_6$-cycloalkyl, $C_5$–$C_6$-cycloalkenyl or a bi- or tricyclic carbocyclic ring system selected from the group consisting of: adamantyl, norbornyl, camphyl, camphenyl and norbornenyl; particularly preferably $C_3$–$C_6$-cycloalkyl; with particular preference cyclopropyl.

Most preference is given to the 1-cycloalkylpyrazolylbenzoyl derivatives of the formula I where $R^4$ is nitro, $C_1$–$C_4$-haloalkyl, $C_1$–$C_4$-alkoxy or $C_1$–$C_4$-haloalkoxy; particularly preferably nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy.

Most preference is also given to the 1-cycloalkylpyrazolylbenzoyl derivatives of the formula I where $R^4$ is halogen, $C_1$–$C_4$-alkylthio or $C_1$–$C_4$-alkylsulfonyl; particularly preferably chlorine or bromine, methylthio, ethylthio or 1-methyl-1-ethylthio or methylsulfonyl, ethylsulfonyl, 1-methylethylsulfonyl or propylsulfonyl.

Preference is also given to the 1-cycloalkylpyrazolylbenzoyl derivatives of the formula I where:

X is $CR^7R^8$;

$R^1$ is nitro, halogen, $C_1$–$C_4$-alkyl or $C_1$–$C_4$-alkoxy; particularly preferably halogen, $C_1$–$C_4$-alkyl or $C_1$–$C_4$-alkoxy; with particular preference halogen, such as fluorine, chlorine or bromine, methyl or ethyl or methoxy or ethoxy; with very particular preference chlorine, methyl or methoxy;

$R^4$ is halogen, nitro, $C_1$–$C_4$-haloalkyl, $C_1$–$C_4$-alkoxy, $C_1$–$C_4$-haloalkoxy, $C_1$–$C_4$-alkylthio or $C_1$–$C_4$-alkylsulfonyl; particularly preferably halogen, such as chlorine or bromine, nitro, $C_1$–$C_2$-haloalkyl, such as difluoromethyl or trifluoromethyl, $C_1$–$C_2$-alkoxy, such as methoxy or ethoxy, $C_1$–$C_2$-haloalkoxy, such as difluoromethoxy, chlorodifluoromethoxy or trifluoromethoxy, $C_1$–$C_2$-alkylthio, such as methylthio or ethylthio, or $C_1$–$C_2$-alkylsulfonyl, such as methylsulfonyl or ethylsulfonyl.

Particular preference is given to the 1-cycloalkylpyrazolylbenzoyl derivatives of the formula I where X is $CR^7R^8$;

Y is O, S or $NR^9$;

$R^1$ is halogen, $C_1$–$C_4$-alkyl or $C_1$–$C_4$-alkoxy; particularly preferably halogen, such as fluorine, chlorine or bromine, methyl or ethyl, methoxy or ethoxy; with particular preference chlorine, methyl or methoxy;

$R^2, R^3, R^7, R^8$ are hydrogen or $C_1$–$C_4$-alkyl; or $R^3$ and $R^8$ together form a bond; particularly preferably hydrogen, methyl or ethyl; or $R^3$ and $R^8$ together form a bond;

$R^4$ is nitro, $C_1$–$C_4$-haloalkyl, $C_1$–$C_4$-alkoxy or $C_1$–$C_4$-haloalkoxy; particularly preferably nitro, $C_1$–$C_2$-haloalkyl, such as difluoromethyl or trifluoromethyl, $C_1$–$C_2$-alkoxy or $C_1$–$C_2$-haloalkoxy, such as difluoromethyloxy;

$R^5$ is hydrogen;

$R^9$ is hydrogen or $C_1$–$C_4$-alkyl; particularly preferably $C_1$–$C_4$-alkyl;

$R^{12}$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^{13}$ is $C_3$–$C_6$-cycloalkyl, $C_5$–$C_6$-cycloalkenyl or a bi or tricyclic carbocyclic ring system selected from the group consisting of: adamantyl, norbornyl, camphyl, camphenyl and norbornenyl; particularly preferably $C_3$–$C_6$-cycloalkyl; with particular preference cyclopropyl.

Most preference is given to the 1-cycloalkylpyrazolylbenzoyl derivatives of the formula I where X is $CR^7R^8$;

Y is O, S or $NR^9$;

$R^2,R^3,R^7,R^8$ are hydrogen or $C_1$–$C_4$-alkyl; preferably hydrogen, methyl or ethyl; particularly preferably hydrogen or methyl;

$R^9$ is hydrogen or $C_1$–$C_4$-alkyl; preferably $C_1$–$C_4$-alkyl.

Most preference is also given to the 1-cycloalkylpyrazolylbenzoyl derivatives of the formula I where X is $CR^7R^8$;

Y is O, S or $NR^9$;

$R^2,R^7$ are hydrogen or $C_1$–$C_4$-alkyl; preferably hydrogen, methyl or ethyl; particularly preferably hydrogen or methyl;

$R^3$ and $R^8$ together form a bond;

$R^9$ is hydrogen or $C_1$–$C_4$-alkyl; preferably $C_1$–$C_4$-alkyl.

Especially preferred in this case are the 1-cycloalkylpyrazolylbenzoyl derivatives of the formula I where Y is S.

Particular preference is also given to the 1-cycloalkylpyrazolylbenzoyl derivatives of the formula I where X is $CR^7R^8$;

Y is O, S or $NR^9$;

$R^1$ is halogen, $C_1$–$C_4$-alkyl or $C_1$–$C_4$-alkoxy; particularly preferably halogen, such as fluorine, chlorine or bromine, methyl or ethyl or methoxy or ethoxy; with particular preference chlorine, methyl or methoxy;

$R^2,R^3,R^7,R^8$ are hydrogen or $C_1$–$C_4$-alkyl; or $R^3$ and $R^8$ together form a bond; particularly preferably hydrogen, methyl or ethyl; or $R^3$ and $R^8$ together form a bond;

$R^4$ is halogen, $C_1$–$C_4$-alkylthio or $C_1$–$C_4$-alkylsulfonyl; particularly preferably chlorine or bromine, methylthio, ethylthio or 1-methyl-1-ethylthio or methylsulfonyl, ethylsulfonyl, 1-methylethylsulfonyl or propylsulfonyl;

$R^5$ is hydrogen;

$R^9$ is hydrogen or $C_1$–$C_4$-alkyl; particularly preferably $C_1$–$C_4$-alkyl; with particular preference methyl or ethyl;

$R^{12}$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^{13}$ is $C_3$–$C_6$-cycloalkyl, $C_5$–$C_6$-cycloalkenyl or a bi- or tricyclic carbocyclic ring system selected from the group consisting of: adamantyl, norbornyl, camphyl, camphenyl and norbornenyl; particularly preferably $C_3$–$C_6$-cycloalkyl; with particular preference cyclopropyl.

Preference is furthermore given to the 1-cycloalkylpyrazolylbenzoyl derivatives of the formula I where X is $CR^7R^8$;

Y is O, S or $NR^9$;

$R^2,R^3,R^7,R^8$ are hydrogen or $C_1$–$C_4$-alkyl; preferably hydrogen, methyl or ethyl; particularly preferably hydrogen or methyl;

$R^9$ is hydrogen or $C_1$–$C_4$-alkyl; preferably $C_1$–$C_4$-alkyl.

Most preference is also given to the 1-cycloalkylpyrazolylbenzoyl derivatives of the formula I where X is $CR^7R^8$;

Y is O, S or $NR^9$;

$R^2,R^7$ are hydrogen or $C_1$–$C_4$-alkyl; preferably hydrogen, methyl or ethyl; with particular preference hydrogen or methyl;

$R^3$ and $R^8$ together form a bond;

$R^9$ is hydrogen or $C_1$–$C_4$-alkyl; preferably $C_1$–$C_4$-alkyl.

Especially preferred in this case are the 1-cycloalkylpyrazolylbenzoyl derivatives of the formula I where Y is S.

Preference is also given to the 1-cycloalkylpyrazolylbenzoyl derivatives of the formula I where the variables have the following meanings:

X is O;

Y is $CR^{10}R^{11}$;

$R^1$ is halogen, $C_1$–$C_4$-alkyl or $C_1$–$C_4$-alkoxy; particularly preferably chlorine, methyl or methoxy; also particularly preferably halogen or $C_1$–$C_4$-alkyl; with particular preference chlorine or methyl;

$R^1,R^3,R^{10},R^{11}$ are hydrogen;

$R^4$ is $C_1$–$C_4$-alkylsulfonyl; particularly preferably methylsulfonyl;

$R^5$ is hydrogen;

$R^{12}$ is hydroxyl, $C_1$–$C_6$-alkoxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl, $C_1$–$C_6$-alkoxy or phenylcarbonyloxy, where the phenyl radical may be partially or fully halogenated and/or may carry one to three of the following groups; nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_3$–$C_6$-cycloalkyl or a bi- or tricyclic ring system selected from the group consisting of: adamantyl, norbornyl, camphyl, camphenyl or norbornenyl; particularly preferably cyclopropyl, cyclopentyl, 2-norbornyl or 2-adamantyl; with particular preference cyclopentyl or 2-norbornyl; also with particular preference cyclopropyl;

$R^{14}$ is hydrogen;

Preference is also given to the 1-cycloalkylpyrazolylbenzoyl derivatives of the formula I where the variables have the following meanings:

X is O;

Y is $CR^{10}R^{11}$;

$R^1$ is halogen, $C_1$–$C_4$-alkyl or $C_1$–$C_4$-alkoxy;

$R^4$ is $C_1$–$C_4$-alkylsulfonyl;

$R^{13}$ is $C_3$–$C_6$-cycloalkyl.

Most particularly preferred are the compounds of the formula Ia1 (=I where $R^1$=Cl; $R^{13}$=cyclo-$C_3H_5$ and $R^5$ and $R^{14}$=H), in particular the compounds Ia1.1 to Ta1.765 of Table 1, where the radical definitions X, Y and $R^1$ to $R^{14}$ are of particular importance for the compounds according to the invention not only in combination with one another but also in each case on their own.

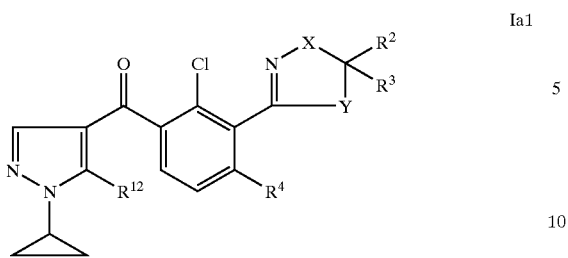

Ia1

TABLE 1

| No. | X | R² | R³ | Y | R⁴ | R¹² |
|---|---|---|---|---|---|---|
| Ia1.1 | O | H | H | CH₂ | SCH₃ | OH |
| Ia1.2 | O | H | H | CH₂ | SCH₂CH₃ | OH |
| Ia1.3 | O | H | H | CH₂ | SO₂CH₃ | OH |
| Ia1.4 | O | H | H | CH₂ | SO₂CH₂CH₃ | OH |
| Ia1.5 | O | H | H | CH₂ | SO₂CH(CH₃)₂ | OH |
| Ia1.6 | O | H | H | CH₂ | SO₂(CH₂)₂CH₃ | OH |
| Ia1.7 | O | H | H | CH₂ | Cl | OH |
| Ia1.8 | O | H | H | CH₂ | Br | OH |
| Ia1.9 | O | H | H | CH₂ | NO₂ | OH |
| Ia1.10 | O | H | H | CH₂ | CHF₂ | OH |
| Ia1.11 | O | H | H | CH₂ | CF₃ | OH |
| Ia1.12 | O | H | H | CH₂ | OCH₃ | OH |
| Ia1.13 | O | H | H | CH₂ | OCH₂CH₃ | OH |
| Ia1.14 | O | H | H | CH₂ | OCHF₂ | OH |
| Ia1.15 | O | H | H | CH₂ | OCF₃ | OH |
| Ia1.16 | O | CH₃ | H | CH₂ | SCH₃ | OH |
| Ia1.17 | O | CH₃ | H | CH₂ | SCH₂CH₃ | OH |
| Ia1.18 | O | CH₃ | H | CH₂ | SO₂CH₃ | OH |
| Ia1.19 | O | CH₃ | H | CH₂ | SO₂CH₂CH₃ | OH |
| Ia1.20 | O | CH₃ | H | CH₂ | SO₂CH(CH₃)₂ | OH |
| Ia1.21 | O | CH₃ | H | CH₂ | SO₂(CH₂)₂CH₃ | OH |
| Ia1.22 | O | CH₃ | H | CH₂ | Cl | OH |
| Ia1.23 | O | CH₃ | H | CH₂ | Br | OH |
| Ia1.24 | O | CH₃ | H | CH₂ | NO₂ | OH |
| Ia1,25 | O | CH₃ | H | CH₂ | CHF₂ | OH |
| Ia1.26 | O | CH₃ | H | CH₂ | CF₃ | OH |
| Ia1.27 | O | CH₃ | H | CH₂ | OCH₃ | OH |
| Ia1.28 | O | CH₃ | H | CH₂ | OCH₂CH₃ | OH |
| Ia1.29 | O | CH₃ | H | CH₂ | OCHF₂ | OH |
| Ia1.30 | O | CH₃ | H | CH₂ | OCF₃ | OH |
| Ia1.31 | O | CH₃ | CH₃ | CH₂ | SCH₃ | OH |
| Ia1.32 | O | CH₃ | CH₃ | CH₂ | SCH₂CH₃ | OH |
| Ia1.33 | O | CH₃ | CH₃ | CH₂ | SO₂CH₃ | OH |
| Ia1.34 | O | CH₃ | CH₃ | CH₂ | SO₂CH₂CH₃ | OH |
| Ia1.35 | O | CH₃ | CH₃ | CH₂ | SO₂CH(CH₃)₂ | OH |
| Ia1.36 | O | CH₃ | CH₃ | CH₂ | SO₂(CH₂)₂CH₃ | OH |
| Ia1.37 | O | CH₃ | CH₃ | CH₂ | Cl | OH |
| Ia1.38 | O | CH₃ | CH₃ | CH₂ | Br | OH |
| Ia1.39 | O | CH₃ | CH₃ | CH₂ | NO₂ | OH |
| Ia1.40 | O | CH₃ | CH₃ | CH₂ | CHF₂ | OH |
| Ia1.41 | O | CH₃ | CH₃ | CH₂ | CF₃ | OH |
| Ia1.42 | O | CH₃ | CH₃ | CH₂ | OCH₃ | OH |
| Ia1.43 | O | CH₃ | CH₃ | CH₂ | OCH₂CH₃ | OH |
| Ia1.44 | O | CH₃ | CH₃ | CH₂ | OCHF₂ | OH |
| Ia1.45 | O | CH₃ | CH₃ | CH₂ | OCF₃ | OH |
| Ia1.46 | O | CH₂Cl | H | CH₂ | SCH₃ | OH |
| Ia1.47 | O | CH₂Cl | H | CH₂ | SCH₂CH₃ | OH |
| Ia1.48 | O | CH₂Cl | H | CH₂ | SO₂CH₃ | OH |
| Ia1.49 | O | CH₂Cl | H | CH₂ | SO₂CH₂CH₃ | OH |
| Ia1.50 | O | CH₂Cl | H | CH₂ | SO₂CH(CH₃)₂ | OH |
| Ia1.51 | O | CH₂Cl | H | CH₂ | SO₂(CH₂)₂CH₃ | OH |
| Ia1.52 | O | CH₂Cl | H | CH₂ | Cl | OH |
| Ia1.53 | O | CH₂Cl | H | CH₂ | Br | OH |
| Ia1.54 | O | CH₂Cl | H | CH₂ | NO₂ | OH |
| Ia1.55 | O | CH₂Cl | H | CH₂ | CHF₂ | OH |
| Ia1.56 | O | CH₂Cl | H | CH₂ | CF₃ | OH |
| Ia1.57 | O | CH₂Cl | H | CH₂ | OCH₃ | OH |
| Ia1.58 | O | CH₂Cl | H | CH₂ | OCH₂CH₃ | OH |
| Ia1.59 | O | CH₂Cl | H | CH₂ | OCHF₂ | OH |
| Ia1.60 | O | CH₂Cl | H | CH₂ | OCF₃ | OH |

TABLE 1-continued

| No. | X | R² | R³ | Y | R⁴ | R¹² |
|---|---|---|---|---|---|---|
| Ia1.61 | O | CH₂CH₃ | H | CH₂ | SCH₃ | OH |
| Ia1.62 | O | CH₂CH₃ | H | CH₂ | SCH₂CH₃ | OH |
| Ia1.63 | O | CH₂CH₃ | H | CH₂ | SO₂CH₃ | OH |
| Ia1.64 | O | CH₂CH₃ | H | CH₂ | SO₃CH₂CH₃ | OH |
| Ia1.65 | O | CH₂CH₃ | H | CH₂ | SO₂CH(CH₃)₂ | OH |
| Ia1.66 | O | CH₂CH₃ | H | CH₂ | SO₂(CH₂)₂CH₃ | OH |
| Ia1.67 | O | CH₂CH₃ | H | CH₂ | Cl | OH |
| Ia1.68 | O | CH₂CH₃ | H | CH₂ | Br | OH |
| Ia1.69 | O | CH₂CH₃ | H | CH₂ | NO₂ | OH |
| Ia1.70 | O | CH₂CH₃ | H | CH₂ | CHF₂ | OH |
| Ia1.71 | O | CH₂CH₃ | R | CH₂ | CF₃ | OH |
| Ia1.72 | O | CH₂CH₃ | H | CH₂ | OCH₃ | OH |
| Ia1.73 | O | CH₂CH₃ | H | CH₂ | OCH₂CH₃ | OH |
| Ia1.74 | O | CH₂CH₃ | H | CH₂ | OCHF₂ | OH |
| Ia1.75 | O | CH₂CH₃ | H | CH₂ | OCF₃ | OH |
| Ia1.76 | O | CH₂CH₃ | CH₂CH₃ | CH₂ | SCH₃ | OH |
| Ia1.77 | O | CH₂CH₃ | CH₂CH₃ | CH₂ | SCH₂CH₃ | OH |
| Ia1.78 | O | CH₂CH₃ | CH₂CH₃ | CH₂ | SO₂CH₃ | OH |
| Ia1.79 | O | CH₂CH₃ | CH₂CH₃ | CH₂ | SO₂CH₂CH₃ | OH |
| Ia1.80 | O | CH₂CH₃ | CH₂CH₃ | CH₂ | SO₂CH(CH₃)₂ | OH |
| Ia1.81 | O | CH₂CH₃ | CH₂CH₃ | CH₂ | SO₂(CH₂)₂CH₃ | OH |
| Ia1.82 | O | CH₂CH₃ | CH₂CH₃ | CH₂ | Cl | OH |
| Ia1.83 | O | CH₂CH₃ | CH₂CH₃ | CH₂ | Br | OH |
| Ia1.84 | O | CH₂CH₃ | CH₂CH₃ | CH₂ | NO₂ | OH |
| Ia1.85 | O | CH₂CH₃ | CH₂CH₃ | CH₂ | CHF₂ | OH |
| Ia1.86 | O | CH₂CH₃ | CH₂CH₃ | CH₂ | CF₃ | OH |
| Ia1.87 | O | CH₂CH₃ | CH₂CH₃ | CH₂ | OCH₃ | OH |
| Ia1.88 | O | CH₂CH₃ | CH₂CH₃ | CH₂ | OCH₂CH₃ | OH |
| Ia1.89 | O | CH₂CH₃ | CH₂CH₃ | CH₂ | OCHF₂ | OH |
| Ia1.90 | O | CH₂CH₃ | CH₂CH₃ | CH₂ | OCF₃ | OH |
| Ia1.91 | O | H | H | CH(CH₃) | SCH₃ | OH |
| Ia1.92 | O | H | H | CH(CH₃) | SCH₂CH₃ | OH |
| Ia1.93 | O | H | H | CH(CH₃) | SO₂CH₃ | OH |
| Ia1.94 | O | H | H | CH(CH₃) | SO₂CH₂CH₃ | OH |
| Ia1.95 | O | H | H | CH(CH₃) | SO₂CH(CH₃)₂ | OH |
| Ia1.96 | O | H | H | CH(CH₃) | SO₂(CH₂)₂CH₃ | CH |
| Ia1.97 | O | H | H | CH(CH₃) | Cl | OH |
| Ia1.98 | O | H | H | CH(CH₃) | Br | OH |
| Ia1.99 | O | H | H | CH(CH₃) | NO₂ | OH |
| Ia1.100 | O | H | H | CH(CH₃) | CHF₂ | OH |
| Ia1.101 | O | H | H | CH(CH₃) | CF₃ | OH |
| Ia1.102 | O | H | H | CH(CH₃) | OCH₃ | OH |
| Ia1.103 | O | H | H | CH(CH₃) | OCH₂CH₃ | OH |
| Ia1.104 | O | H | H | CH(CH₃) | OCHF₂ | OH |
| Ia1.105 | O | H | H | CH(CH₃) | OCF₃ | OH |
| Ia1.106 | O | CH₃ | H | CH(CH₃) | SCH₃ | OH |
| Ia1.107 | O | CH₃ | H | CH(CH₃) | SCH₂CH₃ | OH |
| Ia1.108 | O | CH₃ | H | CH(CH₃) | SO₂CH₃ | OH |
| Ia1.109 | O | CH₃ | H | CH(CH₃) | SO₂CH₂CH₃ | OH |
| Ia1.110 | O | CH₂ | H | CH(CH₃) | SO₂CH(CH₃)₂ | OH |
| Ia1.111 | O | CH₃ | H | CH(CH₃) | SO₂(CH₂)₂CH₃ | OH |
| Ia1.112 | O | CH₃ | H | CH(CH₃) | Cl | OH |
| Ia1.113 | O | CH₃ | H | CH(CH₃) | Br | OH |
| Ia1.114 | O | CH₃ | H | CH(CH₃) | NO₂ | OH |
| Ia1.115 | O | CH₃ | H | CH(CH₃) | CHF₂ | OH |
| Ia1.116 | O | CH₃ | H | CH(CH₃) | CF₃ | OH |
| Ia1.117 | O | CH₃ | H | CH(CH₃) | OCH₃ | OH |
| Ia1.118 | O | CH₃ | H | CH(CH₃) | OCH₂CH₃ | OH |
| Ia1.119 | O | CH₃ | H | CH(CH₃) | OCHF₂ | OH |
| Ia1.120 | O | CH₃ | H | CH(CH₃) | OCF₃ | OH |
| Ia1.121 | O | CH₃ | CH₃ | CH(CH₃) | SCH₃ | OH |
| Ia1.122 | O | CH₃ | CH₃ | CH(CH₃) | SCH₂CH₃ | OH |
| Ia1.123 | O | CH₃ | CH₃ | CH(CH₃) | SO₂CH₃ | OH |
| Ia1.124 | O | CH₃ | CH₃ | CH(CH₃) | SO₂CH₂CH₃ | OH |
| Ia1.125 | O | CH₃ | CH₃ | CH(CH₃) | SO₂CH(CH₃)₂ | OH |
| Ia1.126 | O | CH₃ | CH₃ | CH(CH₃) | SO₂(CH₂)₂CH₃ | OH |
| Ia1.127 | O | CH₃ | CH₃ | CH(CH₃) | Cl | OH |
| Ia1.128 | O | CH₃ | CH₃ | CH(CH₃) | Br | OH |
| Ia1.129 | O | CH₃ | CH₃ | CH(CH₃) | NO₂ | OH |
| Ia1.130 | O | CH₃ | CH₃ | CH(CH₃) | CHF₂ | OH |
| Ia1.131 | O | CH₃ | CH₃ | CH(CH₃) | CF₃ | OH |
| Ia1.132 | O | CH₃ | CH₃ | CH(CH₃) | OCH₃ | OH |
| Ia1.133 | O | CH₃ | CH₃ | CH(CH₃) | OCH₂CH₃ | OH |
| Ia1.134 | O | CH₃ | CH₃ | CH(CH₃) | OCHF₂ | OH |
| Ia1.135 | O | CH₃ | CH₃ | CH(CH₃) | OCF₃ | OH |
| Ia1.136 | O | H | H | C(CH₃)₂ | SCH₃ | OH |
| Ia1.137 | O | H | H | C(CH₃)₂ | SCH₂CH₃ | OH |

TABLE 1-continued

| No. | X | R² | R³ | Y | R⁴ | R¹² |
|---|---|---|---|---|---|---|
| Ia1.138 | O | H | H | C(CH₃)₂ | SO₂CH₃ | OH |
| Ia1.139 | O | H | H | C(CH₃)₂ | SO₂CH₂CH₃ | OH |
| Ia1.140 | O | H | H | C(CH₃)₂ | SO₂CH(CH₃)₂ | OH |
| Ia1.141 | O | H | H | C(CH₃)₂ | SO₂(CH₂)₂CH₃ | OH |
| Ia1.142 | O | H | H | C(CH₃)₂ | Cl | OH |
| Ia1.143 | O | H | H | C(CH₃)₂ | Br | OH |
| Ia1.144 | O | H | H | C(CH₃)₂ | NO₂ | OH |
| Ia1.145 | O | H | H | C(CH₃)₂ | CHF₂ | OH |
| Ia1.146 | O | H | H | C(CH₃)₂ | CF₃ | OH |
| Ia1.147 | O | H | H | C(CH₃)₂ | OCH₃ | OH |
| Ia1.148 | O | H | H | C(CH₃)₂ | OCH₂CH₃ | OH |
| Ia1.149 | O | H | H | C(CH₃)₂ | OCHF₂ | OH |
| Ia1.150 | O | H | H | C(CH₃)₂ | OCF₃ | OH |
| Ia1.151 | O | CH₃ | H | C(CH₃)₂ | SCH₃ | OH |
| Ia1.152 | O | CH₃ | H | C(CH₃)₂ | SCH₂CH₃ | OH |
| Ia1.153 | O | CH₃ | H | C(CH₃)₂ | SO₂CH₃ | OH |
| Ia1.154 | O | CH₃ | H | C(CH₃)₂ | SO₂CH₂CH₃ | OH |
| Ia1.155 | O | CH₃ | H | C(CH₃)₂ | SO₂CH(CH₃)₂ | OH |
| Ia1.156 | O | CH₃ | H | C(CH₃)₂ | SO₂(CH₂)₂CH₃ | OH |
| Ia1.157 | O | CH₃ | H | C(CH₃)₂ | Cl | OH |
| Ia1.158 | O | CH₃ | H | C(CH₃)₂ | Br | OH |
| Ia1.159 | O | CH₃ | H | C(CH₃)₂ | NO₂ | OH |
| Ia1.160 | O | CH₃ | H | C(CH₃)₂ | CHF₂ | OH |
| Ia1.161 | O | CH₃ | H | C(CH₃)₂ | CF₃ | OH |
| Ia1.162 | O | CH₃ | H | C(CH₃)₂ | OCH₃ | OH |
| Ia1.163 | O | CH₃ | H | C(CH₃)₂ | OCH₂CH₃ | OH |
| Ia1.164 | O | CH₃ | H | C(CH₃)₂ | OCHF₂ | OH |
| Ia1.165 | O | CH₃ | H | C(CH₃)₂ | OCF₃ | OH |
| Ia1.166 | O | CH₃ | CH₃ | C(CH₃)₂ | SCH₃ | OH |
| Ia1.167 | O | CH₃ | CH₃ | C(CH₃)₂ | SCH₂CH₃ | OH |
| Ia1.168 | O | CH₃ | CH₃ | C(CH₃)₂ | SO₂CH₃ | OH |
| Ia1.169 | O | CH₃ | CH₃ | C(CH₃)₂ | SO₂CH₂CH₃ | OH |
| Ia1.170 | O | CH₃ | CH₃ | C(CH₃)₂ | SO₂CH(CH₃)₂ | OH |
| Ia1.171 | O | CH₃ | CH₃ | C(CH₃)₂ | SO₂(CH₂)₂CH₃ | OH |
| Ia1.172 | O | CH₃ | CH₃ | C(CH₃)₂ | Cl | OH |
| Ia1.173 | O | CH₃ | CH₃ | C(CH₃)₂ | Br | OH |
| Ia1.174 | O | CH₃ | CH₃ | C(CH₃)₂ | NO₂ | OH |
| Ia1.175 | O | CH₃ | CH₃ | C(CH₃)₂ | CHF₂ | OH |
| Ia1.176 | O | CH₃ | CH₃ | C(CH₃)₂ | CF₃ | OH |
| Ia1.177 | O | CH₃ | CH₃ | C(CH₃)₂ | OCH₃ | OH |
| Ia1.178 | O | CH₃ | CH₃ | C(CH₃)₂ | OCH₂CH₃ | OH |
| Ia1.179 | O | CH₃ | CH₃ | C(CH₃)₂ | OCHF₂ | OH |
| Ia1.180 | O | CH₃ | CH₃ | C(CH₃)₂ | OCF₃ | OH |
| Ia1.181 | NCH₃ | H | H | CH₂ | SCH₃ | OH |
| Ia1.182 | NCH₃ | H | H | CH₂ | SCH₂CH₃ | OH |
| Ia1.183 | NCH₃ | H | H | CH₂ | SO₂CH₃ | OH |
| Ia1.184 | NCH₃ | H | H | CH₂ | SO₂CH₂CH₃ | OH |
| Ia1.185 | NCH₃ | H | H | CH₂ | SO₂CH(CH₃)₂ | OH |
| Ia1.186 | NCH₃ | H | H | CH₂ | SO₂(CH₂)₂CH₃ | OH |
| Ia1.187 | NCH₃ | H | H | CH₂ | Cl | OH |
| Ia1.188 | NCH₃ | H | H | CH₂ | Br | OH |
| Ia1.189 | NCH₃ | H | H | CH₂ | NO₂ | OH |
| Ia1.190 | NCH₃ | H | H | CH₂ | CHF₂ | OH |
| Ia1.191 | NCH₃ | H | H | CH₂ | CF₃ | OH |
| Ia1.192 | NCH₃ | H | H | CH₂ | OCH₃ | OH |
| Ia1.193 | NCH₃ | H | H | CH₂ | OCH₂CH₃ | OH |
| Ia1.194 | NCH₃ | H | H | CH₂ | OCHF₂ | OH |
| Ia1.195 | NCH₃ | H | H | CH₂ | OCF₃ | OH |
| Ia1.196 | NCH₃ | CH₃ | H | CH₂ | SCH₃ | OH |
| Ia1.197 | NCH₃ | CH₃ | H | CH₂ | SCH₂CH₃ | OH |
| Ia1.198 | NCH₃ | CH₃ | H | CH₂ | SO₂CH₃ | OH |
| Ia1.199 | NCH₃ | CH₃ | H | CH₂ | SO₂CH₂CH₃ | OH |
| Ia1.200 | NCH₃ | CH₃ | H | CH₂ | SO₂CH(CH₃)₂ | OH |
| Ia1.201 | NCH₃ | CH₃ | H | CH₂ | SO₂(CH₂)₂CH₃ | OH |
| Ia1.202 | NCH₃ | CH₃ | H | CH₂ | Cl | OH |
| Ia1.203 | NCH₃ | CH₃ | H | CH₂ | Br | OH |
| Ia1.204 | NCH₃ | CH₃ | H | CH₂ | NO₂ | OH |
| Ia1.205 | NCH₃ | CH₃ | H | CH₂ | CHF₂ | OH |
| Ia1.206 | NCH₃ | CH₃ | H | CH₂ | CF₃ | OH |
| Ia1.207 | NCH₃ | CH₃ | H | CH₂ | OCH₃ | OH |
| Ia1.208 | NCH₃ | CH₃ | H | CH₂ | OCH₂CH₃ | OH |
| Ia1.209 | NCH₃ | CH₃ | H | CH₂ | OCHF₂ | OH |
| Ia1.210 | NCH₃ | CH₃ | H | CH₂ | OCF₃ | OH |
| Ia1.211 | NCH₃ | CH₃ | CH₃ | CH₂ | SCH₃ | OH |
| Ia1.212 | NCH₃ | CH₃ | CH₃ | CH₂ | SCH₂CH₃ | OH |
| Ia1.213 | NCH₃ | CH₃ | CH₃ | CH₂ | SO₂CH₃ | OH |
| Ia1.214 | NCH₃ | CH₃ | CH₃ | CH₂ | SO₂CH₂CH₃ | OH |

TABLE 1-continued

| No. | X | $R^2$ | $R^3$ | Y | $R^4$ | $R^{12}$ |
|---|---|---|---|---|---|---|
| Ia1.215 | $NCH_3$ | $CH_3$ | $CH_3$ | $CH_2$ | $SO_2CH(CH_3)_2$ | OH |
| Ia1.216 | $NCH_3$ | $CH_3$ | $CH_3$ | $CH_2$ | $SO_2(CH_2)_2CH_3$ | OH |
| Ia1.217 | $NCH_3$ | $CH_3$ | $CH_3$ | $CH_2$ | Cl | OH |
| Ia1.218 | $NCH_3$ | $CH_3$ | $CH_3$ | $CH_2$ | Br | OH |
| Ia1.219 | $NCH_3$ | $CH_3$ | $CH_3$ | $CH_2$ | $NO_2$ | OH |
| Ia1.220 | $NCH_3$ | $CH_3$ | $CH_3$ | $CH_2$ | $CHF_2$ | OH |
| Ia1.221 | $NCH_3$ | $CH_3$ | $CH_3$ | $CH_2$ | $CF_3$ | OH |
| Ia1.222 | $NCH_3$ | $CH_3$ | $CH_3$ | $CH_2$ | $OCH_3$ | OH |
| Ia1.223 | $NCH_3$ | $CH_3$ | $CH_3$ | $CH_2$ | $OCH_2CH_3$ | OH |
| Ia1.224 | $NCH_3$ | $CH_3$ | $CH_3$ | $CH_2$ | $OCHF_2$ | OH |
| Ia1.225 | $NCH_3$ | $CH_3$ | $CH_3$ | $CH_2$ | $OCF_3$ | OH |
| Ia1.226 | $NCH_3$ | $CH_2Cl$ | H | $CH_2$ | $SCH_3$ | OH |
| Ia1.227 | $NCH_3$ | $CH_2Cl$ | H | $CH_2$ | $SCH_2CH_3$ | OH |
| Ia1.228 | $NCH_3$ | $CH_2Cl$ | H | $CH_2$ | $SO_2CH_3$ | OH |
| Ia1.229 | $NCH_3$ | $CH_2Cl$ | H | $CH_2$ | $SO_2CH_2CH_3$ | OH |
| Ia1.230 | $NCH_3$ | $CH_2Cl$ | H | $CH_2$ | $SO_2CH(CH_3)_2$ | OH |
| Ia1.231 | $NCH_3$ | $CH_2Cl$ | H | $CH_2$ | $SO_2(CH_2)_2CH_3$ | OH |
| Ia1.232 | $NCH_3$ | $CH_2Cl$ | H | $CH_2$ | Cl | OH |
| Ia1.233 | $NCH_3$ | $CH_2Cl$ | H | $CH_2$ | Br | OH |
| Ia1.234 | $NCH_3$ | $CH_2Cl$ | H | $CH_2$ | $NO_2$ | OH |
| Ia1.235 | $NCH_3$ | $CH_2Cl$ | H | $CH_2$ | $CHF_2$ | OH |
| Ia1.236 | $NCH_3$ | $CH_2Cl$ | H | $CH_2$ | $CF_3$ | OH |
| Ia1.237 | $NCH_3$ | $CH_2Cl$ | H | $CH_2$ | $OCH_3$ | OH |
| Ia1.238 | $NCH_3$ | $CH_2Cl$ | H | $CH_2$ | $OCH_2CH_3$ | OH |
| Ia1.239 | $NCH_3$ | $CH_2Cl$ | H | $CH_2$ | $OCHF_2$ | OH |
| Ia1.240 | $NCH_3$ | $CH_2Cl$ | H | $CH_2$ | $OCF_3$ | OH |
| Ia1.241 | $NCH_3$ | $CH_2CH_3$ | H | $CH_2$ | $SCH_3$ | OH |
| Ia1.242 | $NCH_3$ | $CH_2CH_3$ | H | $CH_2$ | $SCH_2CH_3$ | OH |
| Ia1.243 | $NCH_3$ | $CH_2CH_3$ | H | $CH_2$ | $SO_2CH_3$ | OH |
| Ia1.244 | $NCH_3$ | $CH_2CH_3$ | H | $CH_2$ | $SO_2CH_2CH_3$ | OH |
| Ia1.245 | $NCH_3$ | $CH_2CH_3$ | H | $CH_2$ | $SO_2CH(CH_3)_2$ | OH |
| Ia1.246 | $NCH_3$ | $CH_2CH_3$ | H | $CH_2$ | $SO_2(CH_2)_2CH_3$ | OH |
| Ia1.247 | $NCH_3$ | $CH_2CH_3$ | H | $CH_2$ | Cl | OH |
| Ia1.248 | $NCH_3$ | $CH_2CH_3$ | H | $CH_2$ | Br | OH |
| Ia1.249 | $NCH_3$ | $CH_2CH_3$ | H | $CH_2$ | $NO_2$ | OH |
| Ia1.250 | $NCH_3$ | $CH_2CH_3$ | H | $CH_2$ | $CHF_2$ | OH |
| Ia1.251 | $NCH_3$ | $CH_2CH_3$ | H | $CH_2$ | $CF_3$ | OH |
| Ia1.252 | $NCH_3$ | $CH_2CH_3$ | H | $CH_2$ | $OCH_3$ | OH |
| Ia1.253 | $NCH_3$ | $CH_2CH_3$ | H | $CH_2$ | $OCH_2CH_3$ | OH |
| Ia1.254 | $NCH_3$ | $CH_2CH_3$ | H | $CH_2$ | $OCHF_2$ | OH |
| Ia1.255 | $NCH_3$ | $CH_2CH_3$ | H | $CH_2$ | $OCF_3$ | OH |
| Ia1.256 | $NCH_3$ | $CH_2CH_3$ | $CH_2CH_3$ | $CH_2$ | $SCH_3$ | OH |
| Ia1.257 | $NCH_3$ | $CH_2CH_3$ | $CH_2CH_3$ | $CH_2$ | $SCH_2CH_3$ | OH |
| Ia1.258 | $NCH_3$ | $CH_2CH_3$ | $CH_2CH_3$ | $CH_2$ | $SO_2CH_3$ | OH |
| Ia1.259 | $NCH_3$ | $CH_2CH_3$ | $CH_2CH_3$ | $CH_2$ | $SO_2CH_2CH_3$ | OH |
| Ia1.260 | $NCH_3$ | $CH_2CH_3$ | $CH_2CH_3$ | $CH_2$ | $SO_2CH(CH_3)_2$ | OH |
| Ia1.261 | $NCH_3$ | $CH_2CH_3$ | $CH_2CH_3$ | $CH_2$ | $SO_2(CH_2)_2CH_3$ | OH |
| Ia1.262 | $NCH_3$ | $CH_2CH_3$ | $CH_2CH_3$ | $CH_2$ | Cl | OH |
| Ia1.263 | $NCH_3$ | $CH_2CH_3$ | $CH_2CH_3$ | $CH_2$ | Br | OH |
| Ia1.264 | $NCH_3$ | $CH_2CH_3$ | $CH_2CH_3$ | $CH_2$ | $NO_2$ | OH |
| Ia1.265 | $NCH_3$ | $CH_2CH_3$ | $CH_2CH_3$ | $CH_2$ | $CHF_2$ | OH |
| Ia1.266 | $NCH_3$ | $CH_2CH_3$ | $CH_2CH_3$ | $CH_2$ | $CF_3$ | OH |
| Ia1.267 | $NCH_3$ | $CH_2CH_3$ | $CH_2CH_3$ | $CH_2$ | $OCH_3$ | OH |
| Ia1.268 | $NCH_3$ | $CH_2CH_3$ | $CH_2CH_3$ | $CH_2$ | $OCH_2CH_3$ | OH |
| Ia1.269 | $NCH_3$ | $CH_2CH_3$ | $CH_2CH_3$ | $CH_2$ | $OCHF_2$ | OH |
| Ia1.270 | $NCH_3$ | $CH_2CH_3$ | $CH_2CH_3$ | $CH_2$ | $OCF_3$ | OH |
| Ia1.271 | $NCH_3$ | H | H | $CH(CH_3)$ | $SCH_3$ | OH |
| Ia1.272 | $NCH_3$ | H | H | $CH(CH_3)$ | $SCH_2CH_3$ | OH |
| Ia1.273 | $NCH_3$ | H | H | $CH(CH_3)$ | $SO_2CH_3$ | OH |
| Ia1.274 | $NCH_3$ | H | H | $CH(CH_3)$ | $SO_2CH_2CH_3$ | OH |
| Ia1.275 | $NCH_3$ | H | H | $CH(CH_3)$ | $SO_2CH(CH_3)_2$ | OH |
| Ia1.276 | $NCH_3$ | H | H | $CH(CH_3)$ | $SO_2(CH_2)_2CH_3$ | OH |
| Ia1.277 | $NCH_3$ | H | H | $CH(CH_3)$ | Cl | OH |
| Ia1.278 | $NCH_3$ | H | H | $CH(CH_3)$ | Br | OH |
| Ia1.279 | $NCH_3$ | H | H | $CH(CH_3)$ | $NO_2$ | OH |
| Ia1.280 | $NCH_3$ | H | H | $CH(CH_3)$ | $CHF_2$ | OH |
| Ia1.281 | $NCH_3$ | H | H | $CH(CH_3)$ | $CF_3$ | OH |
| Ia1.282 | $NCH_3$ | H | H | $CH(CH_3)$ | $OCH_3$ | OH |
| Ia1.283 | $NCH_3$ | H | H | $CH(CH_3)$ | $OCH_2CH_3$ | OH |
| Ia1.284 | $NCH_3$ | H | H | $CH(CH_3)$ | $OCHF_2$ | OH |
| Ia1.285 | $NCH_3$ | H | H | $CH(CH_3)$ | $OCF_3$ | OH |
| Ia1.286 | $NCH_3$ | $CH_3$ | H | $CH(CH_3)$ | $SCH_3$ | OH |
| Ia1.287 | $NCH_3$ | $CH_3$ | H | $CH(CH_3)$ | $SCH_2CH_3$ | OH |
| Ia1.288 | $NCH_3$ | $CH_3$ | H | $CH(CH_3)$ | $SO_2CH_3$ | OH |
| Ia1.289 | $NCH_3$ | $CH_3$ | H | $CH(CH_3)$ | $SO_2CH_2CH_3$ | OH |
| Ia1.290 | $NCH_3$ | $CH_3$ | H | $CH(CH_3)$ | $SO_2CH(CH_3)_2$ | OH |
| Ia1.291 | $NCH_3$ | $CH_3$ | H | $CH(CH_3)$ | $SO_2(CH_2)_2CH_3$ | OH |

TABLE 1-continued

| No. | X | $R^2$ | $R^3$ | Y | $R^4$ | $R^{12}$ |
|---|---|---|---|---|---|---|
| Ia1.292 | NCH$_3$ | CH$_3$ | H | CH(CH$_3$) | Cl | OH |
| Ia1.293 | NCH$_3$ | CH$_3$ | H | CH(CH$_3$) | Br | OH |
| Ia1.294 | NCH$_3$ | CH$_3$ | H | CH(CH$_3$) | NO$_2$ | OH |
| Ia1.295 | NCH$_3$ | CH$_3$ | H | CH(CH$_3$) | CHF$_2$ | OH |
| Ia1.296 | NCH$_3$ | CH$_3$ | H | CH(CH$_3$) | CF$_3$ | OH |
| Ia1.297 | NCH$_3$ | CH$_3$ | H | CH(CH$_3$) | OCH$_3$ | OH |
| Ia1.298 | NCH$_3$ | CH$_3$ | H | CH(CH$_3$) | OCH$_2$CH$_3$ | OH |
| Ia1.299 | NCH$_3$ | CH$_3$ | H | CH(CH$_3$) | OCHF$_2$ | OH |
| Ia1.300 | NCH$_3$ | CH$_3$ | H | CH(CH$_3$) | OCF$_3$ | OH |
| Ia1.301 | NCH$_3$ | CH$_3$ | CH$_3$ | CH(CH$_3$) | SCH$_3$ | OH |
| Ia1.302 | NCH$_3$ | CH$_3$ | CH$_3$ | CH(CH$_3$) | SCH$_2$CH$_3$ | OH |
| Ia1.303 | NCH$_3$ | CH$_3$ | CH$_3$ | CH(CH$_3$) | SO$_2$CH$_3$ | OH |
| Ia1.304 | NCH$_3$ | CH$_3$ | CH$_3$ | CH(CH$_3$) | SO$_2$CH$_2$CH$_3$ | OH |
| Ia1.305 | NCH$_3$ | CH$_3$ | CH$_3$ | CH(CH$_3$) | SO$_2$CH(CH$_3$)$_2$ | OH |
| Ia1.306 | NCH$_3$ | CH$_3$ | CH$_3$ | CH(CH$_3$) | SO$_2$(CH$_2$)$_2$H$_3$ | OH |
| Ia1.307 | NCH$_3$ | CH$_3$ | CH$_3$ | CH(CH$_3$) | Cl | OH |
| Ia1.308 | NCH$_3$ | CH$_3$ | CH$_3$ | CH(CH$_3$) | Br | OH |
| Ia1.309 | NCH$_3$ | CH$_3$ | CH$_3$ | CH(CH$_3$) | NO$_2$ | OH |
| Ia1.310 | NCH$_3$ | CH$_3$ | CH$_3$ | CH(CH$_3$) | CHF$_2$ | OH |
| Ia1.311 | NCH$_3$ | CH$_3$ | CH$_3$ | CH(CH$_3$) | CF$_3$ | OH |
| Ia1.312 | NCH$_3$ | CH$_3$ | CH$_3$ | CH(CH$_3$) | OCH$_3$ | OH |
| Ia1.313 | NCH$_3$ | CH$_3$ | CH$_3$ | CH(CH$_3$) | OCH$_2$CH$_3$ | OH |
| Ia1.314 | NCH$_3$ | CH$_3$ | CH$_3$ | CH(CH$_3$) | OCHF$_2$ | OH |
| Ia1.315 | NCH$_3$ | CH$_3$ | CH$_3$ | CH(CH$_3$) | OCF$_3$ | OH |
| Ia1.316 | NCH$_3$ | H | H | C(CH$_3$)$_2$ | SCH$_3$ | OH |
| Ia1.317 | NCH$_3$ | H | H | C(CH$_3$)$_2$ | SCH$_2$CH$_3$ | OH |
| Ia1.318 | NCH$_3$ | H | H | C(CH$_3$)$_2$ | SO$_2$CH$_3$ | OH |
| Ia1.319 | NCH$_3$ | H | H | C(CH$_3$)$_2$ | SO$_2$CH$_2$CH$_3$ | OH |
| Ia1.320 | NCH$_3$ | H | H | C(CH$_3$)$_2$ | SO$_2$CH(CH$_3$)$_2$ | OH |
| Ia1.321 | NCH$_3$ | H | H | C(CH$_3$)$_2$ | SO$_2$(CH$_2$)$_2$CH$_3$ | OH |
| Ia1.322 | NCH$_3$ | H | H | C(CH$_3$)$_2$ | Cl | OH |
| Ia1.323 | NCH$_3$ | H | H | C(CH$_3$)$_2$ | Br | OH |
| Ia1.324 | NCH$_3$ | H | H | C(CH$_3$)$_2$ | NO$_2$ | OH |
| Ia1.325 | NCH$_3$ | H | H | C(CH$_3$)$_2$ | CHF$_2$ | OH |
| Ia1.326 | NCH$_3$ | H | H | C(CH$_3$)$_2$ | CF$_3$ | OH |
| Ia1.327 | NCH$_3$ | H | H | C(CH$_3$)$_2$ | OCH$_3$ | OH |
| Ia1.328 | NCH$_3$ | H | H | C(CH$_3$)$_2$ | OCH$_2$CH$_3$ | OH |
| Ia1.329 | NCH$_3$ | H | H | C(CH$_3$)$_2$ | OCHF$_2$ | OH |
| Ia1.330 | NCH$_3$ | H | H | C(CH$_3$)$_2$ | OCF$_3$ | OH |
| Ia1.331 | NCH$_3$ | CH$_3$ | H | C(CH$_3$)$_2$ | SCH$_3$ | OH |
| Ia1.332 | NCH$_3$ | CH$_3$ | H | C(CH$_3$)$_2$ | SCH$_2$CH$_3$ | OH |
| Ia1.333 | NCH$_3$ | CH$_3$ | H | C(CH$_3$)$_2$ | SO$_2$CH$_3$ | OH |
| Ia1.334 | NCH$_3$ | CH$_3$ | H | C(CH$_3$)$_2$ | SO$_2$CH$_2$CH$_3$ | OH |
| Ia1.335 | NCH$_3$ | CH$_3$ | H | C(CH$_3$)$_2$ | SO$_2$CH(CH$_3$)$_2$ | OH |
| Ia1.336 | NCH$_3$ | CH$_3$ | H | C(CH$_3$)$_2$ | SO$_2$(CH$_2$)$_2$CH$_3$ | OH |
| Ia1.337 | NCH$_3$ | CH$_3$ | H | C(CH$_3$)$_2$ | Cl | OH |
| Ia1.338 | NCH$_3$ | CH$_3$ | H | C(CH$_3$)$_2$ | Br | OH |
| Ia1.339 | NCH$_3$ | CH$_3$ | H | C(CH$_3$)$_2$ | NO$_2$ | OH |
| Ia1.340 | NCH$_3$ | CH$_3$ | H | C(CH$_3$)$_2$ | CHF$_2$ | OH |
| Ia1.341 | NCH$_3$ | CH$_3$ | H | C(CH$_3$)$_2$ | CF$_3$ | OH |
| Ia1.342 | NCH$_3$ | CH$_3$ | H | C(CH$_3$)$_2$ | OCH$_3$ | OH |
| Ia1.343 | NCH$_3$ | CH$_3$ | H | C(CH$_3$)$_2$ | OCH$_2$CH$_3$ | OH |
| Ia1.344 | NCH$_3$ | CH$_3$ | H | C(CH$_3$)$_2$ | OCHF$_2$ | OH |
| Ia1.345 | NCH$_3$ | CH$_3$ | H | C(CH$_3$)$_2$ | OCF$_3$ | OH |
| Ia1.346 | NCH$_3$ | CH$_3$ | CH$_3$ | C(CH$_3$)$_2$ | SCH$_3$ | OH |
| Ia1.347 | NCH$_3$ | CH$_3$ | CH$_3$ | C(CH$_3$)$_2$ | SCH$_2$CH$_3$ | OH |
| Ia1.348 | NCH$_3$ | CH$_3$ | CH$_3$ | C(CH$_3$)$_2$ | SO$_2$CH$_3$ | OH |
| Ia1.349 | NCH$_3$ | CH$_3$ | CH$_3$ | C(CH$_3$)$_2$ | SO$_2$CH$_2$CH$_3$ | OH |
| Ia1.350 | NCH$_3$ | CH$_3$ | CH$_3$ | C(CH$_3$)$_2$ | SO$_2$CH(CH$_3$)$_2$ | OH |
| Ia1.351 | NCH$_3$ | CH$_3$ | CH$_3$ | C(CH$_3$)$_2$ | SO$_2$(CH$_2$)$_2$CH$_3$ | OH |
| Ia1.352 | NCH$_3$ | CH$_3$ | CH$_3$ | C(CH$_3$)$_2$ | Cl | OH |
| Ia1.353 | NCH$_3$ | CH$_3$ | CH$_3$ | C(CH$_3$)$_2$ | Br | OH |
| Ia1.354 | NCH$_3$ | CH$_3$ | CH$_3$ | C(CH$_3$)$_2$ | NO$_2$ | OH |
| Ia1.355 | NCH$_3$ | CH$_3$ | CH$_3$ | C(CH$_3$)$_2$ | CHF$_2$ | OH |
| Ia1.356 | NCH$_3$ | CH$_3$ | CH$_3$ | C(CH$_3$)$_2$ | CF$_3$ | OH |
| Ia1.357 | NCH$_3$ | CH$_3$ | CH$_3$ | C(CH$_3$)$_2$ | OCH$_3$ | OH |
| Ia1.358 | NCH$_3$ | CH$_3$ | CH$_3$ | C(CH$_3$)$_2$ | OCH$_2$CH$_3$ | OH |
| Ia1.359 | NCH$_3$ | CH$_3$ | CH$_3$ | C(CH$_3$)$_2$ | OCHF$_2$ | OH |
| Ia1.360 | NCH$_3$ | CH$_3$ | CH$_3$ | C(CH$_3$)$_2$ | OCF$_3$ | OH |
| Ia1.361 | CH$_2$ | H | H | O | SCH$_3$ | OH |
| Ia1.362 | CH$_2$ | H | H | O | SCH$_2$CH$_3$ | OH |
| Ia1.363 | CH$_2$ | H | H | O | SO$_2$CH$_3$ | OH |
| Ia1.364 | CH$_2$ | H | H | O | SO$_2$CH$_2$CH$_3$ | OH |
| Ia1.365 | CH$_2$ | H | H | O | SO$_2$CH(CH$_3$)$_2$ | OH |
| Ia1.366 | CH$_2$ | H | H | O | SO$_2$(CH$_2$)$_2$CH$_3$ | OH |
| Ia1.367 | CH$_2$ | H | H | O | Cl | OH |
| Ia1.368 | CH$_2$ | H | H | O | Br | OH |

TABLE 1-continued

| No. | X | R² | R³ | Y | R⁴ | R¹² |
|---|---|---|---|---|---|---|
| Ia1.369 | CH₂ | H | H | O | NO₂ | OH |
| Ia1.370 | CH₂ | H | H | O | CHF₂ | OH |
| Ia1.371 | CH₂ | H | H | O | CF₃ | OH |
| Ia1.372 | CH₂ | H | H | O | OCH₃ | OH |
| Ia1.373 | CH₂ | H | H | O | OCH₂CH₃ | OH |
| Ia1.374 | CH₂ | H | H | O | OCHF₂ | OH |
| Ia1.375 | CH₂ | H | H | O | OCF₃ | OH |
| Ia1.376 | CH₂ | CH₃ | H | O | SCH₃ | OH |
| Ia1.377 | CH₂ | CH₃ | H | O | SCH₂CH₃ | OH |
| Ia1.378 | CH₂ | CH₃ | H | O | SO₂CH₃ | OH |
| Ia1.379 | CH₂ | CH₃ | H | O | SO₂CH₂CH₃ | OH |
| Ia1.380 | CH₂ | CH₃ | H | O | SO₂CH(CH₃)₂ | OH |
| Ia1.381 | CH₂ | CH₃ | H | O | SO₂(CH₂)₂CH₃ | OH |
| Ia1.382 | CH₂ | CH₃ | H | O | Cl | OH |
| Ia1.383 | CH₂ | CH₃ | H | O | Br | OH |
| Ia1.384 | CH₂ | CH₃ | H | O | NO₂ | OH |
| Ia1.385 | CH₂ | CH₃ | H | O | CHF₂ | OH |
| Ia1.386 | CH₂ | CH₃ | H | O | CF₃ | OH |
| Ia1.387 | CH₂ | CH₃ | H | O | OCH₃ | OH |
| Ia1.388 | CH₂ | CH₃ | H | O | OCH₂CH₃ | OH |
| Ia1.389 | CH₂ | CH₃ | H | O | OCHF₂ | OH |
| Ia1.390 | CH₂ | CH₃ | H | O | OCF₃ | OH |
| Ia1.391 | CH₂ | CH₃ | CH₃ | O | SCH₃ | OH |
| Ia1.392 | CH₂ | CH₃ | CH₃ | O | SCH₂CH₃ | OH |
| Ia1.393 | CH₂ | CH₃ | CH₃ | O | SO₂CH₃ | OH |
| Ia1.394 | CH₂ | CH₃ | CH₃ | O | SO₂CH₂CH₃ | OH |
| Ia1.395 | CH₂ | CH₃ | CH₃ | O | SO₂CH(CH₃)₂ | OH |
| Ia1.396 | CH₂ | CH₃ | CH₃ | O | SO₂(CH₂)₂CH₃ | OH |
| Ia1.397 | CH₂ | CH₃ | CH₃ | O | Cl | OH |
| Ia1.398 | CH₂ | CH₃ | CH₃ | O | Br | OH |
| Ia1.399 | CH₂ | CH₃ | CH₃ | O | NO₂ | OH |
| Ia1.400 | CH₂ | CH₃ | CH₃ | O | CHF₂ | OH |
| Ia1.401 | CH₂ | CH₃ | CH₃ | O | CF₃ | OH |
| Ia1.402 | CH₂ | CH₃ | CH₃ | O | OCH₃ | OH |
| Ia1.403 | CH₂ | CH₃ | CH₃ | O | OCH₂CH₃ | OH |
| Ia1.404 | CH₂ | CH₃ | CH₃ | O | OCHF₂ | OH |
| Ia1.405 | CH₂ | CH₃ | CH₃ | O | OCF₃ | OH |
| Ia1.406 | CH₂ | H | H | S | SCH₃ | OH |
| Ia1.407 | CH₂ | H | H | S | SCH₂CH₃ | OH |
| Ia1.408 | CH₂ | H | H | S | SO₂CH₃ | OH |
| Ia1.409 | CH₂ | H | H | S | SO₂CH₂CH₃ | OH |
| Ia1.410 | CH₂ | H | H | S | SO₂CH(CH₃)₂ | OH |
| Ia1.411 | CH₂ | H | H | S | SO₂(CH₂)₂CH₃ | OH |
| Ia1.412 | CH₂ | H | H | S | Cl | OH |
| Ia1.413 | CH₂ | H | H | S | Br | OH |
| Ia1.414 | CH₂ | H | H | S | NO₃ | OH |
| Ia1.415 | CH₂ | H | H | S | CHF₂ | OH |
| Ia1.416 | CH₂ | H | H | S | CF₃ | OH |
| Ia1.417 | CH₂ | H | H | S | OCH₃ | OH |
| Ia1.418 | CH₂ | H | H | S | OCH₂CH₃ | OH |
| Ia1.419 | CH₂ | H | H | S | OCHF₂ | OH |
| Ia1.420 | CH₂ | H | H | S | OCF₃ | OH |
| Ia1.421 | CH₂ | CH₃ | H | S | SCH₃ | OH |
| Ia1.422 | CH₂ | CH₃ | H | S | SCH₂CH₃ | OH |
| Ia1.423 | CH₂ | CH₃ | H | S | SO₂CH₃ | OH |
| Ia1.424 | CH₂ | CH₃ | H | S | SO₂CH₂CH₃ | OH |
| Ia1.425 | CH₂ | CH₃ | H | S | SO₂CH(CH₃)₂ | OH |
| Ia1.426 | CH₂ | CH₃ | H | S | SO₂(CH₂)₂CH₃ | OH |
| Ia1.427 | CH₂ | CH₃ | H | S | Cl | OH |
| Ia1.428 | CH₂ | CH₃ | H | S | Br | OH |
| Ia1.429 | CH₂ | CH₃ | H | S | NO₂ | OH |
| Ia1.430 | CH₂ | CH₃ | H | S | CHF₂ | OH |
| Ia1.431 | CH₂ | CH₃ | H | S | CF₃ | OH |
| Ia1.432 | CH₂ | CH₃ | H | S | OCH₃ | OH |
| Ia1.433 | CH₂ | CH₃ | H | S | OCH₂CH₃ | OH |
| Ia1.434 | CH₂ | CH₃ | H | S | OCHF₂ | OH |
| Ia1.435 | CH₂ | CH₃ | H | S | OCF₃ | OH |
| Ia1.436 | CH₂ | CH₃ | CH₃ | S | SCH₃ | OH |
| Ia1.437 | CH₂ | CH₃ | CH₃ | S | SCH₂CH₃ | OH |
| Ia1.438 | CH₂ | CH₃ | CH₃ | S | SO₂CH₃ | OH |
| Ia1.439 | CH₂ | CH₃ | CH₃ | S | SO₂CH₂CH₃ | OH |
| Ia1.440 | CH₂ | CH₃ | CH₃ | S | SO₂CH(CH₃)₂ | OH |
| Ia1.441 | CH₂ | CH₃ | CH₃ | S | SO₂(CH₂)₂CH₃ | OH |
| Ia1.442 | CH₂ | CH₃ | CH₃ | S | Cl | OH |
| Ia1.443 | CH₂ | CH₃ | CH₃ | S | Br | OH |
| Ia1.444 | CH₂ | CH₃ | CH₃ | S | NO₂ | OH |
| Ia1.445 | CH₂ | CH₃ | CH₃ | S | CHF₂ | OH |

TABLE 1-continued

| No. | X | $R^2$ | $R^3$ | Y | $R^4$ | $R^{12}$ |
|---|---|---|---|---|---|---|
| Ia1.446 | $CH_2$ | $CH_3$ | $CH_3$ | S | $CF_3$ | OH |
| Ia1.447 | $CH_2$ | $CH_3$ | $CH_3$ | S | $OCH_3$ | OH |
| Ia1.448 | $CH_2$ | $CH_3$ | $CH_3$ | S | $OCH_2CH_3$ | OH |
| Ia1.449 | $CH_2$ | $CH_3$ | $CH_3$ | S | $OCHF_2$ | OH |
| Ia1.450 | $CH_2$ | $CH_3$ | $CH_3$ | S | $OCF_3$ | OH |
| Ia1.451 | $CH_2$ | H | H | $NCH_3$ | $SCH_3$ | OH |
| Ia1.452 | $CH_2$ | H | H | $NCH_3$ | $SCH_2CH_3$ | OH |
| Ia1.453 | $CH_2$ | H | H | $NCH_3$ | $SO_2CH_3$ | OH |
| Ia1.454 | $CH_2$ | H | H | $NCH_3$ | $SO_2CH_2CH_3$ | OH |
| Ia1.455 | $CH_2$ | H | H | $NCH_3$ | $SO_2CH(CH_3)_2$ | OH |
| Ia1.456 | $CH_2$ | H | H | $NCH_3$ | $SO_2(CH_2)_2CH_3$ | OH |
| Ia1.457 | $CH_2$ | H | H | $NCH_3$ | Cl | OH |
| Ia1.458 | $CH_2$ | H | H | $NCH_3$ | Br | OH |
| Ia1.459 | $CH_2$ | H | H | $NCH_3$ | $NO_2$ | OH |
| Ia1.460 | $CH_2$ | H | H | $NCH_3$ | $CHF_2$ | OH |
| Ia1.461 | $CH_2$ | H | H | $NCH_3$ | $CF_3$ | OH |
| Ia1.462 | $CH_2$ | H | H | $NCH_3$ | $OCH_3$ | OH |
| Ia1.463 | $CH_2$ | H | H | $NCH_3$ | $OCH_2CH_3$ | OH |
| Ia1.464 | $CH_2$ | H | H | $NCH_3$ | $OCHF_2$ | OH |
| Ia1.465 | $CH_2$ | H | H | $NCH_3$ | $OCF_3$ | OH |
| Ia1.466 | $CH_2$ | $CH_3$ | H | $NCH_3$ | $SCH_3$ | OH |
| Ia1.467 | $CH_2$ | $CH_3$ | H | $NCH_3$ | $SCH_2CH_3$ | OH |
| Ia1.468 | $CH_2$ | $CH_3$ | H | $NCH_3$ | $SO_2CH_3$ | OH |
| Ia1.469 | $CH_2$ | $CH_3$ | H | $NCH_3$ | $SO_2CH_2CH_3$ | OH |
| Ia1.470 | $CH_2$ | $CH_3$ | H | $NCH_3$ | $SO_2CH(CH_3)_2$ | OH |
| Ia1.471 | $CH_2$ | $CH_3$ | H | $NCH_3$ | $SO_2(CH_2)_2CH_3$ | OH |
| Ia1.472 | $CH_2$ | $CH_3$ | H | $NCH_3$ | Cl | OH |
| Ia1.473 | $CH_2$ | $CH_3$ | H | $NCH_3$ | Br | OH |
| Ia1.474 | $CH_2$ | $CH_3$ | H | $NCH_3$ | $NO_2$ | OH |
| Ia1.475 | $CH_2$ | $CH_3$ | H | $NCH_3$ | $CHF_2$ | OH |
| Ia1.476 | $CH_2$ | $CH_3$ | H | $NCH_3$ | $CF_3$ | OH |
| Ia1.477 | $CH_2$ | $CH_3$ | H | $NCH_3$ | $OCH_3$ | OH |
| Ia1.478 | $CH_2$ | $CH_3$ | H | $NCH_3$ | $OCH_2CH_3$ | OH |
| Ia1.479 | $CH_2$ | $CH_3$ | H | $NCH_3$ | $OCHF_2$ | OH |
| Ia1.480 | $CH_2$ | $CH_3$ | H | $NCH_3$ | $OCF_3$ | OH |
| Ia1.481 | $CH_2$ | $CH_3$ | $CH_3$ | $NCH_3$ | $SCH_3$ | OH |
| Ia1.482 | $CH_2$ | $CH_3$ | $CH_3$ | $NCH_3$ | $SCH_2CH_3$ | OH |
| Ia1.483 | $CH_2$ | $CH_3$ | $CH_3$ | $NCH_3$ | $SO_2CH_3$ | OH |
| Ia1.484 | $CH_2$ | $CH_3$ | $CH_3$ | $NCH_3$ | $SO_2CH_2CH_3$ | OH |
| Ia1.485 | $CH_2$ | $CH_3$ | $CH_3$ | $NCH_3$ | $SO_2CH(CH_3)_2$ | OH |
| Ia1.486 | $CH_2$ | $CH_3$ | $CH_3$ | $NCH_3$ | $SO_2(CH_2)_2CH_3$ | OH |
| Ia1.487 | $CH_2$ | $CH_3$ | $CH_3$ | $NCH_3$ | Cl | OH |
| Ia1.488 | $CH_2$ | $CH_3$ | $CH_3$ | $NCH_3$ | Br | OH |
| Ia1.489 | $CH_2$ | $CH_3$ | $CH_3$ | $NCH_3$ | $NO_2$ | OH |
| Ia1.490 | $CH_2$ | $CH_3$ | $CH_3$ | $NCH_3$ | $CHF_2$ | OH |
| Ia1.491 | $CH_2$ | $CH_3$ | $CH_3$ | $NCH_3$ | $CF_3$ | OH |
| Ia1.492 | $CH_2$ | $CH_3$ | $CH_3$ | $NCH_3$ | $OCH_3$ | OH |
| Ia1.493 | $CH_2$ | $CH_3$ | $CH_3$ | $NCH_3$ | $OCH_2CH_3$ | OH |
| Ia1.494 | $CH_2$ | $CH_3$ | $CH_3$ | $NCH_3$ | $OCHF_2$ | OH |
| Ia1.495 | $CH_2$ | $CH_3$ | $CH_3$ | $NCH_3$ | $OCF_3$ | OH |
| Ia1.496 | $CHCH_3$ | H | H | O | $SCH_3$ | OH |
| Ia1.497 | $CHCH_3$ | H | H | O | $SCH_2CH_3$ | OH |
| Ia1.498 | $CHCH_3$ | H | H | O | $SO_2CH_3$ | OH |
| Ia1.499 | $CHCH_3$ | H | H | O | $SO_2CH_2CH_3$ | OH |
| Ia1.500 | $CHCH_3$ | H | H | O | $SO_2CH(CH_3)_2$ | OH |
| Ia1.501 | $CHCH_3$ | H | H | O | $SO_2(CH_2)_2CH_3$ | OH |
| Ia1.502 | $CHCH_3$ | H | H | O | Cl | OH |
| Ia1.503 | $CHCH_3$ | H | H | O | Br | OH |
| Ia1.504 | $CHCH_3$ | H | H | O | $NO_2$ | OH |
| Ia1.505 | $CHCH_3$ | H | H | O | $CHF_2$ | OH |
| Ia1.506 | $CHCH_3$ | H | H | O | $CF_3$ | OH |
| Ia1.507 | $CHCH_3$ | H | H | O | $OCH_3$ | OH |
| Ia1.508 | $CHCH_3$ | H | H | O | $OCH_2CH_3$ | OH |
| Ia1.509 | $CHCH_3$ | H | H | O | $OCHF_2$ | OH |
| Ia1.510 | $CHCH_3$ | H | H | O | $OCF_3$ | OH |
| Ia1.511 | $CHCH_3$ | $CH_3$ | H | O | $SCH_3$ | OH |
| Ia1.512 | $CHCH_3$ | $CH_3$ | H | O | $SCH_2CH_3$ | OH |
| Ia1.513 | $CHCH_3$ | $CH_3$ | H | O | $SO_2CH_3$ | OH |
| Ia1.514 | $CHCH_3$ | $CH_3$ | H | O | $SO_2CH_2CH_3$ | OH |
| Ia1.515 | $CHCH_3$ | $CH_3$ | H | O | $SO_2CH(CH_3)_2$ | OH |
| Ia1.516 | $CHCH_3$ | $CH_3$ | H | O | $SO_2(CH_2)_2CH_3$ | OH |
| Ia1.517 | $CHCH_3$ | $CH_3$ | H | O | Cl | OH |
| Ia1.518 | $CHCH_3$ | $CH_3$ | H | O | Br | OH |
| Ia1.519 | $CHCH_3$ | $CH_3$ | H | O | $NO_2$ | OH |
| Ia1.520 | $CHCH_3$ | $CH_3$ | H | O | $CHF_2$ | OH |
| Ia1.521 | $CHCH_3$ | $CH_3$ | H | O | $CF_3$ | OH |
| Ia1.522 | $CHCH_3$ | $CH_3$ | H | O | $OCH_3$ | OH |

TABLE 1-continued

| No. | X | $R^2$ | $R^3$ | Y | $R^4$ | $R^{12}$ |
|---|---|---|---|---|---|---|
| Ia1.523 | CHCH$_3$ | CH$_3$ | H | O | OCH$_2$CH$_3$ | OH |
| Ia1.524 | CHCH$_3$ | CH$_3$ | H | O | OCHF$_2$ | OH |
| Ia1.525 | CHCH$_3$ | CH$_3$ | H | O | OCF$_3$ | OH |
| Ia1.526 | CHCH$_3$ | CH$_3$ | CH$_3$ | O | SCH$_3$ | OH |
| Ia1.527 | CHCH$_3$ | CH$_3$ | CH$_3$ | O | SCH$_2$CH$_3$ | OH |
| Ia1.528 | CHCH$_3$ | CH$_3$ | CH$_3$ | O | SO$_2$CH$_3$ | OH |
| Ia1.529 | CHCH$_3$ | CH$_3$ | CH$_3$ | O | SO$_2$CH$_2$CH$_3$ | OH |
| Ia1.530 | CHCH$_3$ | CH$_3$ | CH$_3$ | O | SO$_2$CH(CH$_3$)$_2$ | OH |
| Ia1.531 | CHCH$_3$ | CH$_3$ | CH$_3$ | O | SO$_2$(CH$_2$)$_2$CH$_3$ | OH |
| Ia1.532 | CHCH$_3$ | CH$_3$ | CH$_3$ | O | Cl | OH |
| Ia1.533 | CHCH$_3$ | CH$_3$ | CH$_3$ | O | Br | OH |
| Ia1.534 | CHCH$_3$ | CH$_3$ | CH$_3$ | O | NO$_2$ | OH |
| Ia1.535 | CHCH$_3$ | CH$_3$ | CH$_3$ | O | CHF$_2$ | OH |
| Ia1.536 | CHCH$_3$ | CH$_3$ | CH$_3$ | O | CF$_3$ | OH |
| Ia1.537 | CHCH$_3$ | CH$_3$ | CH$_3$ | O | OCH$_3$ | OH |
| Ia1.538 | CHCH$_3$ | CH$_3$ | CH$_3$ | O | OCH$_2$CH$_3$ | OH |
| Ia1.539 | CHCH$_3$ | CH$_3$ | CH$_3$ | O | OCHF$_2$ | OH |
| Ia1.540 | CHCH$_3$ | CH$_3$ | CH$_3$ | O | OCF$_3$ | OH |
| Ia1.541 | CHCH$_3$ | H | H | S | SCH$_3$ | OH |
| Ia1.542 | CHCH$_3$ | H | H | S | SCH$_2$CH$_3$ | OH |
| Ia1.543 | CHCH$_3$ | H | H | S | SO$_2$CH$_3$ | OH |
| Ia1.544 | CHCH$_3$ | H | H | S | SO$_2$CH$_2$CH$_3$ | OH |
| Ia1.545 | CHCH$_3$ | H | H | S | SO$_2$CH(CH$_3$)$_2$ | OH |
| Ia1.546 | CHCH$_3$ | H | H | S | SO$_2$(CH$_2$)$_2$CH$_3$ | OH |
| Ia1.547 | CHCH$_3$ | H | H | S | Cl | OH |
| Ia1.548 | CHCH$_3$ | H | H | S | Br | OH |
| Ia1.549 | CHCH$_3$ | H | H | S | NO$_2$ | OH |
| Ia1.550 | CHCH$_3$ | H | H | S | CHF$_2$ | OH |
| Ia1.551 | CHCH$_3$ | H | H | S | CF$_3$ | OH |
| Ia1.552 | CHCH$_3$ | H | H | S | OCH$_3$ | OH |
| Ia1.553 | CHCH$_3$ | H | H | S | OCH$_2$CH$_3$ | OH |
| Ia1.554 | CHCH$_3$ | H | H | S | OCHF$_2$ | OH |
| Ia1.555 | CHCH$_3$ | H | H | S | OCF$_3$ | OH |
| Ia1.556 | CHCH$_3$ | CH$_3$ | H | S | SCH$_3$ | OH |
| Ia1.557 | CHCH$_3$ | CH$_3$ | H | S | SCH$_2$CH$_3$ | OH |
| Ia1.558 | CHCH$_3$ | CH$_3$ | H | S | SO$_2$CH$_3$ | OH |
| Ia1.559 | CHCH$_3$ | CH$_3$ | H | S | SO$_2$CH$_2$CH$_3$ | OH |
| Ia1.560 | CHCH$_3$ | CH$_3$ | H | S | SO$_2$CH(CH$_3$)$_2$ | OH |
| Ia1.561 | CHCH$_3$ | CH$_3$ | H | S | SO$_2$(CH$_2$)$_2$CH$_3$ | OH |
| Ia1.562 | CHCH$_3$ | CH$_3$ | H | S | Cl | OH |
| Ia1.563 | CHCH$_3$ | CH$_3$ | H | S | Br | OH |
| Ia1.564 | CHCH$_3$ | CH$_3$ | H | S | NO$_2$ | OH |
| Ia1.565 | CHCH$_3$ | CH$_3$ | H | S | CHF$_2$ | OH |
| Ia1.566 | CHCH$_3$ | CH$_3$ | H | S | CF$_3$ | OH |
| Ia1.567 | CHCH$_3$ | CH$_3$ | H | S | OCH$_3$ | OH |
| Ia1.568 | CHCH$_3$ | CH$_3$ | H | S | OCH$_2$CH$_3$ | OH |
| Ia1.569 | CHCH$_3$ | CH$_3$ | H | S | OCHF$_2$ | OH |
| Ia1.570 | CHCH$_3$ | CH$_3$ | H | S | OCF$_3$ | OH |
| Ia1.571 | CHCH$_3$ | CH$_3$ | CH$_3$ | S | SCH$_3$ | OH |
| Ia1.572 | CHCH$_3$ | CH$_3$ | CH$_3$ | S | SCH$_2$CH$_3$ | OH |
| Ia1.573 | CHCH$_3$ | CH$_3$ | CH$_3$ | S | SO$_2$CH$_3$ | OH |
| Ia1.574 | CHCH$_3$ | CH$_3$ | CH$_3$ | S | SO$_2$CH$_2$CH$_3$ | OH |
| Ia1.575 | CHCH$_3$ | CH$_3$ | CH$_3$ | S | SO$_2$CH(CH$_3$)$_2$ | OH |
| Ia1.576 | CHCH$_3$ | CH$_3$ | CH$_3$ | S | SO$_2$(CH$_2$)$_2$CH$_3$ | OH |
| Ia1.577 | CHCH$_3$ | CH$_3$ | CH$_3$ | S | Cl | OH |
| Ia1.578 | CHCH$_3$ | CH$_3$ | CH$_3$ | S | Br | OH |
| Ia1.579 | CHCH$_3$ | CH$_3$ | CH$_3$ | S | NO$_2$ | OH |
| Ia1.580 | CHCH$_3$ | CH$_3$ | CH$_3$ | S | CHF$_2$ | OH |
| Ia1.581 | CHCH$_3$ | CH$_3$ | CH$_3$ | S | CF$_3$ | OH |
| Ia1.582 | CHCH$_3$ | CH$_3$ | CH$_3$ | S | OCH$_3$ | OH |
| Ia1.583 | CHCH$_3$ | CH$_3$ | CH$_3$ | S | OCH$_2$CH$_3$ | OH |
| Ia1.584 | CHCH$_3$ | CH$_3$ | CH$_3$ | S | OCHF$_2$ | OH |
| Ia1.585 | CHCH$_3$ | CH$_3$ | CH$_3$ | S | OCF$_3$ | OH |
| Ia1.586 | CHCH$_3$ | H | H | NCH$_3$ | SCH$_3$ | OH |
| Ia1.587 | CHCH$_3$ | H | H | NCH$_3$ | SCH$_2$CH$_3$ | OH |
| Ia1.588 | CHCH$_3$ | H | H | NCH$_3$ | SO$_2$CH$_3$ | OH |
| Ia1.589 | CHCH$_3$ | H | H | NCH$_3$ | SO$_2$CH$_2$CH$_3$ | OH |
| Ia1.590 | CHCH$_3$ | H | H | NCH$_3$ | SO$_2$CH(CH$_3$)$_2$ | OH |
| Ia1.591 | CHCH$_3$ | H | H | NCH$_3$ | SO$_2$(CH$_2$)$_2$CH$_3$ | OH |
| Ia1.592 | CHCH$_3$ | H | H | NCH$_3$ | Cl | OH |
| Ia1.593 | CHCH$_3$ | H | H | NCH$_3$ | Br | OH |
| Ia1.594 | CHCH$_3$ | H | H | NCH$_3$ | NO$_2$ | OH |
| Ia1.595 | CHCH$_3$ | H | H | NCH$_3$ | CHF$_2$ | OH |
| Ia1.596 | CHCH$_3$ | H | H | NCH$_3$ | CF$_3$ | OH |
| Ia1.597 | CHCH$_3$ | H | H | NCH$_3$ | OCH$_3$ | OH |
| Ia1.598 | CHCH$_3$ | H | H | NCH$_3$ | OCH$_2$CH$_3$ | OH |
| Ia1.599 | CHCH$_3$ | H | H | NCH$_3$ | OCHF$_2$ | OH |

TABLE 1-continued

| No. | X | R² | R³ | Y | R⁴ | R¹² |
|---|---|---|---|---|---|---|
| Ia1.600 | CHCH₃ | H | H | NCH₃ | OCF₃ | OH |
| Ia1.601 | CHCH₃ | CH₃ | H | NCH₃ | SCH₃ | OH |
| Ia1.602 | CHCH₃ | CH₃ | H | NCH₃ | SCH₂CH₃ | OH |
| Ia1.603 | CHCH₃ | CH₃ | H | NCH₃ | SO₂CH₃ | OH |
| Ia1.604 | CHCH₃ | CH₃ | H | NCH₃ | SO₂CH₂CH₃ | OH |
| Ia1.605 | CHCH₃ | CH₃ | H | NCH₃ | SO₂CH(CH₃)₂ | OH |
| Ia1.606 | CHCH₃ | CH₃ | H | NCH₃ | SO₂(CH₂)₂CH₃ | OH |
| Ia1.607 | CHCH₃ | CH₃ | H | NCH₃ | Cl | OH |
| Ia1.608 | CHCH₃ | CH₃ | H | NCH₃ | Br | OH |
| Ia1.609 | CHCH₃ | CH₃ | H | NCH₃ | NO₂ | OH |
| Ia1.610 | CHCH₃ | CH₃ | H | NCH₃ | CHF₂ | OH |
| Ia1.611 | CHCH₃ | CH₃ | H | NCH₃ | CF₃ | OH |
| Ia1.612 | CHCH₃ | CH₃ | H | NCH₃ | OCH₃ | OH |
| Ia1.613 | CHCH₃ | CH₃ | H | NCH₃ | OCH₂CH₃ | OH |
| Ia1.614 | CHCH₃ | CH₃ | H | NCH₃ | OCHF₂ | OH |
| Ia1.615 | CHCH₃ | CH₃ | H | NCH₃ | OCF₃ | OH |
| Ia1.616 | CHCH₃ | CH₃ | CH₃ | NCH₃ | SCH₃ | OH |
| Ia1.617 | CHCH₃ | CH₃ | CH₃ | NCH₃ | SCH₂CH₃ | OH |
| Ia1.618 | CHCH₃ | CH₃ | CH₃ | NCH₃ | SO₂CH₃ | OH |
| Ia1.619 | CHCH₃ | CH₃ | CH₃ | NCH₃ | SO₂CH₂CH₃ | OH |
| Ia1.620 | CHCH₃ | CH₃ | CH₃ | NCH₃ | SO₂CH(CH₃)₂ | OH |
| Ia1.621 | CHCH₃ | CH₃ | CH₃ | NCH₃ | SO₂(CH₂)₂CH₃ | OH |
| Ia1.622 | CHCH₃ | CH₃ | CH₃ | NCH₃ | Cl | OH |
| Ia1.623 | CHCH₃ | CH₃ | CH₃ | NCH₃ | Br | OH |
| Ia1.624 | CHCH₃ | CH₃ | CH₃ | NCH₃ | NO₂ | OH |
| Ia1.625 | CHCH₃ | CH₃ | CH₃ | NCH₃ | CHF₂ | OH |
| Ia1.626 | CHCH₃ | CH₃ | CH₃ | NCH₃ | CF₃ | OH |
| Ia1.627 | CHCH₃ | CH₃ | CH₃ | NCH₃ | OCH₃ | OH |
| Ia1.628 | CHCH₃ | CH₃ | CH₃ | NCH₃ | OCH₂CH₃ | OH |
| Ia1.629 | CHCH₃ | CH₃ | CH₃ | NCH₃ | OCHF₂ | OH |
| Ia1.630 | CHCH₃ | CH₃ | CH₃ | NCH₃ | OCF₃ | OH |
| Ia1.631 | C(CH₃)₂ | H | H | O | SCH₃ | OH |
| Ia1.632 | C(CH₃)₂ | H | H | O | SCH₂CH₃ | OH |
| Ia1.633 | C(CH₃)₂ | H | H | O | SO₂CH₃ | OH |
| Ia1.634 | C(CH₃)₂ | H | H | O | SO₂CH₂CH₃ | OH |
| Ia1.635 | C(CH₃)₂ | H | H | O | SO₂CH(CH₃)₂ | OH |
| Ia1.636 | C(CH₃)₂ | H | H | O | SO₂(CH₂)₂CH₃ | OH |
| Ia1.637 | C(CH₃)₂ | H | H | O | Cl | OH |
| Ia1.638 | C(CH₃)₂ | H | H | O | Br | OH |
| Ia1.639 | C(CH₃)₂ | H | H | O | NO₂ | OH |
| Ia1.640 | C(CH₃)₂ | H | H | O | CHF₂ | OH |
| Ia1.641 | C(CH₃)₂ | H | H | O | CF₃ | OH |
| Ia1.642 | C(CH₃)₂ | H | H | O | OCH₃ | OH |
| Ia1.643 | C(CH₃)₂ | H | H | O | OCH₂CH₃ | OH |
| Ia1.644 | C(CH₃)₂ | H | H | O | OCHF₂ | OH |
| Ia1.645 | C(CH₃)₂ | H | H | O | OCF₃ | OH |
| Ia1.646 | C(CH₃)₂ | CH₃ | H | O | SCH₃ | OH |
| Ia1.647 | C(CH₃)₂ | CH₃ | H | O | SCH₂CH₃ | OH |
| Ia1.648 | C(CH₃)₂ | CH₃ | H | O | SO₂CH₃ | OH |
| Ia1.649 | C(CH₃)₂ | CH₃ | H | O | SO₂CH₂CH₃ | OH |
| Ia1.650 | C(CH₃)₂ | CH₃ | H | O | SO₂CH(CH₃)₂ | OH |
| Ia1.651 | C(CH₃)₂ | CH₃ | H | O | SO₂(CH₂)₂CH₃ | OH |
| Ia1.652 | C(CH₃)₂ | CH₃ | H | O | Cl | OH |
| Ia1.653 | C(CH₃)₂ | CH₃ | H | O | Br | OH |
| Ia1.654 | C(CH₃)₂ | CH₃ | H | O | NO₂ | OH |
| Ia1.655 | C(CH₃)₂ | CH₃ | H | O | CHF₂ | OH |
| Ia1.656 | C(CH₃)₂ | CH₃ | H | O | CF₃ | OH |
| Ia1.657 | C(CH₃)₂ | CH₃ | H | O | OCH₃ | OH |
| Ia1.658 | C(CH₃)₂ | CH₃ | H | O | OCH₂CH₃ | OH |
| Ia1.659 | C(CH₃)₂ | CH₃ | H | O | OCHF₂ | OH |
| Ia1.660 | C(CH₃)₂ | CH₃ | H | O | OCF₃ | OH |
| Ia1.661 | C(CH₃)₂ | CH₃ | CH₃ | O | SCH₃ | OH |
| Ia1.662 | C(CH₃)₂ | CH₃ | CH₃ | O | SCH₂CH₃ | OH |
| Ia1.663 | C(CH₃)₂ | CH₃ | CH₃ | O | SO₂CH₃ | OH |
| Ia1.664 | C(CH₃)₂ | CH₃ | CH₃ | O | SO₂CH₂CH₃ | OH |
| Ia1.665 | C(CH₃)₂ | CH₃ | CH₃ | O | SO₂CH(CH₃)₂ | OH |
| Ia1.666 | C(CH₃)₂ | CH₃ | CH₃ | O | SO₂(CH₂)₂CH₃ | OH |
| Ia1.667 | C(CH₃)₂ | CH₃ | CH₃ | O | Cl | OH |
| Ia1.668 | C(CH₃)₂ | CH₃ | CH₃ | O | Br | OH |
| Ia1.669 | C(CH₃)₂ | CH₃ | CH₃ | O | NO₂ | OH |
| Ia1.670 | C(CH₃)₂ | CH₃ | CH₃ | O | CHF₂ | OH |
| Ia1.671 | C(CH₃)₂ | CH₃ | CH₃ | O | CF₃ | OH |
| Ia1.672 | C(CH₃)₂ | CH₃ | CH₃ | O | OCH₃ | OH |
| Ia1.673 | C(CH₃)₂ | CH₃ | CH₃ | O | OCH₂CH₃ | OH |
| Ia1.674 | C(CH₃)₂ | CH₃ | CH₃ | O | OCHF₂ | OH |
| Ia1.675 | C(CH₃)₂ | CH₃ | CH₃ | O | OCF₃ | OH |
| Ia1.676 | C(CH₃)₂ | H | H | S | SCH₃ | OH |

TABLE 1-continued

| No. | X | R² | R³ | Y | R⁴ | R¹² |
|---|---|---|---|---|---|---|
| Ia1.677 | C(CH₃)₂ | H | H | S | SCH₂CH₃ | OH |
| Ia1.678 | C(CH₃)₂ | H | H | S | SO₂CH₃ | OH |
| Ia1.679 | C(CH₃)₂ | H | H | S | SO₂CH₂CH₃ | OH |
| Ia1.680 | C(CH₃)₂ | H | H | S | SO₂CH(CH₃)₂ | OH |
| Ia1.681 | C(CH₃)₂ | H | H | S | SO₂(CH₂)₂CH₃ | OH |
| Ia1.682 | C(CH₃)₂ | H | H | S | Cl | OH |
| Ia1.683 | C(CH₃)₂ | H | H | S | Br | OH |
| Ia1.684 | C(CH₃)₂ | H | H | S | NO₂ | OH |
| Ia1.685 | C(CH₃)₂ | H | H | S | CHF₂ | OH |
| Ia1.686 | C(CH₃)₂ | H | H | S | CF₃ | OH |
| Ia1.687 | C(CH₃)₂ | H | H | S | OCH₃ | OH |
| Ia1.688 | C(CH₃)₂ | H | H | S | OCH₂CH₃ | OH |
| Ia1.689 | C(CH₃)₂ | H | H | S | OCHF₂ | OH |
| Ia1.690 | C(CH₃)₂ | H | H | S | OCF₃ | OH |
| Ia1.691 | C(CH₃)₂ | CH₃ | H | S | SCH₃ | OH |
| Ia1.692 | C(CH₃)₂ | CH₃ | H | S | SCH₂CH₃ | OH |
| Ia1.693 | C(CH₃)₂ | CH₃ | H | S | SO₂CH₃ | OH |
| Ia1.694 | C(CH₃)₂ | CH₃ | H | S | SO₂CH₂CH₃ | OH |
| Ia1.695 | C(CH₃)₂ | CH₃ | H | S | SO₂CH(CH₃)₂ | OH |
| Ia1.696 | C(CH₃)₂ | CH₃ | H | S | SO₂(CH₂)₂CH₃ | OH |
| Ia1.697 | C(CH₃)₂ | CH₃ | H | S | Cl | OH |
| Ia1.698 | C(CH₃)₂ | CH₃ | H | S | Br | OH |
| Ia1.699 | C(CH₃)₂ | CH₃ | H | S | NO₂ | OH |
| Ia1.700 | C(CH₃)₂ | CH₃ | H | S | CHF₂ | OH |
| Ia1.701 | C(CH₃)₂ | CH₃ | H | S | CF₃ | OH |
| Ia1.702 | C(CH₃)₂ | CH₃ | H | S | OCH₃ | OH |
| Ia1.703 | C(CH₃)₂ | CH₃ | H | S | OCH₂CH₃ | OH |
| Ia1.704 | C(CH₃)₂ | CH₃ | H | S | OCHF₂ | OH |
| Ia1.705 | C(CH₃)₂ | CH₃ | H | S | OCF₃ | OH |
| Ia1.706 | C(CH₃)₂ | CH₃ | CH₃ | S | SCH₃ | OH |
| Ia1.707 | C(CH₃)₂ | CH₃ | CH₃ | S | SCH₂CH₃ | OH |
| Ia1.708 | C(CH₃)₂ | CH₃ | CH₃ | S | SO₂CH₃ | OH |
| Ia1.709 | C(CH₃)₂ | CH₃ | CH₃ | S | SO₂CH₂CH₃ | OH |
| Ia1.710 | C(CH₃)₂ | CH₃ | CH₃ | S | SO₂CH(CH₃)₂ | OH |
| Ia1.711 | C(CH₃)₂ | CH₃ | CH₃ | S | SO₂(CH₂)₂CH₃ | OH |
| Ia1.712 | C(CH₃)₂ | CH₃ | CH₃ | S | Cl | OH |
| Ia1.713 | C(CH₃)₂ | CH₃ | CH₃ | S | Br | OH |
| Ia1.714 | C(CH₃)₂ | CH₃ | CH₃ | S | NO₂ | OH |
| Ia1.715 | C(CH₃)₂ | CH₃ | CH₃ | S | CHF₂ | OH |
| Ia1.716 | C(CH₃)₂ | CH₃ | CH₃ | S | CF₃ | OH |
| Ia1.717 | C(CH₃)₂ | CH₃ | CH₃ | S | OCH₃ | OH |
| Ia1.718 | C(CH₃)₂ | CH₃ | CH₃ | S | OCH₂CH₃ | OH |
| Ia1.719 | C(CH₃)₂ | CH₃ | CH₃ | S | OCHF₂ | OH |
| Ia1.720 | C(CH₃)₂ | CH₃ | CH₃ | S | OCF₃ | OH |
| Ia1.721 | C(CH₃)₂ | H | H | NCH₃ | SCH₃ | OH |
| Ia1.722 | C(CH₃)₂ | H | H | NCH₃ | SCH₂CH₃ | OH |
| Ia1.723 | C(CH₃)₂ | H | H | NCH₃ | SO₂CH₃ | OH |
| Ia1.724 | C(CH₃)₂ | H | H | NCH₃ | SO₂CH₂CH₃ | OH |
| Ia1.725 | C(CH₃)₂ | H | H | NCH₃ | SO₂CH(CH₃)₂ | OH |
| Ia1.726 | C(CH₃)₂ | H | H | NCH₃ | SO₂(CH₂)₂CH₃ | OH |
| Ia1.727 | C(CH₃)₂ | H | H | NCH₃ | Cl | OH |
| Ia1.728 | C(CH₃)₂ | H | H | NCH₃ | Br | OH |
| Ia1.729 | C(CH₃)₂ | H | H | NCH₃ | NO₂ | OH |
| Ia1.730 | C(CH₃)₂ | H | H | NCH₃ | CHF₂ | OH |
| Ia1.731 | C(CH₃)₂ | H | H | NCH₃ | CF₃ | OH |
| Ia1.732 | C(CH₃)₂ | H | H | NCH₃ | OCH₃ | OH |
| Ia1.733 | C(CH₃)₂ | H | H | NCH₃ | OCH₂CH₃ | OH |
| Ia1.734 | C(CH₃)₂ | H | H | NCH₃ | OCHF₂ | OH |
| Ia1.735 | C(CH₃)₂ | H | H | NCH₃ | OCF₃ | OH |
| Ia1.736 | C(CH₃)₂ | CH₃ | H | NCH₃ | SCH₃ | OH |
| Ia1.737 | C(CH₃)₂ | CH₃ | H | NCH₃ | SCH₂CH₃ | OH |
| Ia1.738 | C(CH₃)₂ | CH₃ | H | NCH₃ | SO₂CH₃ | OH |
| Ia1.739 | C(CH₃)₂ | CH₃ | H | NCH₃ | SO₂CH₂CH₃ | OH |
| Ia1.740 | C(CH₃)₂ | CH₃ | H | NCH₃ | SO₂CH(CH₃)₂ | OH |
| Ia1.741 | C(CH₃)₂ | CH₃ | H | NCH₃ | SO₂(CH₂)₂CH₃ | OH |
| Ia1.742 | C(CH₃)₂ | CH₃ | H | NCH₃ | Cl | OH |
| Ia1.743 | C(CH₃)₂ | CH₃ | H | NCH₃ | Br | OH |
| Ia1.744 | C(CH₃)₂ | CH₃ | H | NCH₃ | NO₂ | OH |
| Ia1.745 | C(CH₃)₂ | CH₃ | H | NCH₃ | CHF₂ | OH |
| Ia1.746 | C(CH₃)₂ | CH₃ | H | NCH₃ | CF₃ | OH |
| Ia1.747 | C(CH₃)₂ | CH₃ | H | NCH₃ | OCH₃ | OH |
| Ia1.748 | C(CH₃)₂ | CH₃ | H | NCH₃ | OCH₂CH₃ | OH |
| Ia1.749 | C(CH₃)₂ | CH₃ | H | NCH₃ | OCHF₂ | OH |
| Ia1.750 | C(CH₃)₂ | CH₃ | H | NCH₃ | OCF₃ | OH |
| Ia1.751 | C(CH₃)₂ | CH₃ | CH₃ | NCH₃ | SCH₃ | OH |
| Ia1.752 | C(CH₃)₂ | CH₃ | CH₃ | NCH₃ | SCH₂CH₃ | OH |
| Ia1.753 | C(CH₃)₂ | CH₃ | CH₃ | NCH₃ | SO₂CH₃ | OH |

TABLE 1-continued

| No. | X | $R^2$ | $R^3$ | Y | $R^4$ | $R^{12}$ |
|---|---|---|---|---|---|---|
| Ia1.754 | $C(CH_3)_2$ | $CH_3$ | $CH_3$ | $NCH_3$ | $SO_2CH_2CH_3$ | OH |
| Ia1.755 | $C(CH_3)_2$ | $CH_3$ | $CH_3$ | $NCH_3$ | $SO_2CH(CH_3)_2$ | OH |
| Ia1.756 | $C(CH_3)_2$ | $CH_3$ | $CH_3$ | $NCH_3$ | $SO_2(CH_2)_2CH_3$ | OH |
| Ia1.757 | $C(CH_3)_2$ | $CH_3$ | $CH_3$ | $NCH_3$ | Cl | OH |
| Ia1.758 | $C(CH_3)_2$ | $CH_3$ | $CH_3$ | $NCH_3$ | Br | OH |
| Ia1.759 | $C(CH_3)_2$ | $CH_3$ | $CH_3$ | $NCH_3$ | $NO_2$ | OH |
| Ia1.760 | $C(CH_3)_2$ | $CH_3$ | $CH_3$ | $NCH_3$ | $CHF_2$ | OH |
| Ia1.761 | $C(CH_3)_2$ | $CH_3$ | $CH_3$ | $NCH_3$ | $CF_3$ | OH |
| Ia1.762 | $C(CH_3)_2$ | $CH_3$ | $CH_3$ | $NCH_3$ | $OCH_3$ | OH |
| Ia1.763 | $C(CH_3)_2$ | $CH_3$ | $CH_3$ | $NCH_3$ | $OCH_2CH_3$ | OH |
| Ia1.764 | $C(CH_3)_2$ | $CH_3$ | $CH_3$ | $NCH_3$ | $OCHF_2$ | OH |
| Ia1.765 | $C(CH_3)_2$ | $CH_3$ | $CH_3$ | $NCH_3$ | $OCF_3$ | OH |

Most particular preference is also given to the compounds of the formula Ia2, in particular to the compounds Ia2.1, to Ia2.765 which differ from the corresponding compounds Ia1.1 to Ia1.765 in that $R^{14}$ is methyl.

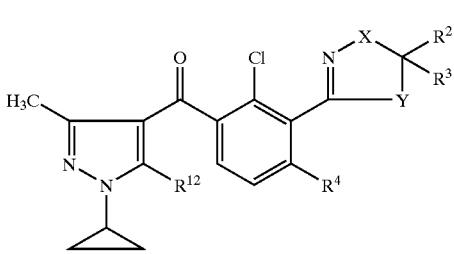

Ia2

Most particular preference is also given to the compounds of the formula Ia3, in particular to the compounds Ia3.1 to Ia3.765 which differ from the compounds Ia1.1 to Ia1.765 in that $R^{13}$ is cyclopentyl.

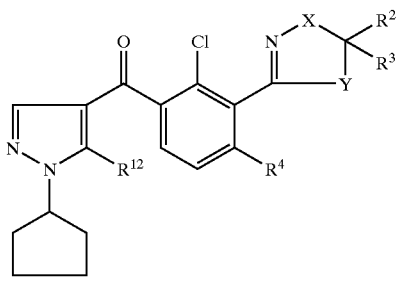

Ia3

Most particular preference is also given to the compounds of the formula Ia4, in particular to the compounds Ia4.1 to Ia4.765 which differ from the compounds Ia1.1 to Ia1.765 in that $R^{13}$ is cyclopentyl and $R^{14}$ is methyl.

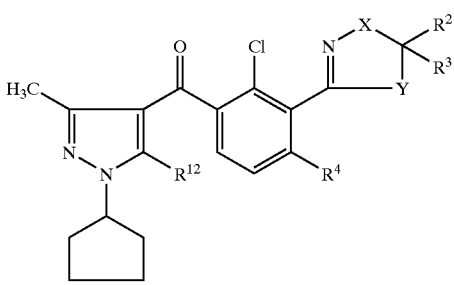

Ia4

Most particular preference is also given to the compounds of the formula Ia5, in particular to the compounds Ia5.1 to Ia5.765 which differ from the compounds Ia1.1 to Ia1.765 in that $R^{13}$ is cyclohexyl.

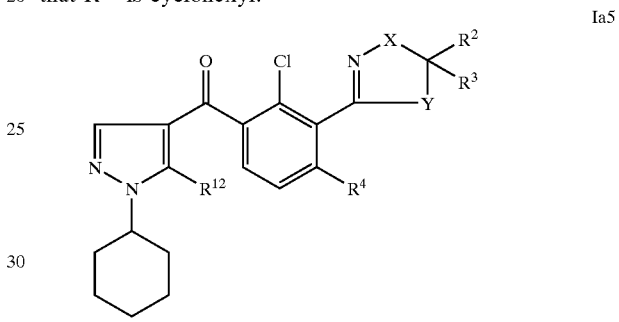

Ia5

Most particular preference is also given to the compounds of the formula Ia6, in particular to the compounds Ia6.1 to Ia6.765 which differ from the compounds Ia1.1 to Ia1.765 in that $R^{13}$ is cyclohexyl and $R^{14}$ is methyl.

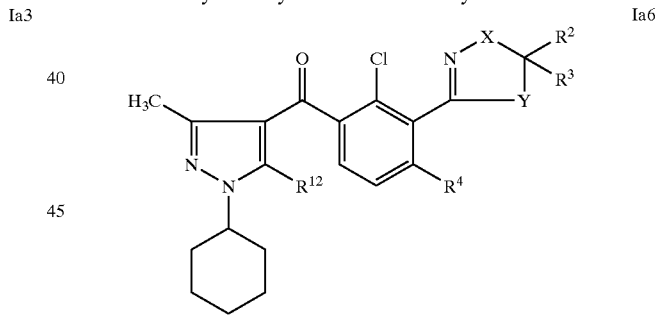

Ia6

Most particular preference is also given to the compounds of the formula Ia7, in particular to the compounds Ia7.1 to Ia7.765 which differ from the compounds Ia1.1 to Ia1.765 in that $R^{13}$ is 2-norbornyl.

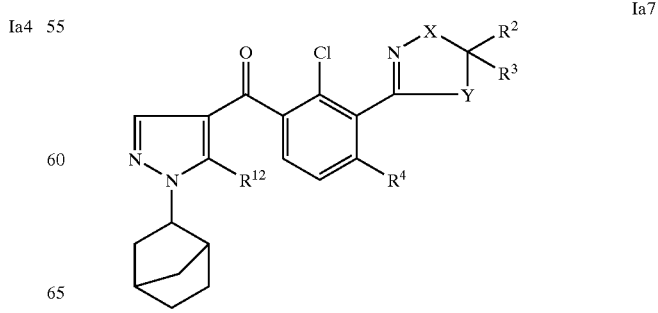

Ia7

Most particular preference is also given to the compounds of the formula Ia8, in particular to the compounds Ia8.1 to Ia8.765 which differ from the compounds Ia1.1 to Ia1.765 in that $R^{13}$ is 2-norbornyl and $R^{14}$ is methyl.

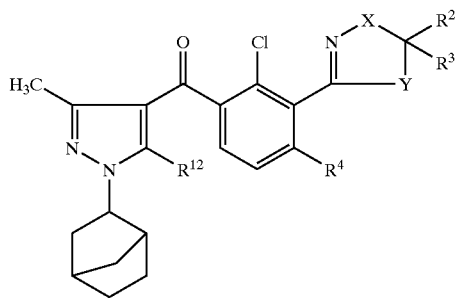

Ia8

Most particular preference is also given to the compounds of the formula Ia9, in particular to the compounds Ia9.1 to Ia9.765 which differ from the compounds Ia1.1 to Ia1.765 in that $R^{13}$ is 2-adamantyl.

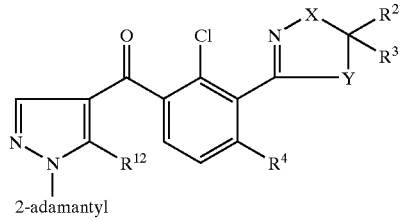

Ia9

Most particular preference is also given to the compounds of the formula Ia10, in particular to the compounds Ia10.1 to Ia10.765 which differ from the compounds Ia1.1 to Ia1.765 in that $R^{13}$ is 2-adamantyl and $R^{14}$ is methyl.

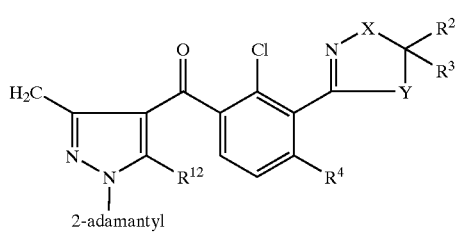

Ia10

Most particular preference is also given to the compounds of the formula Ia11, in particular to the compounds Ia11.1 to Ia11.765 which differ from the corresponding compounds Ia1.1 to Ia1.765 in that $R^1$ is methyl.

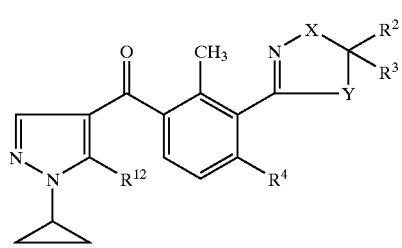

Ia11

Most particular preference is also given to the compounds of the formula Ia12, in particular to the compounds Ia12.1 to Ia12.765 which differ from the corresponding compounds Ia1.1 to Ia1.765 in that $R^1$ is methyl and $R^{14}$ is methyl.

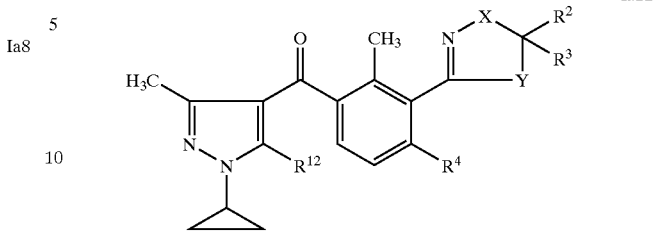

Ia12

Most particular preference is also given to the compounds of the formula Ia13, in particular to the compounds Ia13.1 to Ia13.765 which differ from the compounds Ia1.1 to Ia1.765 in that $R^1$ is methyl and $R^{13}$ is cyclopentyl.

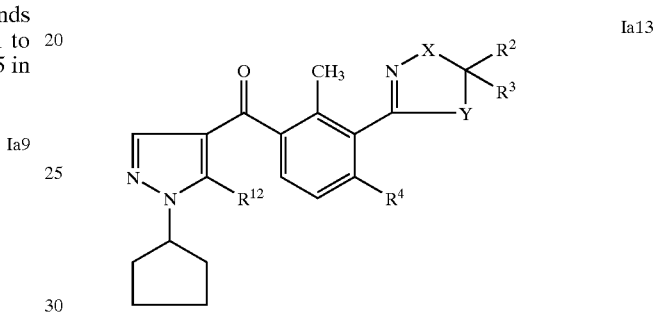

Ia13

Most particular preference is also given to the compounds of the formula Ia14, in particular to the compounds Ia14.1 to Ia14.765 which differ from the compounds Ia1.1 to Ia1.765 in that $R^1$ is methyl, $R^{13}$ is cyclopentyl and $R^{14}$ is methyl.

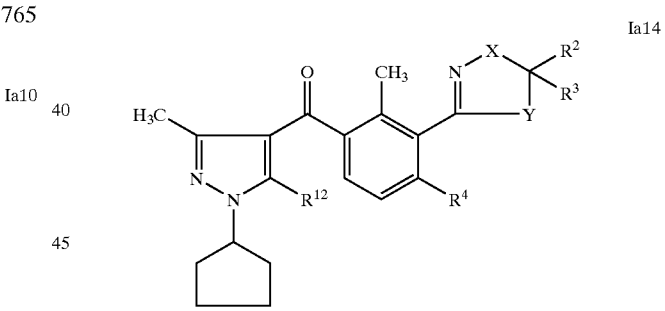

Ia14

Most particular preference is also given to the compounds of the formula Ia15, in particular to the compounds Ia15.1 to Ia15.765 which differ from the compounds Ia1.1 to Ia1.765 in that $R^1$ is methyl and $R^{13}$ is cyclohexyl.

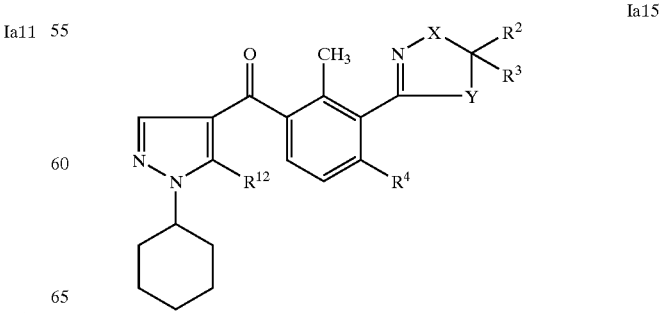

Ia15

Most particular preference is also given to the compounds of the formula Ia16, in particular to the compounds Ia16.1 to Ia16.765 which differ from the compounds Ia1.1 to Ia1.765 in that $R^1$ is methyl, $R^{13}$ is cyclohexyl and $R^{14}$ is methyl.

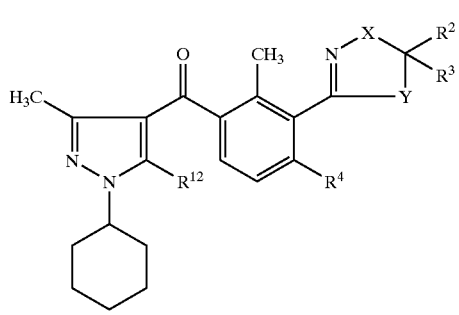

Most particular preference is also given to the compounds of the formula Ia17, in particular to the compounds Ia17.1 to Ia17.765 which differ from the compounds Ia1.1 to Ia1.765 in that $R^1$ is methyl and $R^{13}$ is 2-norbornyl.

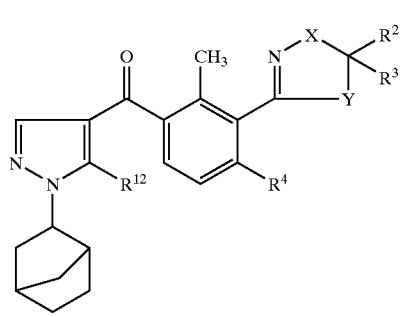

Most particular preference is also given to the compounds of the formula Ia18, in particular to the compounds Ia18.1 to Ia18.765 which differ from the compounds Ia1.1 to Ia1.765 in that $R^1$ is methyl, $R^{12}$ is 2-norbornyl and $R^{14}$ is methyl.

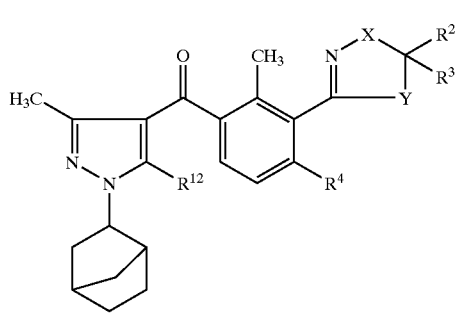

Most particular preference is also given to the compounds of the formula Ia19, in particular to the compounds Ia19.1 to Ia19.765 which differ from the compounds Ia1.1 to Ia1.765 in that $R^1$ is methyl and $R^{13}$ is 2-adamantyl.

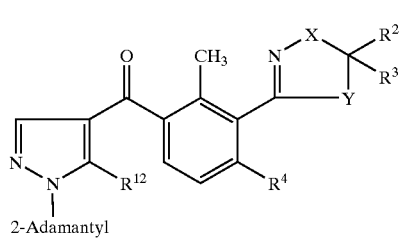

Most particular preference is also given to the compounds of the formula Ia20, in particular to the compounds Ia20.1 to Ia20.765 which differ from the compounds Ia1.1 to Ia1.765 in that $R^1$ is methyl, $R^{13}$ is 2-adamantyl and $R^{14}$ is methyl.

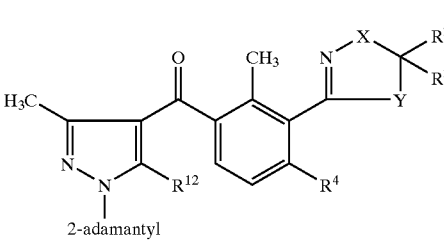

Most particular preference is also given to the compounds of the formula Ia21, in particular to the compounds Ia21.1 to Ia21.765 which differ from the corresponding compounds Ia1.1 to Ia1.765 in that $R^1$ is methoxy.

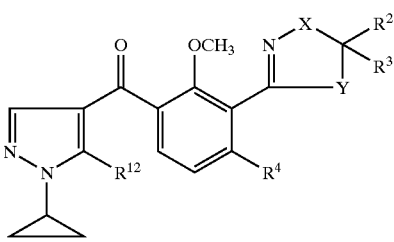

Most particular preference is also given to the compounds of the formula Ia22, in particular to the compounds Ia22.1 to Ia22.765 which differ from the corresponding compounds Ia1.1 to Ia1.765 in that $R^1$ is methoxy and $R^{14}$ is methyl.

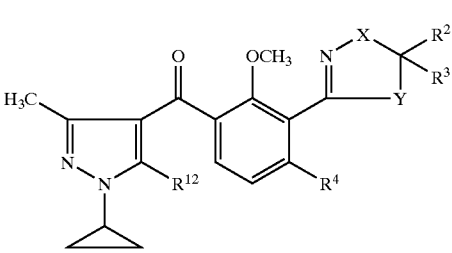

Most particular preference is also given to the compounds of the formula Ia23, in particular to the compounds Ia23.1 to Ia23.765 which differ from the compounds Ia1.1 to Ia1.765 in that $R^1$ is methoxy and $R^{13}$ is cyclopentyl.

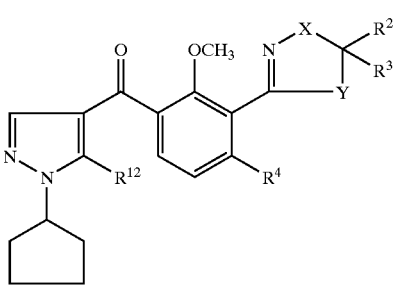

Most particuiar preference is also given to the compounds of the formula Ia24, in particular to the compounds Ia24.1 to Ia24.765 which differ from the compounds Ia1.1 to Ia1.765 in that $R^1$ is methoxy, $R^{13}$ is cyclopentyl and $R^{14}$ is methyl.

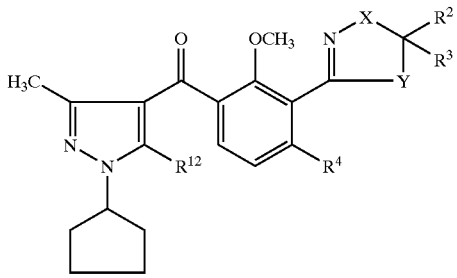

Ia24

Most particular preference is also given to the compounds of the formula Ia25, in particular to the compounds Ia25.1 to Ia25.765 which differ from the compounds Ia1.1 to Ia1.765 in that $R^1$ is methoxy and $R^{13}$ is cyclohexyl.

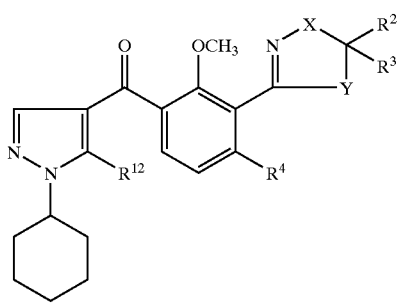

Ia25

Most particular preference is also given to the compounds of the formula Ia26, in particular to the compounds Ia26.1 to Ia26.765 which differ from the compounds Ia1.1 to Ia1.765 in that $R^1$ is methoxy, $R^{13}$ is cyclohexyl and $R^{14}$ is methyl.

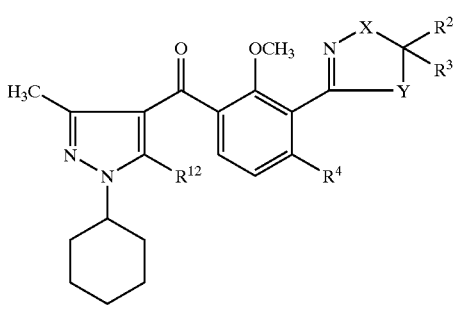

Ia26

Most particular preference is also given to the compounds of the formula Ia27, in particular to the compounds Ia27.1 to Ia27.765 which differ from the compounds Ia1.1 to Ia1.765 in that $R^1$ is methoxy and $R^{13}$ is 2-norbornyl.

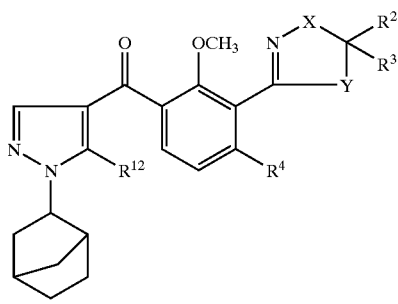

Ia27

Most particular preference is also given to the compounds of the formula Ia28, in particular to the compounds Ia28.1 to Ia28.765 which differ from the compounds Ia1.1 to Ia1.765 in that $R^1$ is methoxy, $R^{13}$ is norbornyl and $R^{14}$ is methyl.

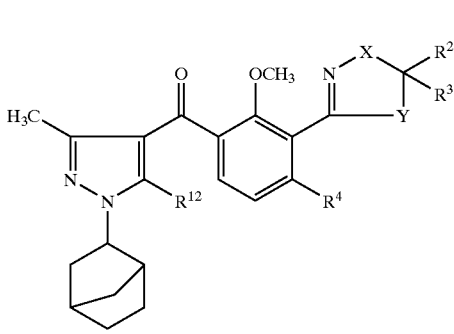

Ia28

Most particular preference is also given to the compounds of the formula Ia29, in particular to the compounds Ia29.1 to Ia29.765 which differ from the compounds Ia1.1 to Ia1.765 in that $R^1$ is methoxy and $R^{13}$ is 2-adamantyl.

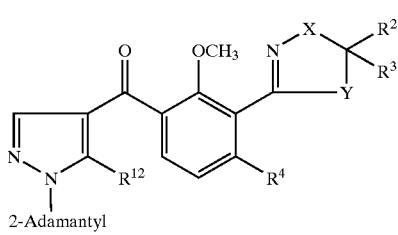

Ia29

Most particular preference is also given to the compounds of the formula Ia30, in particular to the compounds Ia30.1 to Ia30.765 which differ from the compounds Ia1.1 to Ia1.765 in that $R^1$ is methoxy, $R^{13}$ is 2-adamantyl and $R^{14}$ is methyl.

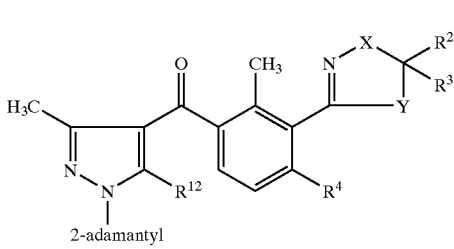

Ia30

Most particular preference is also given to the compounds of the formula Ib1 (=I where $R^1$=Cl, $R^3$ and $R^9$ or $R^3$ and $R^{11}$ together form a bond, $R^{13}$=cyclo-$C_3H_5$ and $R^5$ and $R^{14}$=H), in particular to the compounds Ib1.1 to Ib1.420 of Table 2 where the radical definitions X, Y and $R^1$ to $R^{14}$ are of particular importance for the compounds according to the invention not only in combination with one another but also in each case on their own.

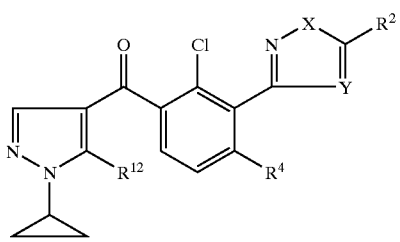

Ib1

TABLE 2

| | X | $R^2$ | Y | $R^4$ | $R^{12}$ |
|---|---|---|---|---|---|
| Ib1.1 | O | H | CH | $SCH_3$ | OH |
| Ib1.2 | O | H | CH | $SCH_2CH_3$ | OH |
| Ib1.3 | O | H | CH | $SO_2CH_3$ | OH |
| Ib1.4 | O | H | CH | $SO_2CH_2CH_3$ | OH |
| Ib1.5 | O | H | CH | $SO_2CH(CH_3)_2$ | OH |
| Ib1.6 | O | H | CH | $SO_2(CH_2)_2CH_3$ | OH |
| Ib1.7 | O | H | CH | Cl | OH |
| Ib1.8 | O | H | CH | Br | OH |
| Ib1.9 | O | H | CH | $NO_2$ | OH |
| Ib1.10 | O | H | CH | $CHF_2$ | OH |
| Ib1.11 | O | H | CH | $CF_3$ | OH |
| Ib1.12 | O | H | CH | $OCH_3$ | OH |
| Ib1.13 | O | H | CH | $OCH_2CH_3$ | OH |
| Ib1.14 | O | H | CH | $OCHF_2$ | OH |
| Ib1.15 | O | H | CH | $OCF_3$ | OH |
| Ib1.16 | O | $CH_3$ | CH | $SCH_3$ | OH |
| Ib1.17 | O | $CH_3$ | CH | $SCH_2CH_3$ | OH |
| Ib1.18 | O | $CH_3$ | CH | $SO_2CH_3$ | OH |
| Ib1.19 | O | $CH_3$ | CH | $SO_2CH_2CH_3$ | OH |
| Ib1.20 | O | $CH_3$ | CH | $SO_2CH(CH_3)_2$ | OH |
| Ib1.21 | O | $CH_3$ | CH | $SO_2(CH_2)_2CH_3$ | OH |
| Ib1.22 | O | $CH_3$ | CH | Cl | OH |
| Ib1.23 | O | $CH_3$ | CH | Br | OH |
| Ib1.24 | O | $CH_3$ | CH | $NO_2$ | OH |
| Ib1.25 | O | $CH_3$ | CH | $CHF_2$ | OH |
| Ib1.26 | O | $CH_3$ | CH | $CF_3$ | OH |
| Ib1.27 | O | $CH_3$ | CH | $OCH_3$ | OH |
| Ib1.28 | O | $CH_3$ | CH | $OCH_2CH_3$ | OH |
| Ib1.29 | O | $CH_3$ | CH | $OCHF_2$ | OH |
| Ib1.30 | O | $CH_3$ | CH | $OCF_3$ | OH |
| Ib1.31 | O | $CH_2CH_3$ | CH | $SCH_3$ | OH |
| Ib1.32 | O | $CH_2CH_3$ | CH | $SCH_2CH_3$ | OH |
| Ib1.33 | O | $CH_2CH_3$ | CH | $SO_2CH_3$ | OH |
| Ib1.34 | O | $CH_2CH_3$ | CH | $SO_2CH_2CH_3$ | OH |
| Ib1.35 | O | $CH_2CH_3$ | CH | $SO_2CH(CH_3)_2$ | OH |
| Ib1.36 | O | $CH_2CH_3$ | CH | $SO_2(CH_2)_2CH_3$ | OH |
| Ib1.37 | O | $CH_2CH_3$ | CH | Cl | OH |
| Ib1.38 | O | $CH_2CH_3$ | CH | Br | OH |
| Ib1.39 | O | $CH_2CH_3$ | CH | $NO_2$ | OH |
| Ib1.40 | O | $CH_2CH_3$ | CH | $CHF_2$ | OH |
| Ib1.41 | O | $CH_2CH_3$ | CH | $CF_3$ | OH |
| Ib1.42 | O | $CH_2CH_3$ | CH | $OCH_3$ | OH |
| Ib1.43 | O | $CH_2CH_3$ | CH | $OCH_2CH_3$ | OH |
| Ib1.44 | O | $CH_2CH_3$ | CH | $OCHF_2$ | OH |
| Ib1.45 | O | $CH_2CH_3$ | CH | $OCF_3$ | OH |
| Ib1.46 | O | $CH_2Cl$ | CH | $SCH_3$ | OH |
| Ib1.47 | O | $CH_2Cl$ | CH | $SCH_2CH_3$ | OH |
| Ib1.48 | O | $CH_2Cl$ | CH | $SO_2CH_3$ | OH |
| Ib1.49 | O | $CH_2Cl$ | CH | $SO_2CH_2CH_3$ | OH |
| Ib1.50 | O | $CH_2Cl$ | CH | $SO_2CH(CH_3)_2$ | OH |
| Ib1.51 | O | $CH_2Cl$ | CH | $SO_2(CH_2)_2CH_3$ | OH |
| Ib1.52 | O | $CH_2Cl$ | CH | Cl | OH |
| Ib1.53 | O | $CH_2Cl$ | CH | Br | OH |
| Ib1.54 | O | $CH_2Cl$ | CH | $NO_2$ | OH |
| Ib1.55 | O | $CH_2Cl$ | CH | $CHF_2$ | OH |
| Ib1.56 | O | $CH_2Cl$ | CH | $CF_3$ | OH |
| Ib1.57 | O | $CH_2Cl$ | CH | $OCH_3$ | OH |
| Ib1.58 | O | $CH_2Cl$ | CH | $OCH_2CH_3$ | OH |
| Ib1.59 | O | $CH_2Cl$ | CH | $OCHF_2$ | OH |
| Ib1.60 | O | $CH_2Cl$ | CH | $OCF_3$ | OH |
| Ib1.61 | O | H | $C(CH_3)$ | $SCH_3$ | OH |
| Ib1.62 | O | H | $C(CH_3)$ | $SCH_2CH_3$ | OH |
| Ib1.63 | O | H | $C(CH_3)$ | $SO_2CH_3$ | OH |
| Ib1.64 | O | H | $C(CH_3)$ | $SO_2CH_2CH_3$ | OH |
| Ib1.65 | O | H | $C(CH_3)$ | $SO_2CH(CH_3)_2$ | OH |
| Ib1.66 | O | H | $C(CH_3)$ | $SO_2(CH_2)_2CH_3$ | OH |
| Ib1.67 | O | H | $C(CH_3)$ | Cl | OH |
| Ib1.68 | O | H | $C(CH_3)$ | Br | OH |
| Ib1.69 | O | H | $C(CH_3)$ | $NO_2$ | OH |
| Ib1.70 | O | H | $C(CH_3)$ | $CHF_2$ | OH |
| Ib1.71 | O | H | $C(CH_3)$ | $CF_3$ | OH |
| Ib1.72 | O | H | $C(CH_3)$ | $OCH_3$ | OH |
| Ib1.73 | O | H | $C(CH_3)$ | $OCH_2CH_3$ | OH |
| Ib1.74 | O | H | $C(CH_3)$ | $OCHF_2$ | OH |
| Ib1.75 | O | H | $C(CH_3)$ | $OCF_3$ | OH |
| Ib1.76 | O | $CH_3$ | $C(CH_3)$ | $SCH_3$ | OH |
| Ib1.77 | O | $CH_3$ | $C(CH_3)$ | $SCH_2CH_3$ | OH |
| Ib1.78 | O | $CH_3$ | $C(CH_3)$ | $SO_2CH_3$ | OH |
| Ib1.79 | O | $CH_3$ | $C(CH_3)$ | $SO_2CH_2CH_3$ | OH |
| Ib1.80 | O | $CH_3$ | $C(CH_3)$ | $SO_2CH(CH_3)_2$ | OH |
| Ib1.81 | O | $CH_3$ | $C(CH_3)$ | $SO_2(CH_2)_2CH_3$ | OH |
| Ib1.82 | O | $CH_3$ | $C(CH_3)$ | Cl | OH |
| Ib1.83 | O | $CH_3$ | $C(CH_3)$ | Br | OH |
| Ib1.84 | O | $CH_3$ | $C(CH_3)$ | $NO_2$ | OH |
| Ib1.85 | O | $CH_3$ | $C(CH_3)$ | $CHF_2$ | OH |
| Ib1.86 | O | $CH_3$ | $C(CH_3)$ | $CF_3$ | OH |
| Ib1.87 | O | $CH_3$ | $C(CH_3)$ | $OCH_3$ | OH |
| Ib1.88 | O | $CH_3$ | $C(CH_3)$ | $OCH_2CH_3$ | OH |
| Ib1.89 | O | $CH_3$ | $C(CH_3)$ | $OCHF_2$ | OH |
| Ib1.90 | O | $CH_3$ | $C(CH_3)$ | $OCF_3$ | OH |
| Ib1.91 | O | $CH_2CH_3$ | $C(CH_3)$ | $SCH_3$ | OH |
| Ib1.92 | O | $CH_2CH_3$ | $C(CH_3)$ | $SCH_2CH_3$ | OH |
| Ib1.93 | O | $CH_2CH_3$ | $C(CH_3)$ | $SO_2CH_3$ | OH |
| Ib1.94 | O | $CH_2CH_3$ | $C(CH_3)$ | $SO_2CH_2CH_3$ | OH |
| Ib1.95 | O | $CH_2CH_3$ | $C(CH_3)$ | $SO_2CH(CH_3)_2$ | OH |
| Ib1.96 | O | $CH_2CH_3$ | $C(CH_3)$ | $SO_2(CH_2)_2CH_3$ | OH |
| Ib1.97 | O | $CH_2CH_3$ | $C(CH_3)$ | Cl | OH |
| Ib1.98 | O | $CH_2CH_3$ | $C(CH_3)$ | Br | OH |
| Ib1.99 | O | $CH_2CH_3$ | $C(CH_3)$ | $NO_2$ | OH |
| Ib1.100 | O | $CH_2CH_3$ | $C(CH_3)$ | $CHF_2$ | OH |
| Ib1.101 | O | $CH_2CH_3$ | $C(CH_3)$ | $CF_3$ | OH |
| Ib1.102 | O | $CH_2CH_3$ | $C(CH_3)$ | $OCH_3$ | OH |
| Ib1.103 | O | $CH_2CH_3$ | $C(CH_3)$ | $OCH_2CH_3$ | OH |
| Ib1.104 | O | $CH_2CH_3$ | $C(CH_3)$ | $OCHF_2$ | OH |
| Ib1.105 | O | $CH_2CH_3$ | $C(CH_3)$ | $OCF_3$ | OH |
| Ib1.106 | O | $CH_2Cl$ | $C(CH_3)$ | $SCH_3$ | OH |
| Ib1.107 | O | $CH_2Cl$ | $C(CH_3)$ | $SCH_2CH_3$ | OH |
| Ib1.108 | O | $CH_2Cl$ | $C(CH_3)$ | $SO_2CH_3$ | OH |
| Ib1.109 | O | $CH_2Cl$ | $C(CH_3)$ | $SO_2CH_2CH_3$ | OH |
| Ib1.110 | O | $CH_2Cl$ | $C(CH_3)$ | $SO_2CH(CH_3)_2$ | OH |
| Ib1.111 | O | $CH_2Cl$ | $C(CH_3)$ | $SO_2(CH_2)_2CH_3$ | OH |
| Ib1.112 | O | $CH_2Cl$ | $C(CH_3)$ | Cl | OH |
| Ib1.113 | O | $CH_2Cl$ | $C(CH_3)$ | Br | OH |
| Ib1.114 | O | $CH_2Cl$ | $C(CH_3)$ | $NO_2$ | OH |
| Ib1.115 | O | $CH_2Cl$ | $C(CH_3)$ | $CHF_2$ | OH |
| Ib1.116 | O | $CH_2Cl$ | $C(CH_3)$ | $CF_3$ | OH |
| Ib1.117 | O | $CH_2Cl$ | $C(CH_3)$ | $OCH_3$ | OH |
| Ib1.118 | O | $CH_2Cl$ | $C(CH_3)$ | $OCH_2CH_3$ | OH |
| Ib1.119 | O | $CH_2Cl$ | $C(CH_3)$ | $OCHF_2$ | OH |
| Ib1.120 | O | $CH_2Cl$ | $C(CH_3)$ | $OCF_3$ | OH |
| Ib1.121 | O | H | $C(CH_2CH_3)$ | $SCH_3$ | OH |
| Ib1.122 | O | H | $C(CH_2CH_3)$ | $SCH_2CH_3$ | OH |
| Ib1.123 | O | H | $C(CH_2CH_3)$ | $SO_2CH_3$ | OH |
| Ib1.124 | O | H | $C(CH_2CH_3)$ | $SO_2CH_2CH_3$ | OH |
| Ib1.125 | O | H | $C(CH_2CH_3)$ | $SO_2CH(CH_3)_2$ | OH |
| Ib1.126 | O | H | $C(CH_2CH_3)$ | $SO_2(CH_2)_2CH_3$ | OH |
| Ib1.127 | O | H | $C(CH_2CH_3)$ | Cl | OH |
| Ib1.128 | O | H | $C(CH_2CH_3)$ | Br | OH |
| Ib1.129 | O | H | $C(CH_2CH_3)$ | $NO_2$ | OH |

TABLE 2-continued

| | X | R² | Y | R⁴ | R¹² |
|---|---|---|---|---|---|
| Ib1.130 | O | H | C(CH₂CH₃) | CHF₂ | OH |
| Ib1.131 | O | H | C(CH₂CH₃) | CF₃ | OH |
| Ib1.132 | O | H | C(CH₂CH₃) | OCH₃ | OH |
| Ib1.133 | O | H | C(CH₂CH₃) | OCH₂CH₃ | OH |
| Ib1.134 | O | H | C(CH₂CH₃) | OCHF₂ | OH |
| Ib1.135 | O | H | C(CH₂CH₃) | OCF₃ | OH |
| Ib1.136 | O | CH₃ | C(CH₂CH₃) | SCH₃ | OH |
| Ib1.137 | O | CH₃ | C(CH₂CH₃) | SCH₂CH₃ | OH |
| Ib1.138 | O | CH₃ | C(CH₂CH₃) | SO₂CH₃ | OH |
| Ib1.139 | O | CH₃ | C(CH₂CH₃) | SO₂CH₂CH₃ | OH |
| Ib1.140 | O | CH₃ | C(CH₂CH₃) | SO₂CH(CH₃)₂ | OH |
| Ib1.141 | O | CH₃ | C(CH₂CH₃) | SO₂(CH₂)₂CH₃ | OH |
| Ib1.142 | O | CH₃ | C(CH₂CH₃) | Cl | OH |
| Ib1.143 | O | CH₃ | C(CH₂CH₃) | Br | OH |
| Ib1.144 | O | CH₃ | C(CH₂CH₃) | NO₂ | OH |
| Ib1.145 | O | CH₃ | C(CH₂CH₃) | CHF₂ | OH |
| Ib1.146 | O | CH₃ | C(CH₂CH₃) | CF₃ | OH |
| Ib1.147 | O | CH₃ | C(CH₂CH₃) | OCH₃ | OH |
| Ib1.148 | O | CH₃ | C(CH₂CH₃) | OCH₂CH₃ | OH |
| Ib1.149 | O | CH₃ | C(CH₂CH₃) | OCHF₂ | OH |
| Ib1.150 | O | CH₃ | C(CH₂CH₃) | OCF₃ | OH |
| Ib1.151 | O | CH₂CH₃ | C(CH₂CH₃) | SCH₃ | OH |
| Ib1.152 | O | CH₂CH₃ | C(CH₂CH₃) | SCH₂CH₃ | OH |
| Ib1.153 | O | CH₂CH₃ | C(CH₂CH₃) | SO₂CH₃ | OH |
| Ib1.154 | O | CH₂CH₃ | C(CH₂CH₃) | SO₂CH₂CH₃ | OH |
| Ib1.155 | O | CH₂CH₃ | C(CH₂CH₃) | SO₂CH(CH₃)₂ | OH |
| Ib1.156 | O | CH₂CH₃ | C(CH₂CH₃) | SO₂(CH₂)₂CH₃ | OH |
| Ib1.157 | O | CH₂CH₃ | C(CH₂CH₃) | Cl | OH |
| Ib1.158 | O | CH₂CH₃ | C(CH₂CH₃) | Br | OH |
| Ib1.159 | O | CH₂CH₃ | C(CH₂CH₃) | NO₂ | OH |
| Ib1.160 | O | CH₂CH₃ | C(CH₂CH₃) | CHF₂ | OH |
| Ib1.161 | O | CH₂CH₃ | C(CH₂CH₃) | CF₃ | OH |
| Ib1.162 | O | CH₂CH₃ | C(CH₂CH₃) | OCH₃ | OH |
| Ib1.163 | O | CH₂CH₃ | C(CH₂CH₃) | OCH₂CH₃ | OH |
| Ib1.164 | O | CH₂CH₃ | C(CH₂CH₃) | OCHF₂ | OH |
| Ib1.165 | O | CH₂CH₃ | C(CH₂CH₃) | OCF₃ | OH |
| Ib1.166 | O | CH₂Cl | C(CH₂CH₃) | SCH₃ | OH |
| Ib1.167 | O | CH₂Cl | C(CH₂CH₃) | SCH₂CH₃ | OH |
| Ib1.168 | O | CH₂Cl | C(CH₂CH₃) | SO₂CH₃ | OH |
| Ib1.169 | O | CH₂Cl | C(CH₂CH₃) | SO₂CH₂CH₃ | OH |
| Ib1.170 | O | CH₂Cl | C(CH₂CH₃) | SO₂CH(CH₃)₂ | OH |
| Ib1.171 | O | CH₂Cl | C(CH₂CH₃) | SO₂(CH₂)₂CH₃ | OH |
| Ib1.172 | O | CH₂Cl | C(CH₂CH₃) | Cl | OH |
| Ib1.173 | O | CH₂Cl | C(CH₂CH₃) | Br | OH |
| Ib1.174 | O | CH₂Cl | C(CH₂CH₃) | NO₃ | OH |
| Ib1.175 | O | CH₂Cl | C(CH₂CH₃) | CHF₂ | OH |
| Ib1.176 | O | CH₂Cl | C(CH₂CH₃) | CF₃ | OH |
| Ib1.177 | O | CH₂Cl | C(CH₂CH₃) | OCH₃ | OH |
| Ib1.178 | O | CH₂Cl | C(CH₂CH₃) | OCH₂CH₃ | OH |
| Ib1.179 | O | CH₂Cl | C(CH₂CH₃) | OCHF₂ | OH |
| Ib1.180 | O | CH₂Cl | C(CH₂CH₃) | OCF₃ | OH |
| Ib1.181 | NCH₃ | H | CH | SCH₃ | OH |
| Ib1.182 | NCH₃ | H | CH | SCH₂CH₃ | OH |
| Ib1.183 | NCH₃ | H | CH | SO₂CH₃ | OH |
| Ib1.184 | NCH₃ | H | CH | SO₂CH₂CH₃ | OH |
| Ib1.185 | NCH₃ | H | CH | SO₂CH(CH₃)₂ | OH |
| Ib1.186 | NCH₃ | H | CH | SO₂(CH₂)₂CH₃ | OH |
| Ib1.187 | NCH₃ | H | CH | Cl | OH |
| Ib1.188 | NCH₃ | H | CH | Br | OH |
| Ib1.189 | NCH₃ | H | CH | NO₂ | OH |
| Ib1.190 | NCH₃ | H | CH | CHF₂ | OH |
| Ib1.191 | NCH₃ | H | CH | CF₃ | OH |
| Ib1.192 | NCH₃ | H | CH | OCH₃ | OH |
| Ib1.193 | NCH₃ | H | CH | OCH₂CH₃ | OH |
| Ib1.194 | NCH₃ | H | CH | OCHF₂ | OH |
| Ib1.195 | NCH₃ | H | CH | OCF₃ | OH |
| Ib1.196 | NCH₃ | CH₃ | CH | SCH₃ | OH |
| Ib1.197 | NCH₃ | CH₃ | CH | SCH₂CH₃ | OH |
| Ib1.198 | NCH₃ | CH₃ | CH | SO₂CH₃ | OH |
| Ib1.199 | NCH₃ | CH₃ | CH | SO₂CH₂CH₃ | OH |
| Ib1.200 | NCH₃ | CH₃ | CH | SO₂CH(CH₃)₂ | OH |
| Ib1.201 | NCH₃ | CH₃ | CH | SO₂(CH₂)₂CH₃ | OH |
| Ib1.202 | NCH₃ | CH₃ | CH | Cl | OH |
| Ib1.203 | NCH₃ | CH₃ | CH | Br | OH |
| Ib1.204 | NCH₃ | CH₃ | CH | NO₂ | OH |
| Ib1.205 | NCH₃ | CH₃ | CH | CHF₂ | OH |
| Ib1.206 | NCH₃ | CH₃ | CH | CF₃ | OH |
| Ib1.207 | NCH₃ | CH₃ | CH | OCH₃ | OH |
| Ib1.208 | NCH₃ | CH₃ | CH | OCH₂CH₃ | OH |
| Ib1.209 | NCH₃ | CH₃ | CH | OCHF₂ | OH |
| Ib1.210 | NCH₃ | CH₃ | CH | OCF₃ | OH |
| Ib1.211 | NCH₃ | CH₂CH₃ | CH | SCH₃ | OH |
| Ib1.212 | NCH₃ | CH₂CH₃ | CH | SCH₂CH₃ | OH |
| Ib1.213 | NCH₃ | CH₂CH₃ | CH | SO₂CH₃ | OH |
| Ib1.214 | NCH₃ | CH₂CH₃ | CH | SO₂CH₂CH₃ | OH |
| Ib1.215 | NCH₃ | CH₂CH₃ | CH | SO₂CH(CH₃)₂ | OH |
| Ib1.216 | NCH₃ | CH₂CH₃ | CH | SO₂(CH₂)₂CH₃ | OH |
| Ib1.217 | NCH₃ | CH₂CH₃ | CH | Cl | OH |
| Ib1.218 | NCH₃ | CH₂CH₃ | CH | Br | OH |
| Ib1.219 | NCH₃ | CH₂CH₃ | CH | NO₂ | OH |
| Ib1.220 | NCH₃ | CH₂CH₃ | CH | CHF₂ | OH |
| Ib1.221 | NCH₃ | CH₂CH₃ | CH | CF₃ | OH |
| Ib1.222 | NCH₃ | CH₂CH₃ | CH | OCH₃ | OH |
| Ib1.223 | NCH₃ | CH₂CH₃ | CH | OCH₂CH₃ | OH |
| Ib1.224 | NCH₃ | CH₂CH₃ | CH | OCHF₂ | OH |
| Ib1.225 | NCH₃ | CH₂CH₃ | CH | OCF₃ | OH |
| Ib1.226 | NCH₃ | CH₂Cl | CH | SCH₃ | OH |
| Ib1.227 | NCH₃ | CH₂Cl | CH | SCH₂CH₃ | OH |
| Ib1.228 | NCH₃ | CH₂Cl | CH | SO₂CH₃ | OH |
| Ib1.229 | NCH₃ | CH₂Cl | CH | SO₂CH₂CH₃ | OH |
| Ib1.230 | NCH₃ | CH₂Cl | CH | SO₂CH(CH₃)₂ | OH |
| Ib1.231 | NCH₃ | CH₂Cl | CH | SO₂(CH₂)₂CH₃ | OH |
| Ib1.232 | NCH₃ | CH₂Cl | CH | Cl | OH |
| Ib1.233 | NCH₃ | CH₂Cl | CH | Br | OH |
| Ib1.234 | NCH₃ | CH₂Cl | CH | NO₂ | OH |
| Ib1.235 | NCH₃ | CH₂Cl | CH | CHF₂ | OH |
| Ib1.236 | NCH₃ | CH₂Cl | CH | CF₃ | OH |
| Ib1.237 | NCH₃ | CH₂Cl | CH | OCH₃ | OH |
| Ib1.238 | NCH₃ | CH₂Cl | CH | OCH₂CH₃ | OH |
| Ib1.239 | NCH₃ | CH₂Cl | CH | OCHF₂ | OH |
| Ib1.240 | NCH₃ | CH₂Cl | CH | OCF₃ | OH |
| Ib1.241 | NCH₃ | H | C(CH₃) | SCH₃ | OH |
| Ib1.242 | NCH₃ | H | C(CH₃) | SCH₂CH₃ | OH |
| Ib1.243 | NCH₃ | H | C(CH₃) | SO₂CH₃ | OH |
| Ib1.244 | NCH₃ | H | C(CH₃) | SO₂CH₂CH₃ | OH |
| Ib1.245 | NCH₃ | H | C(CH₃) | SO₂CH(CH₃)₂ | OH |
| Ib1.246 | NCH₃ | H | C(CH₃) | SO₂(CH₂)₂CH₃ | OH |
| Ib1.247 | NCH₃ | H | C(CH₃) | Cl | OH |
| Ib1.248 | NCH₃ | H | C(CH₃) | Br | OH |
| Ib1.249 | NCH₃ | H | C(CH₃) | NO₂ | OH |
| Ib1.250 | NCH₃ | H | C(CH₃) | CHF₂ | OH |
| Ib1.251 | NCH₃ | H | C(CH₃) | CF₃ | OH |
| Ib1.252 | NCH₃ | H | C(CH₃) | OCH₃ | OH |
| Ib1.253 | NCH₃ | H | C(CH₃) | OCH₂CH₃ | OH |
| Ib1.254 | NCH₃ | H | C(CH₃) | OCHF₂ | OH |
| Ib1.255 | NCH₃ | H | C(CH₃) | OCF₃ | OH |
| Ib1.256 | NCH₃ | CH₃ | C(CH₃) | SCH₃ | OH |
| Ib1.257 | NCH₃ | CH₃ | C(CH₃) | SCH₂CH₃ | OH |
| Ib1.258 | NCH₃ | CH₃ | C(CH₃) | SO₂CH₃ | OH |
| Ib1.259 | NCH₃ | CH₃ | C(CH₃) | SO₂CH₂CH₃ | OH |
| Ib1.260 | NCH₃ | CH₃ | C(CH₃) | SO₂CH(CH₃)₂ | OH |
| Ib1.261 | NCH₃ | CH₃ | C(CH₃) | SO₂(CH₂)₂CH₃ | OH |
| Ib1.262 | NCH₃ | CH₃ | C(CH₃) | Cl | OH |
| Ib1.263 | NCH₃ | CH₃ | C(CH₃) | Br | OH |
| Ib1.264 | NCH₃ | CH₃ | C(CH₃) | NO₂ | OH |
| Ib1.265 | NCH₃ | CH₃ | C(CH₃) | CHF₂ | OH |
| Ib1.266 | NCH₃ | CH₃ | C(CH₃) | CF₃ | OH |
| Ib1.267 | NCH₃ | CH₃ | C(CH₃) | OCH₃ | OH |
| Ib1.268 | NCH₃ | CH₃ | C(CH₃) | OCH₂CH₃ | OH |
| Ib1.269 | NCH₃ | CH₃ | C(CH₃) | OCHF₂ | OH |
| Ib1.270 | NCH₃ | CH₃ | C(CH₃) | OCF₃ | OH |
| Ib1.271 | NCH₃ | CH₂CH₃ | C(CH₃) | SCH₃ | OH |
| Ib1.272 | NCH₃ | CH₂CH₃ | C(CH₃) | SCH₂CH₃ | OH |
| Ib1.273 | NCH₃ | CH₂CH₃ | C(CH₃) | SO₂CH₃ | OH |
| Ib1.274 | NCH₃ | CH₂CH₃ | C(CH₃) | SO₂CH₂CH₃ | OH |
| Ib1.275 | NCH₃ | CH₂CH₃ | C(CH₃) | SO₂CH(CH₃)₂ | OH |
| Ib1.276 | NCH₃ | CH₂CH₃ | C(CH₃) | SO₂(CH₂)₂CH₃ | OH |
| Ib1.277 | NCH₃ | CH₂CH₃ | C(CH₃) | Cl | OH |
| Ib1.278 | NCH₃ | CH₂CH₃ | C(CH₃) | Br | OH |
| Ib1.279 | NCH₃ | CH₂CH₃ | C(CH₃) | NO₂ | OH |
| Ib1.280 | NCH₃ | CH₂CH₃ | C(CH₃) | CHF₂ | OH |
| Ib1.281 | NCH₃ | CH₂CH₃ | C(CH₃) | CF₃ | OH |
| Ib1.282 | NCH₃ | CH₂CH₃ | C(CH₃) | OCH₃ | OH |
| Ib1.283 | NCH₃ | CH₂CH₃ | C(CH₃) | OCH₂CH₃ | OH |

TABLE 2-continued

| | X | R² | Y | R⁴ | R¹² |
|---|---|---|---|---|---|
| Ib1.284 | NCH₃ | CH₂CH₃ | C(CH₃) | OCHF₂ | OH |
| Ib1.285 | NCH₃ | CH₂CH₃ | C(CH₃) | OCF₃ | OH |
| Ib1.286 | NCH₃ | CH₂CH₃ | C(CH₃) | SCH₃ | OH |
| Ib1.287 | NCH₃ | CH₂Cl | C(CH₃) | SCH₂CH₃ | OH |
| Ib1.288 | NCH₃ | CH₂Cl | C(CH₃) | SO₂CH₃ | OH |
| Ib1.289 | NCH₃ | CH₂Cl | C(CH₃) | SO₂CH₂CH₃ | OH |
| Ib1.290 | NCH₃ | CH₂Cl | C(CH₃) | SO₂CH(CH₃)₂ | OH |
| Ib1.291 | NCH₃ | CH₂Cl | C(CH₃) | SO₂(CH₂)₂CH₃ | OH |
| Ib1.292 | NCH₃ | CH₂Cl | C(CH₃) | Cl | OH |
| Ib1.293 | NCH₃ | CH₂Cl | C(CH₃) | Br | OH |
| Ib1.294 | NCH₃ | CH₂Cl | C(CH₃) | NO₂ | OH |
| Ib1.295 | NCH₃ | CH₂Cl | C(CH₃) | CHF₂ | OH |
| Ib1.296 | NCH₃ | CH₂Cl | C(CH₃) | CF₃ | OH |
| Ib1.297 | NCH₃ | CH₂Cl | C(CH₃) | OCH₃ | OH |
| Ib1.298 | NCH₃ | CH₂Cl | C(CH₃) | OCH₂CH₃ | OH |
| Ib1.299 | NCH₃ | CH₂Cl | C(CH₃) | OCHF₂ | OH |
| Ib1.300 | NCH₃ | CH₂Cl | C(CH₃) | OCF₃ | OH |
| Ib1.301 | NCH₃ | H | C(CH₂CH₃) | SCH₃ | OH |
| Ib1.302 | NCH₃ | H | C(CH₂CH₃) | SCH₂CH₃ | OH |
| Ib1.303 | NCH₃ | H | C(CH₂CH₃) | SO₂CH₃ | OH |
| Ib1.304 | NCH₃ | H | C(CH₂CH₃) | SO₂CH₂CH₃ | OH |
| Ib1.305 | NCH₃ | H | C(CH₂CH₃) | SO₂CH(CH₃)₂ | OH |
| Ib1.306 | NCH₃ | H | C(CH₂CH₃) | SO₂(CH₂)₂CH₃ | OH |
| Ib1.307 | NCH₃ | H | C(CH₂CH₃) | Cl | OH |
| Ib1.308 | NCH₃ | H | C(CH₂CH₃) | Br | OH |
| Ib1.309 | NCH₃ | H | C(CH₂CH₃) | NO₂ | OH |
| Ib1.310 | NCH₃ | H | C(CH₂CH₃) | CHF₂ | OH |
| Ib1.311 | NCH₃ | H | C(CH₂CH₃) | CF₃ | OH |
| Ib1.312 | NCH₃ | H | C(CH₂CH₃) | OCH₃ | OH |
| Ib1.313 | NCH₃ | H | C(CH₂CH₃) | OCH₂CH₃ | OH |
| Ib1.314 | NCH₃ | H | C(CH₂CH₃) | OCHF₂ | OH |
| Ib1.315 | NCH₃ | H | C(CH₂CH₃) | OCF₃ | OH |
| Ib1.316 | NCH₃ | CH₃ | C(CH₂CH₃) | SCH₃ | OH |
| Ib1.317 | NCH₃ | CH₃ | C(CH₂CH₃) | SCH₂CH₃ | OH |
| Ib1.318 | NCH₃ | CH₃ | C(CH₂CH₃) | SO₂CH₃ | OH |
| Ib1.319 | NCH₃ | CH₃ | C(CH₂CH₃) | SO₂CH₂CH₃ | OH |
| Ib1.320 | NCH₃ | CH₃ | C(CH₂CH₃) | SO₂CH(CH₃)₂ | OH |
| Ib1.321 | NCH₃ | CH₃ | C(CH₂CH₃) | SO₂(CH₂)₂CH₃ | OH |
| Ib1.322 | NCH₃ | CH₃ | C(CH₂CH₃) | Cl | OH |
| Ib1.323 | NCH₃ | CH₃ | C(CH₂CH₃) | Br | OH |
| Ib1.324 | NCH₃ | CH₃ | C(CH₂CH₃) | NO₂ | OH |
| Ib1.325 | NCH₃ | CH₃ | C(CH₂CH₃) | CHF₂ | OH |
| Ib1.326 | NCH₃ | CH₃ | C(CH₂CH₃) | CF₃ | OH |
| Ib1.327 | NCH₃ | CH₃ | C(CH₂CH₃) | OCH₃ | OH |
| Ib1.328 | NCH₃ | CH₃ | C(CH₂CH₃) | OCH₂CH₃ | OH |
| Ib1.329 | NCH₃ | CH₃ | C(CH₂CH₃) | OCHF₂ | OH |
| Ib1.330 | NCH₃ | CH₃ | C(CH₂CH₃) | OCF₃ | OH |
| Ib1.331 | NCH₃ | CH₂CH₃ | C(CH₂CH₃) | SCH₃ | OH |
| Ib1.332 | NCH₃ | CH₂CH₃ | C(CH₂CH₃) | SCH₂CH₃ | OH |
| Ib1.333 | NCH₃ | CH₂CH₃ | C(CH₂CH₃) | SO₂CH₃ | OH |
| Ib1.334 | NCH₃ | CH₂CH₃ | C(CH₂CH₃) | SO₂CH₂CH₃ | OH |
| Ib1.335 | NCH₃ | CH₂CH₃ | C(CH₂CH₃) | SO₂CH(CH₃)₂ | OH |
| Ib1.336 | NCH₃ | CH₂CH₃ | C(CH₂CH₃) | SO₂(CH₂)₂CH₃ | OH |
| Ib1.337 | NCH₃ | CH₂CH₃ | C(CH₂CH₃) | Cl | OH |
| Ib1.338 | NCH₃ | CH₂CH₃ | C(CH₂CH₃) | Br | OH |
| Ib1.339 | NCH₃ | CH₂CH₃ | C(CH₂CH₃) | NO₂ | OH |
| Ib1.340 | NCH₃ | CH₂CH₃ | C(CH₂CH₃) | CHF₂ | OH |
| Ib1.341 | NCH₃ | CH₂CH₃ | C(CH₂CH₃) | CF₃ | OH |
| Ib1.342 | NCH₃ | CH₂CH₃ | C(CH₂CH₃) | OCH₃ | OH |
| Ib1.343 | NCH₃ | CH₂CH₃ | C(CH₂CH₃) | OCH₂CH₃ | OH |
| Ib1.344 | NCH₃ | CH₂CH₃ | C(CH₂CH₃) | OCHF₂ | OH |
| Ib1.345 | NCH₃ | CH₂CH₃ | C(CH₂CH₃) | OCF₃ | OH |
| Ib1.346 | NCH₃ | CH₂Cl | C(CH₂CH₃) | SCH₃ | OH |
| Ib1.347 | NCH₃ | CH₂Cl | C(CH₂CH₃) | SCH₂CH₃ | OH |
| Ib1.348 | NCH₃ | CH₂Cl | C(CH₂CH₃) | SO₂CH₃ | OH |
| Ib1.349 | NCH₃ | CH₂Cl | C(CH₂CH₃) | SO₂CH₂CH₃ | OH |
| Ib1.350 | NCH₃ | CH₂Cl | C(CH₂CH₃) | SO₂CH(CH₃)₂ | OH |
| Ib1.351 | NCH₃ | CH₂Cl | C(CH₂CH₃) | SO₂(CH₂)₂CH₃ | OH |
| Ib1.352 | NCH₃ | CH₂Cl | C(CH₂CH₃) | Cl | OH |
| Ib1.353 | NCH₃ | CH₂Cl | C(CH₂CH₃) | Br | OH |
| Ib1.354 | NCH₃ | CH₂Cl | C(CH₂CH₃) | NO₂ | OH |
| Ib1.355 | NCH₃ | CH₂Cl | C(CH₂CH₃) | CHF₂ | OH |
| Ib1.356 | NCH₃ | CH₂Cl | C(CH₂CH₃) | CF₃ | OH |
| Ib1.357 | NCH₃ | CH₂Cl | C(CH₂CH₃) | OCH₃ | OH |
| Ib1.358 | NCH₃ | CH₂Cl | C(CH₂CH₃) | OCH₂CH₃ | OH |
| Ib1.359 | NCH₃ | CH₂Cl | C(CH₂CH₃) | OCHF₂ | OH |
| Ib1.360 | NCH₃ | CH₂Cl | C(CH₂CH₃) | OCF₃ | OH |
| Ib1.361 | NCH₃ | H | N | SCH₃ | OH |
| Ib1.362 | NCH₃ | H | N | SCH₂CH₃ | OH |
| Ib1.363 | NCH₃ | H | N | SO₂CH₃ | OH |
| Ib1.364 | NCH₃ | H | N | SO₂CH₂CH₃ | OH |
| Ib1.365 | NCH₃ | H | N | SO₂CH(CH₃)₂ | OH |
| Ib1.366 | NCH₃ | H | N | SO₂(CH₂)₂CH₃ | OH |
| Ib1.367 | NCH₃ | H | N | Cl | OH |
| Ib1.368 | NCH₃ | H | N | Br | OH |
| Ib1.369 | NCH₃ | H | N | NO₂ | OH |
| Ib1.370 | NCH₃ | H | N | CHF₂ | OH |
| Ib1.371 | NCH₃ | H | N | CF₃ | OH |
| Ib1.372 | NCH₃ | H | N | OCH₃ | OH |
| Ib1.373 | NCH₃ | H | N | OCH₂CH₃ | OH |
| Ib1.374 | NCH₃ | H | N | OCHF₂ | OH |
| Ib1.375 | NCH₃ | H | N | OCF₃ | OH |
| Ib1.376 | NCH₃ | CH₃ | N | SCH₃ | OH |
| Ib1.377 | NCH₃ | CH₃ | N | SCH₂CH₃ | OH |
| Ib1.378 | NCH₃ | CH₃ | N | SO₂CH₃ | OH |
| Ib1.379 | NCH₃ | CH₃ | N | SO₂CH₂CH₃ | OH |
| Ib1.380 | NCH₃ | CH₃ | N | SO₂CH(CH₃)₂ | OH |
| Ib1.381 | NCH₃ | CH₃ | N | SO₂(CH₂)₂CH₃ | OH |
| Ib1.382 | NCH₃ | CH₃ | N | Cl | OH |
| Ib1.383 | NCH₃ | CH₃ | N | Br | OH |
| Ib1.384 | NCH₃ | CH₃ | N | NO₂ | OH |
| Ib1.385 | NCH₃ | CH₃ | N | CHF₂ | OH |
| Ib1.386 | NCH₃ | CH₃ | N | CF₃ | OH |
| Ib1.387 | NCH₃ | CH₃ | N | OCH₃ | OH |
| Ib1.388 | NCH₃ | CH₃ | N | OCH₂CH₃ | OH |
| Ib1.389 | NCH₃ | CH₃ | N | OCHF₂ | OH |
| Ib1.390 | NCH₃ | CH₃ | N | OCF₃ | OH |
| Ib1.391 | NCH₃ | CH₂CH₃ | N | SCH₃ | OH |
| Ib1.392 | NCH₃ | CH₂CH₃ | N | SCH₂CH₃ | OH |
| Ib1.393 | NCH₃ | CH₂CH₃ | N | SO₂CH₃ | OH |
| Ib1.394 | NCH₃ | CH₂CH₃ | N | SO₂CH₂CH₃ | OH |
| Ib1.395 | NCH₃ | CH₂CH₃ | N | SO₂CH(CH₃)₂ | OH |
| Ib1.396 | NCH₃ | CH₂CH₃ | N | SO₂(CH₂)₂CH₃ | OH |
| Ib1.397 | NCH₃ | CH₂CH₃ | N | Cl | OH |
| Ib1.398 | NCH₃ | CH₂CH₃ | N | Br | OH |
| Ib1.399 | NCH₃ | CH₂CH₃ | N | NO₃ | OH |
| Ib1.400 | NCH₃ | CH₂CH₃ | N | CHF₂ | OH |
| Ib1.401 | NCH₃ | CH₂CH₃ | N | CF₃ | OH |
| Ib1.402 | NCH₃ | CH₂CH₃ | N | OCH₃ | OH |
| Ib1.403 | NCH₃ | CH₂CH₃ | N | OCH₂CH₃ | OH |
| Ib1.404 | NCH₃ | CH₂CH₃ | N | OCHF₂ | OH |
| Ib1.405 | NCH₃ | CH₂CH₃ | N | OCF₃ | OH |
| Ib1.406 | NCH₃ | CH₂Cl | N | SCH₃ | OH |
| Ib1.407 | NCH₃ | CH₂Cl | N | SCH₂CH₃ | OH |
| Ib1.408 | NCH₃ | CH₂Cl | N | SO₂CH₃ | OH |
| Ib1.409 | NCH₃ | CH₂Cl | N | SO₂CH₂CH₃ | OH |
| Ib1.410 | NCH₃ | CH₂Cl | N | SO₂CH(CH₃)₂ | OH |
| Ib1.411 | NCH₃ | CH₂Cl | N | SO₂(CH₂)₂CH₃ | OH |
| Ib1.412 | NCH₃ | CH₂Cl | N | Cl | OH |
| Ib1.413 | NCH₃ | CH₂Cl | N | Br | OH |
| Ib1.414 | NCH₃ | CH₂Cl | N | NO₂ | OH |
| Ib1.415 | NCH₃ | CH₂Cl | N | CHF₂ | OH |
| Ib1.416 | NCH₃ | CH₂Cl | N | CF₃ | OH |
| Ib1.417 | NCH₃ | CH₂Cl | N | OCH₃ | OH |
| Ib1.418 | NCH₃ | CH₂Cl | N | OCH₂CH₃ | OH |
| Ib1.419 | NCH₃ | CH₂Cl | N | OCHF₂ | OH |
| Ib1.420 | NCH₃ | CH₂Cl | N | OCF₃ | OH |

Most particular preference is also given to the compounds of the formula Ib2, in particular to the compounds Ib2.1 to Ib2.420 which differ from the corresponding compounds Ib1.1 to Ib1.420 in that $R^{14}$ is methyl.

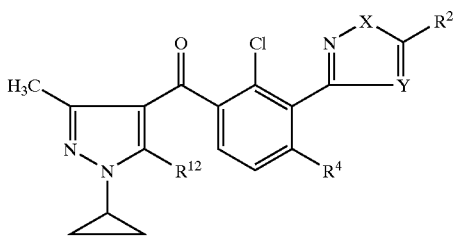

Ib2

Most particular preference is also given to the compounds of the formula Ib3, in particular to the compounds Ib3.1 to Ib3.420 which differ from the compounds Ib1.1 to Ib1.420 in that $R^{13}$ is cyclopentyl.

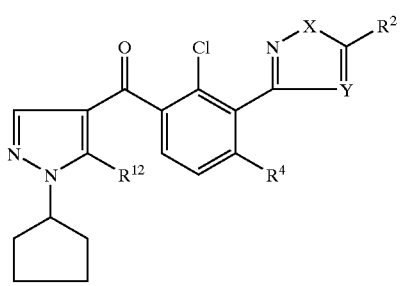

Ib3

Most particular preference is also given to the compounds of the formula Ib4, in particular to the compounds Ib4.1 to Ib4.420 which differ from the compounds Ib1.1 to Ib1.420 in that $R^{13}$ is cyclopentyl and $R^{14}$ is methyl.

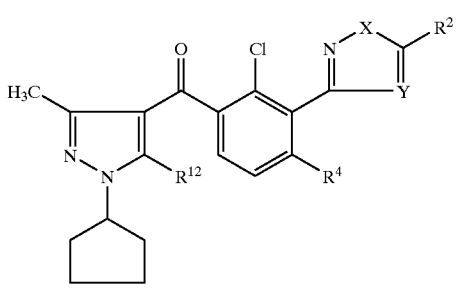

Ib4

Most particular preference is also given to the compounds of the formula Ib5, in particular to the compounds Ib5.1 to Ib5.420 which differ from the compounds Ib1.1 to Ib1.420 in that $R^{13}$ is cyclohexyl.

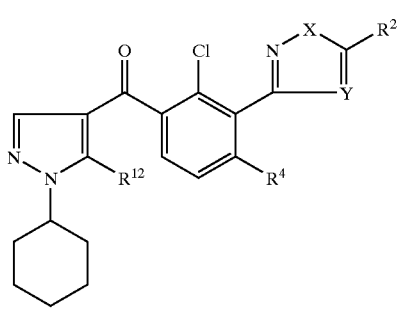

Ib5

Most particular preference is also given to the compounds of the formula Ib6, in particular to the compounds Ib6.1 to Ib6.420 which differ from the compounds Ib1.1 to Ib1.420 in that $R^{13}$ is cyclohexyl and $R^{14}$ is methyl.

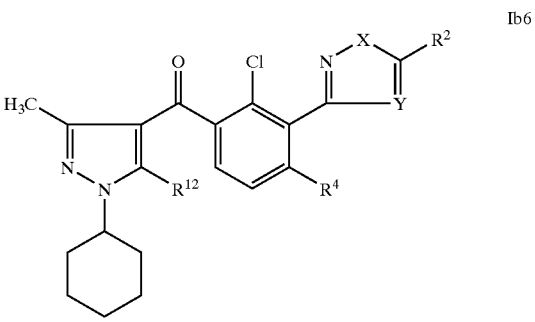

Ib6

Most particular preference is also given to the compounds of the formula Ib7, in particular to the compounds Ib7.1 to Ib7.420 which differ from the compounds Ib1.1 to Ib1.420 in that $R^{13}$ is 2-norbornyl.

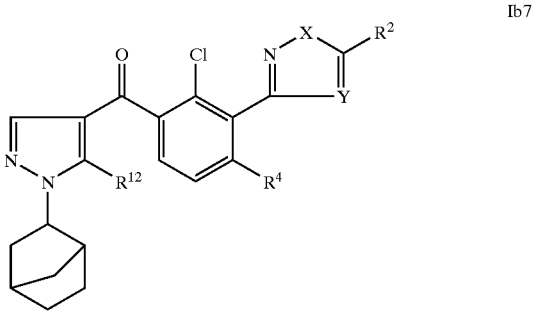

Ib7

Most particular preference is also given to the compounds of the formula Ib8, in particular to the compounds Ib8.1 to Ib8.420 which differ from the compounds Ib1.1 to Ib1.420 in that $R^{13}$ is 2-norbornyl and $R^{14}$ is methyl.

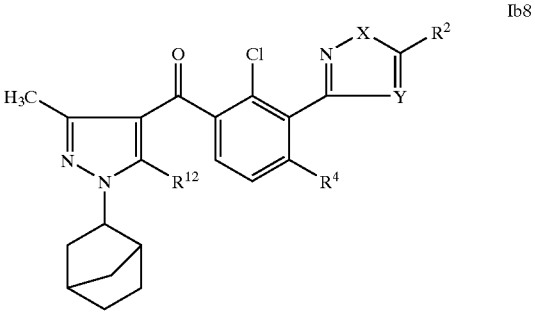

Ib8

Most particular preference is also given to the compounds of the formula Ib9, in particular to the compounds Ib9.1 to Ib9.420 which differ from the compounds Ib1.1 to Ib1.420 in that $R^{13}$ is 2-adamantyl.

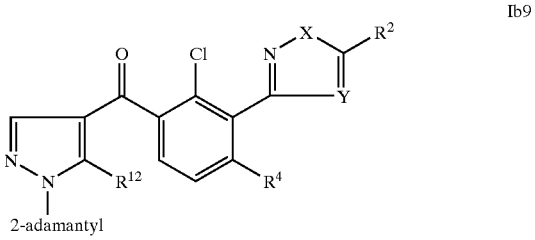

Ib9

Most particular preference is also given to the compounds of the formula Ib10, in particular to the compounds Ib10.1 to Ib10.420 which differ from the compounds Ib1.1 to Ib1.420 in that $R^{13}$ is 2-adamantyl and $R^{14}$ is methyl.

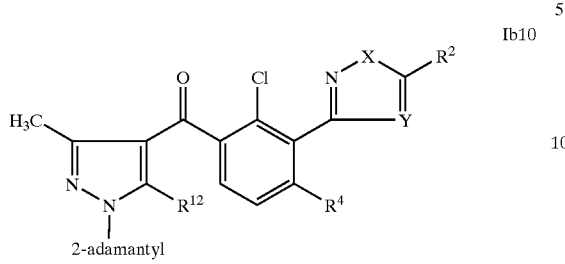

Most particular preference is also given to the compounds of the formula Ib11, in particular to the compounds Ib11.1 to Ib11.420 which differ from the corresponding compounds Ib1.1 to Ib1.420 in that $R^1$ is methyl.

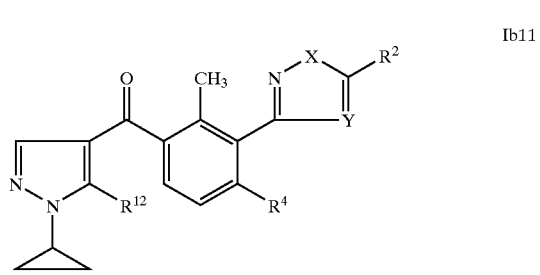

Most particular preference is also given to the compounds of the formula Ib12, in particular to the compounds Ib12.1 to Ib12.420 which differ from the corresponding compounds Ib1.1 to Ib1.420 in that $R^1$ is methyl and $R^{14}$ is methyl.

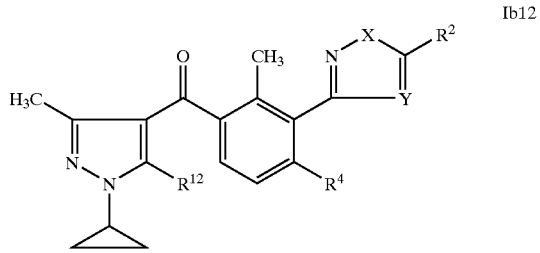

Most particular preference is also given to the compounds of the formula Ib13, in particular to the compounds Ib13.1 to Ib13.420 which differ from the compounds Ib1.1 to Ib1.420 in that $R^1$ is methyl and $R^{13}$ is cyclopentyl.

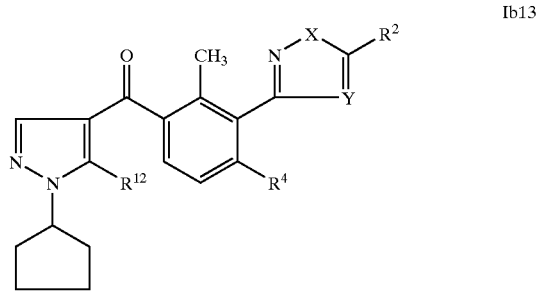

Most particular preference is also given to the compounds of the formula Ib14, in particular to the compounds Ib14.1 to Ib14.420 which differ from the compounds Ib1.1 to Ib1.420 in that $R^1$ is methyl, $R^{13}$ is cyclopentyl and $R^{14}$ is methyl.

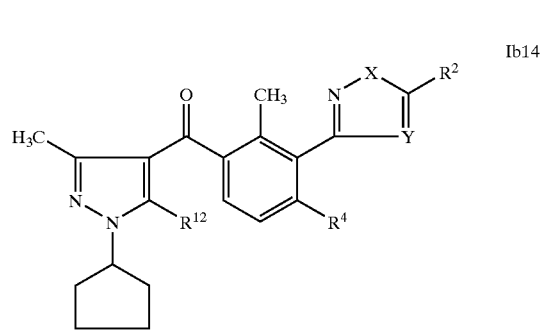

Most particular preference is also given to the compounds of the formula Ib15, in particular to the compounds Ib15.1 to Ib15.420 which differ from the compounds Ib1.1 to Ib1.420 in that $R^1$ is methyl and $R^{13}$ is cyclohexyl.

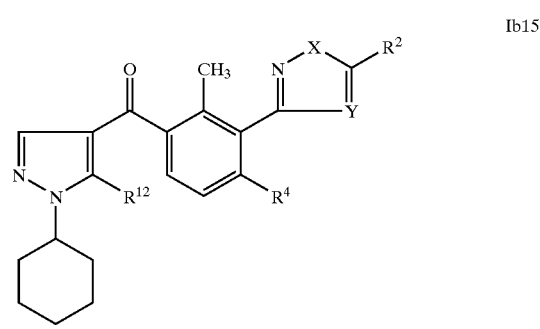

Most particular preference is also given to the compounds of the formula Ib16, in particular to the compounds Ib16.1 to Ib16.420 which differ from the compounds Ib1.1 to Ib1.420 in that $R^1$ is methyl, $R^{13}$ is cyclohexyl and $R^{14}$ is methyl.

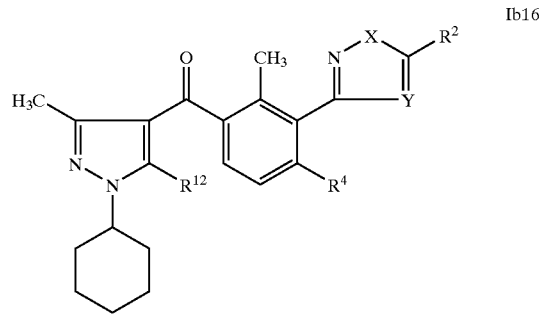

Most particular preference is also given to the compounds of the formula Ib17, in particular to the compounds Ib17.1 to Ib17.420 which differ from the compounds Ib1.1 to Ib1.420 in that $R^1$ is methyl and $R^{13}$ is 2-norbornyl.

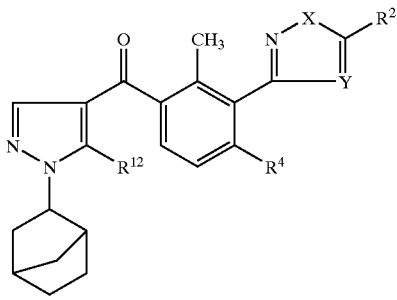

Ib17

Most particular preference is also given to the compounds of the formula Ib18, in particular to the compounds Ib18.1 to Ib18.420 which differ from the compounds Ib1.1 to Ib1.420 in that $R^1$ is methyl, $R^{13}$ is 2-norbornyl and $R^{14}$ is methyl.

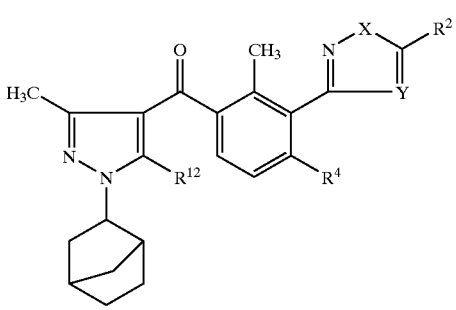

Ib18

Most particular preference is also given to the compounds of the formula Ib19, in particular to the compounds Ib19.1 to Ib19.420 which differ from the compounds Ib1.1 to Ib1.420 in that $R^1$ is methyl and $R^{13}$ is 2-adamantyl.

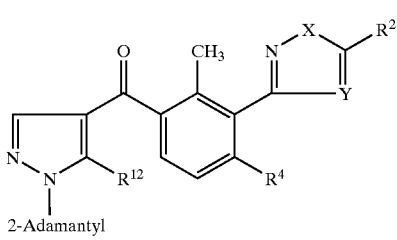

Ib19

Most particular preference is also given to the compounds of the formula Ib20, in particular to the compounds Ib20.1 to Ib20.420 which differ from the compounds Ib1.1 to Ib1.420 in that $R^1$ is methyl, $R^{13}$ is 2-adamantyl and $R^{14}$ is methyl.

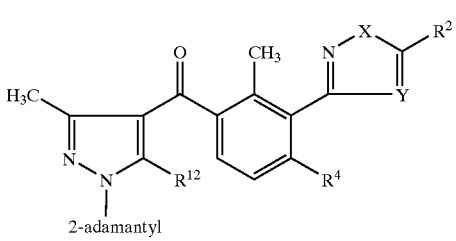

Ib20

Most particular preference is also given to the compounds of the formula Ib21, in particular to the compounds Ib21.1 to Ib21.420 which differ from the corresponding compounds Ib1.1 to Ib1.420 in that $R^1$ is methoxy.

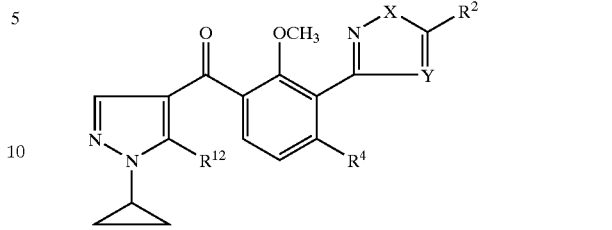

Ib21

Most particular preference is also given to the compounds of the formula Ib22, in particular to the compounds Ib22.1 to Ib22.420 which differ from the corresponding compounds Ib1.1 to Ib1.420 in that $R^1$ is methoxy and $R^{14}$ is methyl.

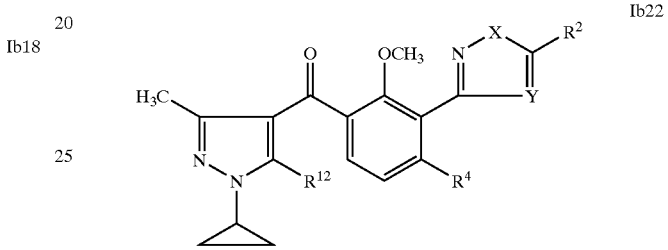

Ib22

Most particular preference is also given to the compounds of the formula Ib23, in particular to the compounds Ib23.1 to Ib23.420 which differ from the compounds Ib1.1 to Ib1.420 in that $R^1$ is methoxy and $R^{13}$ is cyclopentyl.

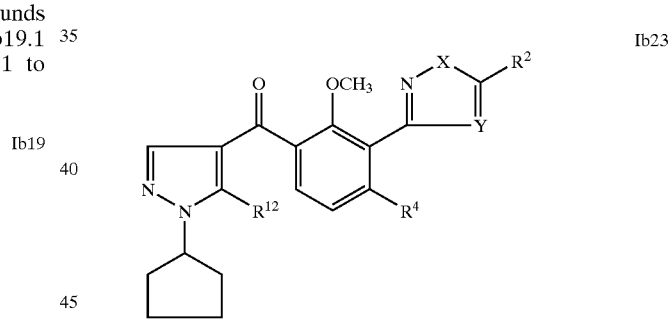

Ib23

Most particular preference is also given to the compounds of the formula Ib24, in particular to the compounds Ib24.1 to Ib24.420 which differ from the compounds Ib1.1 to Ib1.420 in that $R^1$ is methoxy, $R^{13}$ is cyclopentyl and $R^{14}$ is methyl.

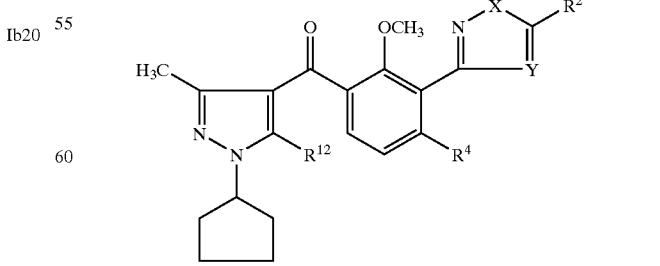

Ib24

Most particular preference is also given to the compounds of the formula Ib25, in particular to the compounds Ib25.1 to Ib25.420 which differ from the compounds Ib1.1 to Ib1.420 in that $R^1$ is methoxy and $R^{13}$ is cyclohexyl.

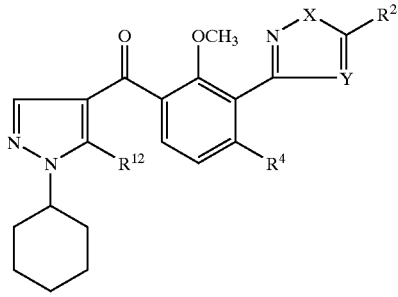

Ib25

Most particular preference is also given to the compounds of the formula Ib26, in particular to the compounds Ib26.1 to Ib26.420 which differ from the compounds Ib1.1 to Ib1.420 in that $R^1$ is methoxy, $R^{13}$ is cyclohexyl and $R^{14}$ is methyl.

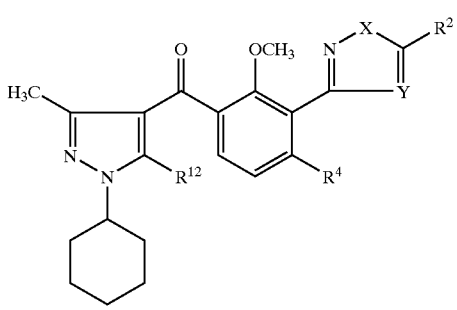

Ib26

Most particular preference is also given to the compounds of the formula Ib27, in particular to the compounds Ib27.1 to Ib27.420 which differ from the compounds Ib1.1 to Ib1.420 in that $R^1$ is methoxy and $R^{13}$ is 2-norbornyl.

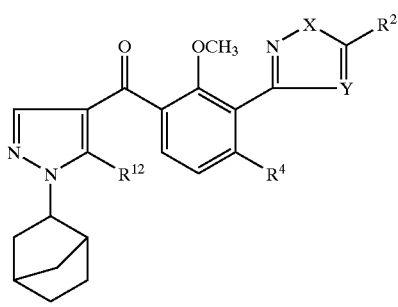

Ib27

Most particular preference is also given to the compounds of the formula Ib28, in particular to the compounds Ib28.1 to Ib28.420 which differ from the compounds Ib1.1 to Ib1.420 in that $R^1$ is methoxy, $R^{13}$ is 2-norbornyl and $R^{14}$ is methyl.

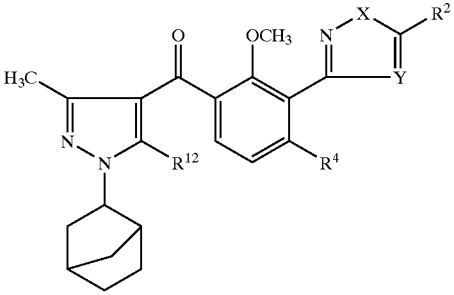

Ib28

Most particular preference is also given to the compounds of the formula Ib29, in particular to the compounds Ib29.1 to Ib29.420 which differ from the compounds Ib1.1 to Ib1.420 in that $R^1$ is methoxy and $R^{13}$ is 2-adamantyl.

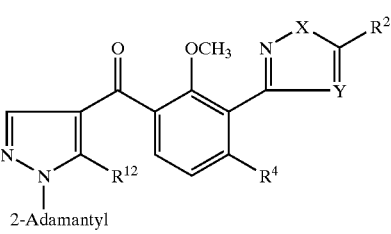

Ib29

Most particular preference is also given to the compounds of the formula Ib30, in particular to the compounds Ib30.1 to Ib30.420 which differ from the compounds Ib1.1 to Ib1.420 in that $R^1$ is methoxy, $R^{13}$ is 2-adamantyl and $R^{14}$ is methyl.

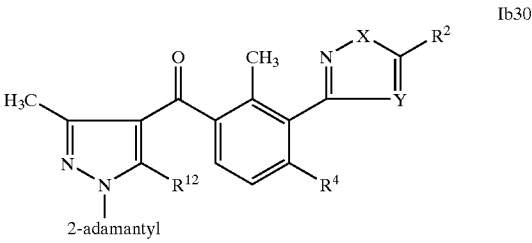

Ib30

Most particular preference is also given to the compounds of the formula Ic1 (=I where $R^1$=Cl, $R^3$ and $R^6$ or $R^3$ and $R^8$ together form a bond, $R^{13}$=cyclo-$C_3H_5$ and $R^5$ and $R^{14}$=H), in particular to the compounds Ic1.1–Ic1.720 of Table 3, where the radical definitions are of particular importance for the compounds according to the invention not only in combination with one another but in each case also on their own.

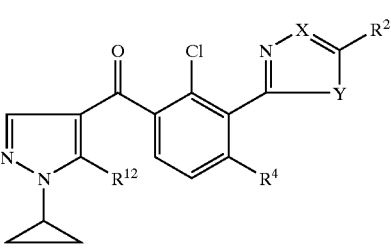

Ic1

TABLE 3

| No. | X | $R^2$ | Y | $R^4$ | $R^8$ |
|---|---|---|---|---|---|
| Ic1.1 | CH | H | O | $SCH_3$ | OH |
| Ic1.2 | CH | H | O | $SCH_2CH_3$ | OH |
| Ic1.3 | CH | H | O | $SO_2CH_3$ | OH |
| Ic1.4 | CH | H | O | $SO_2CH_2CH_3$ | OH |
| Ic1.5 | CH | H | O | $SO_2CH(CH_3)_2$ | OH |
| Ic1.6 | CH | H | O | $SO_2(CH_2)_2CH_3$ | OH |
| Ic1.7 | CH | H | O | Cl | OH |
| Ic1.8 | CH | H | O | Br | OH |
| Ic1.9 | CH | H | O | $NO_2$ | OH |
| Ic1.10 | CH | H | O | $CHF_2$ | OH |
| Ic1.11 | CH | H | O | $CF_3$ | OH |
| Ic1.12 | CH | H | O | $OCH_3$ | OH |
| Ic1.13 | CH | H | O | $OCH_2CH_3$ | OH |
| Ic1.14 | CH | H | O | $OCHF_2$ | OH |
| Ic1.15 | CH | H | O | $OCF_3$ | OH |
| Ic1.16 | CH | $CH_3$ | O | $SCH_3$ | OH |
| Ic1.17 | CH | $CH_3$ | O | $SCH_2CH_3$ | OH |
| Ic1.18 | CH | $CH_3$ | O | $SO_2CH_3$ | OH |
| Ic1.19 | CH | $CH_3$ | O | $SO_2CH_2CH_3$ | OH |
| Ic1.20 | CH | $CH_3$ | O | $SO_2CH(CH_3)_2$ | OH |
| Ic1.21 | CH | $CH_3$ | O | $SO_2(CH_2)_2CH_3$ | OH |
| Ic1.22 | CH | $CH_3$ | O | Cl | OH |
| Ic1.23 | CH | $CH_3$ | O | Br | OH |
| Ic1.24 | CH | $CH_3$ | O | $NO_2$ | OH |
| Ic1.25 | CH | $CH_3$ | O | $CHF_2$ | OH |
| Ic1.26 | CH | $CH_3$ | O | $CF_3$ | OH |
| Ic1.27 | CH | $CH_3$ | O | $OCH_3$ | OH |
| Ic1.28 | CH | $CH_3$ | O | $OCH_2CH_3$ | OH |
| Ic1.29 | CH | $CH_3$ | O | $OCF_2$ | OH |
| Ic1.30 | CH | $CH_3$ | O | $OCF_3$ | OM |
| Ic1.31 | CH | $CH_2CH_3$ | O | $SCH_3$ | OH |
| Ic1.32 | CH | $CH_2CH_3$ | O | $SCH_2CH_3$ | OH |
| Ic1.33 | CH | $CH_2CH_3$ | O | $SO_2CH_3$ | OH |
| Ic1.34 | CH | $CH_2CH_3$ | O | $SO_2CH_2CH_3$ | OH |
| Ic1.35 | CH | $CH_2CH_3$ | O | $SO_2CH(CH_3)_3$ | OH |
| Ic1.36 | CH | $CH_2CH_3$ | O | $SO_2(CH_2)_2CH_3$ | OH |
| Ic1.37 | CH | $CH_2CH_3$ | O | Cl | OH |
| Ic1.38 | CH | $CH_2CH_3$ | O | Br | OH |
| Ic1.39 | CH | $CH_2CH_3$ | O | $NO_2$ | OH |
| Ic1.40 | CH | $CH_2CH_3$ | O | $CHF_2$ | OH |
| Ic1.41 | CH | $CH_2CH_3$ | O | $CF_3$ | OH |
| Ic1.42 | CH | $CH_2CH_3$ | O | $OCH_3$ | OH |
| Ic1.43 | CH | $CH_2CH_3$ | O | $OCH_2CH_3$ | OH |
| Ic1.44 | CH | $CH_2CH_3$ | O | $OCHF_2$ | OH |
| Ic1.45 | CH | $CH_2CH_3$ | O | $OCF_3$ | OH |
| Ic1.46 | CH | $CH_2Cl$ | O | $SCH_3$ | OH |
| Ic1.47 | CH | $CH_2Cl$ | O | $SCH_2CH_3$ | OH |
| Ic1.48 | CH | $CH_2Cl$ | O | $SO_2CH_3$ | OH |
| Ic1.49 | CH | $CH_2Cl$ | O | $SO_2CH_2CH_3$ | OH |
| Ic1.50 | CH | $CH_2Cl$ | O | $SO_2CH(CH_3)_2$ | OH |
| Ic1.51 | CH | $CH_2Cl$ | O | $SO_2(CH_2)_2CH_3$ | OH |
| Ic1.52 | CH | $CH_2Cl$ | O | Cl | OH |
| Ic1.53 | CH | $CH_2Cl$ | O | Br | OH |
| Ic1.54 | CH | $CH_2Cl$ | O | $NO_2$ | OH |
| Ic1.55 | CH | $CH_2Cl$ | O | $CHF_2$ | OH |
| Ic1.56 | CH | $CH_2Cl$ | O | $CF_3$ | OH |
| Ic1.57 | CH | $CH_2Cl$ | O | $OCH_3$ | OH |
| Ic1.58 | CH | $CH_2Cl$ | O | $OCH_2CH_3$ | OH |
| Ic1.59 | CH | $CH_2Cl$ | O | $OCHF_2$ | OH |
| Ic1.60 | CH | $CH_2Cl$ | O | $OCF_3$ | OH |
| Ic1.61 | CH | H | S | $SCH_3$ | OH |
| Ic1.62 | CH | H | S | $SCH_2CH_3$ | OH |
| Ic1.63 | CH | H | S | $SO_2CH_3$ | OH |
| Ic1.64 | CH | H | S | $SO_2CH_2CH_3$ | OH |
| Ic1.65 | CH | H | S | $SO_2CH(CH_3)_2$ | OH |
| Ic1.66 | CH | H | S | $SO_2(CH_2)_2CH_3$ | OH |
| Ic1.67 | CH | H | S | Cl | OH |
| Ic1.68 | CH | H | S | Br | OH |
| Ic1.69 | CH | H | S | $NO_2$ | OH |
| Ic1.70 | CH | H | S | $CHF_2$ | OH |
| Ic1.71 | CH | H | S | $CF_3$ | OH |
| Ic1.72 | CH | H | S | $OCH_3$ | OH |
| Ic1.73 | CH | H | S | $OCH_2CH_3$ | OH |
| Ic1.74 | CH | H | S | $OCHF_2$ | OH |
| Ic1.75 | CH | H | S | $OCF_3$ | OH |
| Ic1.76 | CH | $CH_3$ | S | $SCH_3$ | OH |
| Ic1.77 | CH | $CH_3$ | S | $SCH_2CH_3$ | OH |
| Ic1.78 | CH | $CH_3$ | S | $SO_2CH_3$ | OH |
| Ic1.79 | CH | $CH_3$ | S | $SO_2CH_2CH_3$ | OH |
| Ic1.80 | CH | $CH_3$ | S | $SO_2CH(CH_3)_2$ | OH |
| Ic1.81 | CH | $CH_3$ | S | $SO_2(CH_2)_2CH_3$ | OH |
| Ic1.82 | CH | $CH_3$ | S | Cl | OH |
| Ic1.83 | CH | $CH_3$ | S | Br | OH |
| Ic1.84 | CH | $CH_3$ | S | $NO_2$ | OH |
| Ic1.85 | CH | $CH_3$ | S | $CHF_2$ | OH |
| Ic1.86 | CH | $CH_3$ | S | $CF_3$ | OH |
| Ic1.87 | CH | $CH_3$ | S | $OCH_3$ | OH |
| Ic1.88 | CH | $CH_3$ | S | $OCH_2CH_3$ | OH |
| Ic1.89 | CH | $CH_3$ | S | $OCHF_2$ | OH |
| Ic1.90 | CH | $CH_3$ | S | $OCF_3$ | OH |
| Ic1.91 | CH | $CH_2CH_3$ | S | $SCH_3$ | OH |
| Ic1.92 | CH | $CH_2CH_3$ | S | $SCH_2CH_3$ | OH |
| Ic1.93 | CH | $CH_2CH_3$ | S | $SO_2CH_3$ | OH |
| Ic1.94 | CH | $CH_2CH_3$ | S | $SO_2CH_2CH_3$ | OH |
| Ic1.95 | CH | $CH_2CH_3$ | S | $SO_2CH(CH_3)_2$ | OH |
| Ic1.96 | CH | $CH_2CH_3$ | S | $SO_2(CH_2)_2CH_3$ | OH |
| Ic1.97 | CH | $CH_2CH_3$ | S | Cl | OH |
| Ic1.98 | CH | $CH_2CH_3$ | S | Br | OH |
| Ic1.99 | CH | $CH_2CH_3$ | S | $NO_2$ | OH |
| Ic1.100 | CH | $CH_2CH_3$ | S | $CHF_2$ | OH |
| Ic1.101 | CH | $CH_2CH_3$ | S | $CF_3$ | OH |
| Ic1.102 | CH | $CH_2CH_3$ | S | $OCH_3$ | OH |
| Ic1.103 | CH | $CH_2CH_3$ | S | $OCH_2CH_3$ | OH |
| Ic1.104 | CH | $CH_2CH_3$ | S | $OCHF_2$ | OH |
| Ic1.105 | CH | $CH_2CH_3$ | S | $OCF_3$ | OH |
| Ic1.106 | CH | $CH_2Cl$ | S | $SCH_3$ | OH |
| Ic1.107 | CH | $CH_2Cl$ | S | $SCH_2CH_3$ | OH |
| Ic1.108 | CH | $CH_2Cl$ | S | $SO_2CH_3$ | OH |
| Ic1.109 | CH | $CH_2Cl$ | S | $SO_2CH_2CH_3$ | OH |
| Ic1.110 | CH | $CH_2Cl$ | S | $SO_2CH(CH_3)_2$ | OH |
| Ic1.111 | CH | $CH_2Cl$ | S | $SO_2(CH_2)_2CH_3$ | OH |
| Ic1.112 | CH | $CH_2Cl$ | S | Cl | OH |
| Ic1.113 | CH | $CH_2Cl$ | S | Br | OH |
| Ic1.114 | CH | $CH_2Cl$ | S | $NO_2$ | OH |
| Ic1.115 | CH | $CH_2Cl$ | S | $CHF_2$ | OH |
| Ic1.116 | CH | $CH_2Cl$ | S | $CF_3$ | OH |
| Ic1.117 | CH | $CH_2Cl$ | S | $OCH_3$ | OH |
| Ic1.118 | CH | $CH_2Cl$ | S | $OCH_2CH_3$ | OH |
| Ic1.119 | CH | $CH_2Cl$ | S | $OCHF_2$ | OH |
| Ic1.120 | CH | $CH_2Cl$ | S | $OCF_3$ | OH |
| Ic1.121 | CH | H | $NCH_3$ | $SCH_3$ | OH |
| Ic1.122 | CH | H | $NCH_3$ | $SCH_2CH_3$ | OH |
| Ic1.123 | CH | H | $NCH_3$ | $SO_2CH_3$ | OH |
| Ic1.124 | CH | H | $NCH_3$ | $SO_2CH_2CH_3$ | OH |
| Ic1.125 | CH | H | $NCH_3$ | $SO_2CH(CH_3)_2$ | OH |
| Ic1.126 | CH | H | $NCH_3$ | $SO_2(CH_2)_2CH_3$ | OH |
| Ic1.127 | CH | H | $NCH_3$ | Cl | OH |
| Ic1.128 | CH | H | $NCH_3$ | Br | OH |
| Ic1.129 | CH | H | $NCH_3$ | $NO_2$ | OH |
| Ic1.130 | CH | H | $NCH_3$ | $CHF_2$ | OH |
| Ic1.131 | CH | H | $NCH_3$ | $CF_3$ | OH |
| Ic1.132 | CH | H | $NCH_3$ | $OCH_3$ | OH |
| Ic1.133 | CH | H | $NCH_3$ | $OCH_2CH_3$ | OH |
| Ic1.134 | CH | H | $NCH_3$ | $OCHF_2$ | OH |
| Ic1.135 | CH | H | $NCH_3$ | $OCF_3$ | OH |
| Ic1.136 | CH | $CH_3$ | $NCH_3$ | $SCH_3$ | OH |
| Ic1.137 | CH | $CH_3$ | $NCH_3$ | $SCH_2CH_3$ | OH |
| Ic1.138 | CH | $CH_3$ | $NCH_3$ | $SO_2CH_3$ | OH |
| Ic1.139 | CH | $CH_3$ | $NCH_3$ | $SO_2CH_2CH_3$ | OH |
| Ic1.140 | CH | $CH_3$ | $NCH_3$ | $SO_2CH(CH_3)_2$ | OH |
| Ic1.141 | CH | $CH_3$ | $NCH_3$ | $SO_2(CH_2)_2CH_3$ | OH |
| Ic1.142 | CH | $CH_3$ | $NCH_3$ | Cl | OH |
| Ic1.143 | CH | $CH_3$ | $NCH_3$ | Br | OH |
| Ic1.144 | CH | $CH_3$ | $NCH_3$ | $NO_2$ | OH |
| Ic1.145 | CH | $CH_3$ | $NCH_3$ | $CHF_2$ | OH |
| Ic1.146 | CH | $CH_3$ | $NCH_3$ | $CF_3$ | OH |
| Ic1.147 | CH | $CH_3$ | $NCH_3$ | $OCH_3$ | OH |
| Ic1.148 | CH | $CH_3$ | $NCH_3$ | $OCH_2CH_3$ | OH |
| Ic1.149 | CH | $CH_3$ | $NCH_3$ | $OCHF_2$ | OH |
| Ic1.150 | CH | $CH_3$ | $NCH_3$ | $OCF_3$ | OH |
| Ic1.151 | CH | $CH_2CH_3$ | $NCH_3$ | $SCH_3$ | OH |
| Ic1.152 | CH | $CH_2CH_3$ | $NCH_3$ | $SCH_2CH_3$ | OH |
| Ic1.153 | CH | $CH_2CH_3$ | $NCH_3$ | $SO_2CH_3$ | OH |
| Ic1.154 | CH | $CH_2CH_3$ | $NCH_3$ | $SO_2CH_2CH_3$ | OH |

TABLE 3-continued

| No. | X | R² | Y | R⁴ | R⁸ |
|---|---|---|---|---|---|
| Ic1.155 | CH | CH₂CH₃ | NCH₃ | SO₂CH(CH₃)₂ | OH |
| Ic1.156 | CH | CH₂CH₃ | NCH₃ | SO₂(CH₂)₂CH₃ | OH |
| Ic1.157 | CH | CH₂CH₃ | NCH₃ | Cl | OH |
| Ic1.158 | CH | CH₂CH₃ | NCH₃ | Br | OH |
| Ic1.159 | CH | CH₂CH₃ | NCH₃ | NO₂ | OH |
| Ic1.160 | CH | CH₂CH₃ | NCH₃ | CHF₂ | OH |
| Ic1.161 | CH | CH₂CH₃ | NCH₃ | CF₃ | OH |
| Ic1.162 | CH | CH₂CH₃ | NCH₃ | OCH₃ | OH |
| Ic1.163 | CH | CH₂CH₃ | NCH₃ | OCH₂CH₃ | OH |
| Ic1.164 | CH | CH₂CH₃ | NCH₃ | OCHF₂ | OH |
| Ic1.165 | CH | CH₂CH₃ | NCH₃ | OCF₃ | OH |
| Ic1.166 | CH | CH₂Cl | NCH₃ | SCH₃ | OH |
| Ic1.167 | CH | CH₂Cl | NCH₃ | SCH₂CH₃ | OH |
| Ic1.168 | CH | CH₂Cl | NCH₃ | SO₂CH₃ | OH |
| Ic1.169 | CH | CH₂Cl | NCH₃ | SO₂CH₂CH₃ | OH |
| Ic1.170 | CH | CH₂Cl | NCH₃ | SO₂CH(CH₃)₂ | OH |
| Ic1.171 | CH | CH₂Cl | NCH₃ | SO₂(CH₂)₂CH₃ | OH |
| Ic1.172 | CH | CH₂Cl | NCH₃ | Cl | OH |
| Ic1.173 | CH | CH₂Cl | NCH₃ | Br | OH |
| Ic1.174 | CH | CH₂Cl | NCH₃ | NO₂ | OH |
| Ic1.175 | CH | CH₂Cl | NCH₃ | CHF₂ | OH |
| Ic1.176 | CH | CH₂Cl | NCH₃ | CF₃ | OH |
| Ic1.177 | CH | CH₂Cl | NCH₃ | OCH₃ | OH |
| Ic1.178 | CH | CH₂Cl | NCH₃ | OCH₂CH₃ | OH |
| Ic1.179 | CH | CH₂Cl | NCH₃ | OCHF₂ | OH |
| Ic1.180 | CH | CH₂Cl | NCH₃ | OCF₃ | OH |
| Ic1.181 | C(CH₃) | H | O | SCH₃ | OH |
| Ic1.182 | C(CH₃) | H | O | SCH₂CH₃ | OH |
| Ic1.183 | C(CH₃) | H | O | SO₂CH₃ | OH |
| Ic1.184 | C(CH₃) | H | O | SO₂CH₂CH₃ | OH |
| Ic1.185 | C(CH₃) | H | O | SO₂CH(CH₃)₂ | OH |
| Ic1.186 | C(CH₃) | H | O | SO₂(CH₂)₂CH₃ | OH |
| Ic1.187 | C(CH₃) | H | O | Cl | OH |
| Ic1.188 | C(CH₃) | H | O | Br | OH |
| Ic1.189 | C(CH₃) | H | O | NO₂ | OH |
| Ic1.190 | C(CH₃) | H | O | CHF₂ | OH |
| Ic1.191 | C(CH₃) | H | O | CF₃ | OH |
| Ic1.192 | C(CH₃) | H | O | OCH₃ | OH |
| Ic1.193 | C(CH₃) | H | O | OCH₂CH₃ | OH |
| Ic1.194 | C(CH₃) | H | O | OCHF₂ | OH |
| Ic1.195 | C(CH₃) | H | O | OCF₃ | OH |
| Ic1.196 | C(CH₃) | CH₃ | O | SCH₃ | OH |
| Ic1.197 | C(CH₃) | CH₃ | O | SCH₂CH₃ | OH |
| Ic1.198 | C(CH₃) | CH₃ | O | SO₂CH₃ | OH |
| Ic1.199 | C(CH₃) | CH₃ | O | SO₂CH₂CH₃ | OH |
| Ic1.200 | C(CH₃) | CH₃ | O | SO₂CH(CH₃)₂ | OH |
| Ic1.201 | C(CH₃) | CH₃ | O | SO₂(CH₂)₂CH₃ | OH |
| Ic1.202 | C(CH₃) | CH₃ | O | Cl | OH |
| Ic1.203 | C(CH₃) | CH₃ | O | Br | OH |
| Ic1.204 | C(CH₃) | CH₃ | O | NO₂ | OH |
| Ic1.205 | C(CH₃) | CH₃ | O | CHF₂ | OH |
| Ic1.206 | C(CH₃) | CH₃ | O | CF₃ | OH |
| Ic1.207 | C(CH₃) | CH₃ | O | OCH₃ | OH |
| Ic1.208 | C(CH₃) | CH₃ | O | OCH₂CH₃ | OH |
| Ic1.209 | C(CH₃) | CH₃ | O | OCHF₂ | OH |
| Ic1.210 | C(CH₃) | CH₃ | O | OCF₃ | OH |
| Ic1.211 | C(CH₃) | CH₂CH₃ | O | SCH₃ | OH |
| Ic1.212 | C(CH₃) | CH₂CH₃ | O | SCH₂CH₃ | OH |
| Ic1.213 | C(CH₃) | CH₂CH₃ | O | SO₂CH₃ | OH |
| Ic1.214 | C(CH₃) | CH₂CH₃ | O | SO₂CH₂CH₃ | OH |
| Ic1.215 | C(CH₃) | CH₂CH₃ | O | SO₂CH(CH₃)₂ | OH |
| Ic1.216 | C(CH₃) | CH₂CH₃ | O | SO₂(CH₂)₂CH₃ | OH |
| Ic1.217 | C(CH₃) | CH₂CH₃ | O | Cl | OH |
| Ic1.218 | C(CH₃) | CH₂CH₃ | O | Br | OH |
| Ic1.219 | C(CH₃) | CH₂CH₃ | O | NO₂ | OH |
| Ic1.220 | C(CH₃) | CH₂CH₃ | O | CHF₂ | OH |
| Ic1.221 | C(CH₃) | CH₂CH₃ | O | CF₃ | OH |
| Ic1.222 | C(CH₃) | CH₂CH₃ | O | OCH₃ | OH |
| Ic1.223 | C(CH₃) | CH₂CH₃ | O | OCH₂CH₃ | OH |
| Ic1.224 | C(CH₃) | CH₂CH₃ | O | OCHF₂ | OH |
| Ic1.225 | C(CH₃) | CH₂CH₃ | O | OCF₃ | OH |
| Ic1.226 | C(CH₃) | CH₂Cl | O | SCH₃ | OH |
| Ic1.227 | C(CH₃) | CH₂Cl | O | SCH₂CH₃ | OH |
| Ic1.228 | C(CH₃) | CH₂Cl | O | SO₂CH₃ | OH |
| Ic1.229 | C(CH₃) | CH₂Cl | O | SO₂CH₂CH₃ | OH |
| Ic1.230 | C(CH₃) | CH₂Cl | O | SO₂CH(CH₃)₂ | OH |
| Ic1.231 | C(CH₃) | CH₂Cl | O | SO₂(CH₂)₂CH₃ | OH |
| Ic1.232 | C(CH₃) | CH₂Cl | O | Cl | OH |
| Ic1.233 | C(CH₃) | CH₂Cl | O | Br | OH |
| Ic1.234 | C(CH₃) | CH₂Cl | O | NO₂ | OH |
| Ic1.235 | C(CH₃) | CH₂Cl | O | CHF₂ | OH |
| Ic1.236 | C(CH₃) | CH₂Cl | O | CF₃ | OH |
| Ic1.237 | C(CH₃) | CH₂Cl | O | OCH₃ | OH |
| Ic1.238 | C(CH₃) | CH₂Cl | O | OCH₂CH₃ | OH |
| Ic1.239 | C(CH₃) | CH₂Cl | O | OCHF₂ | OH |
| Ic1.240 | C(CH₃) | CH₂Cl | O | OCF₃ | OH |
| Ic1.241 | C(CH₃) | H | S | SCH₃ | OH |
| Ic1.242 | C(CH₃) | H | S | SCH₂CH₃ | OH |
| Ic1.243 | C(CH₃) | H | S | SO₂CH₃ | OH |
| Ic1.244 | C(CH₃) | H | S | SO₂CH₂CH₃ | OH |
| Ic1.245 | C(CH₃) | H | S | SO₂CH(CH₃)₂ | OH |
| Ic1.246 | C(CH₃) | H | S | SO₂(CH₂)₂CH₃ | OH |
| Ic1.247 | C(CH₃) | H | S | Cl | OH |
| Ic1.248 | C(CH₃) | H | S | Br | OH |
| Ic1.249 | C(CH₃) | H | S | NO₂ | OH |
| Ic1.250 | C(CH₃) | H | S | CHF₂ | OH |
| Ic1.251 | C(CH₃) | H | S | CF₃ | OH |
| Ic1.252 | C(CH₃) | H | S | OCH₃ | OH |
| Ic1.253 | C(CH₃) | H | S | OCH₂CH₃ | OH |
| Ic1.254 | C(CH₃) | H | S | OCHF₂ | OH |
| Ic1.255 | C(CH₃) | H | S | OCF₃ | OH |
| Ic1.256 | C(CH₃) | CH₃ | S | SCH₃ | OH |
| Ic1.257 | C(CH₃) | CH₃ | S | SCH₂CH₃ | OH |
| Ic1.258 | C(CH₃) | CH₃ | S | SO₂CH₃ | OH |
| Ic1.259 | C(CH₃) | CH₃ | S | SO₂CH₂CH₃ | OH |
| Ic1.260 | C(CH₃) | CH₃ | S | SO₂CH(CH₃)₂ | OH |
| Ic1.261 | C(CH₃) | CH₃ | S | SO₂(CH₂)₂CH₃ | OH |
| Ic1.262 | C(CH₃) | CH₃ | S | Cl | OH |
| Ic1.263 | C(CH₃) | CH₃ | S | Br | OH |
| Ic1.264 | C(CH₃) | CH₃ | S | NO₂ | OH |
| Ic1.265 | C(CH₃) | CH₃ | S | CHF₂ | OH |
| Ic1.266 | C(CH₃) | CH₃ | S | CF₃ | OH |
| Ic1.267 | C(CH₃) | CH₃ | S | OCH₃ | OH |
| Ic1.268 | C(CH₃) | CH₃ | S | OCH₂CH₃ | OH |
| Ic1.269 | C(CH₃) | CH₃ | S | OCHF₂ | OH |
| Ic1.270 | C(CH₃) | CH₃ | S | OCF₃ | OH |
| Ic1.271 | C(CH₃) | CH₂CH₃ | S | SCH₃ | OH |
| Ic1.272 | C(CH₃) | CH₂CH₃ | S | SCH₂CH₃ | OH |
| Ic1.273 | C(CH₃) | CH₂CH₃ | S | SO₂CH₃ | OH |
| Ic1.274 | C(CH₃) | CH₂CH₃ | S | SO₂CH₂CH₃ | OH |
| Ic1.275 | C(CH₃) | CH₂CH₃ | S | SO₂CH(CH₃)₂ | OH |
| Ic1.276 | C(CH₃) | CH₂CH₃ | S | SO₂(CH₂)₂CH₃ | OH |
| Ic1.277 | C(CH₃) | CH₂CH₃ | S | Cl | OH |
| Ic1.278 | C(CH₃) | CH₂CH₃ | S | Br | OH |
| Ic1.279 | C(CH₃) | CH₂CH₃ | S | NO₂ | OH |
| Ic1.280 | C(CH₃) | CH₂CH₃ | S | CHF₂ | OH |
| Ic1.281 | C(CH₃) | CH₂CH₃ | S | CF₃ | OH |
| Ic1.282 | C(CH₃) | CH₂CH₃ | S | OCH₃ | OH |
| Ic1.283 | C(CH₃) | CH₂CH₃ | S | OCH₂CH₃ | OH |
| Ic1.284 | C(CH₃) | CH₂CH₃ | S | OCHF₂ | OH |
| Ic1.285 | C(CH₃) | CH₂CH₃ | S | OCF₃ | OH |
| Ic1.286 | C(CH₃) | CH₂Cl | S | SCH₃ | OH |
| Ic1.287 | C(CH₃) | CH₂Cl | S | SCH₂CH₃ | OH |
| Ic1.288 | C(CH₃) | CH₂Cl | S | SO₂CH₃ | OH |
| Ic1.289 | C(CH₃) | CH₂Cl | S | SO₂CH₂CH₃ | OH |
| Ic1.290 | C(CH₃) | CH₂Cl | S | SO₂CH(CH₃)₂ | OH |
| Ic1.291 | C(CH₃) | CH₂Cl | S | SO₂(CH₂)₂CH₃ | OH |
| Ic1.292 | C(CH₃) | CH₂Cl | S | Cl | OH |
| Ic1.293 | C(CH₃) | CH₂Cl | S | Br | OH |
| Ic1.294 | C(CH₃) | CH₂Cl | S | NO₂ | OH |
| Ic1.295 | C(CH₃) | CH₂Cl | S | CHF₂ | OH |
| Ic1.296 | C(CH₃) | CH₂Cl | S | CF₃ | OH |
| Ic1.297 | C(CH₃) | CH₂Cl | S | OCH₃ | OH |
| Ic1.298 | C(CH₃) | CH₂Cl | S | OCH₂CH₃ | OH |
| Ic1.299 | C(CH₃) | CH₂Cl | S | OCHF₂ | OH |
| Ic1.300 | C(CH₃) | CH₂Cl | S | OCF₃ | OH |
| Ic1.301 | C(CH₃) | H | NCH₃ | SCH₃ | OH |
| Ic1.302 | C(CH₃) | H | NCH₃ | SCH₂CH₃ | OH |
| Ic1.303 | C(CH₃) | H | NCH₃ | SO₂CH₃ | OH |
| Ic1.304 | C(CH₃) | H | NCH₃ | SO₂CH₂CH₃ | OH |
| Ic1.305 | C(CH₃) | H | NCH₃ | SO₂CH(CH₃)₂ | OH |
| Ic1.306 | C(CH₃) | H | NCH₃ | SO₂(CH₂)₂CH₃ | OH |
| Ic1.307 | C(CH₃) | H | NCH₃ | Cl | OH |
| Ic1.308 | C(CH₃) | H | NCH₃ | Br | OH |

TABLE 3-continued

| No. | X | R² | Y | R⁴ | R⁸ |
|---|---|---|---|---|---|
| Ic1.309 | C(CH₃) | H | NCH₃ | NO₂ | OH |
| Ic1.310 | C(CH₃) | H | NCH₃ | CHF₂ | OH |
| Ic1.311 | C(CH₃) | H | NCH₃ | CF₃ | OH |
| Ic1.312 | C(CH₃) | H | NCH₃ | OCH₃ | OH |
| Ic1.313 | C(CH₃) | H | NCH₃ | OCH₂CH₃ | OH |
| Ic1.314 | C(CH₃) | H | NCH₃ | OCHF₂ | OH |
| Ic1.315 | C(CH₃) | H | NCH₃ | OCF₃ | OH |
| Ic1.316 | C(CH₃) | CH₃ | NCH₃ | SCH₃ | OH |
| Ic1.317 | C(CH₃) | CH₃ | NCH₃ | SCH₂CH₃ | OH |
| Ic1.318 | C(CH₃) | CH₃ | NCH₃ | SO₂CH₃ | OH |
| Ic1.319 | C(CH₃) | CH₃ | NCH₃ | SO₂CH₂CH₃ | OH |
| Ic1.320 | C(CH₃) | CH₃ | NCH₃ | SO₂CH(CH₃)₂ | OH |
| Ic1.321 | C(CH₃) | CH₃ | NCH₃ | SO₂(CH₂)₂CH₃ | OH |
| Ic1.322 | C(CH₃) | CH₃ | NCH₃ | Cl | OH |
| Ic1.323 | C(CH₃) | CH₃ | NCH₃ | Br | OH |
| Ic1.324 | C(CH₃) | CH₃ | NCH₃ | NO₂ | OH |
| Ic1.325 | C(CH₃) | CH₃ | NCH₃ | CHF₂ | OH |
| Ic1.326 | C(CH₃) | CH₃ | NCH₃ | CF₃ | OH |
| Ic1.327 | C(CH₃) | CH₃ | NCH₃ | OCH₃ | OH |
| Ic1.328 | C(CH₃) | CH₃ | NCH₃ | OCH₂CH₃ | OH |
| Ic1.329 | C(CH₃) | CH₃ | NCH₃ | OCHF₂ | OH |
| Ic1.330 | C(CH₃) | CH₃ | NCH₃ | OCF₃ | OH |
| Ic1.331 | C(CH₃) | CH₂CH₃ | NCH₃ | SCH₃ | OH |
| Ic1.332 | C(CH₃) | CH₂CH₃ | NCH₃ | SCH₂CH₃ | OH |
| Ic1.333 | C(CH₃) | CH₂CH₃ | NCH₃ | SO₂CH₂ | OH |
| Ic1.334 | C(CH₃) | CH₂CH₃ | NCH₃ | SO₂CH₂CH₃ | OH |
| Ic1.335 | C(CH₃) | CH₂CH₃ | NCH₃ | SO₂CH(CH₂)₂ | OH |
| Ic1.336 | C(CH₃) | CH₂CH₃ | NCH₃ | SO₂(CH₂)₂CH₃ | OH |
| Ic1.337 | C(CH₃) | CH₂CH₃ | NCH₃ | Cl | OH |
| Ic1.338 | C(CH₃) | CH₂CH₃ | NCH₃ | Br | OH |
| Ic1.339 | C(CH₃) | CH₂CH₃ | NCH₃ | NO₂ | OH |
| Ic1.340 | C(CH₃) | CH₂CH₃ | NCH₃ | CHF₂ | OH |
| Ic1.341 | C(CH₃) | CH₂CH₃ | NCH₃ | CF₃ | OH |
| Ic1.342 | C(CH₃) | CH₂CH₃ | NCH₃ | OCH₃ | OH |
| Ic1.343 | C(CH₃) | CH₂CH₃ | NCH₃ | OCH₂CH₃ | OH |
| Ic1.344 | C(CH₃) | CH₂CH₃ | NCH₃ | OCHF₂ | OH |
| Ic1.345 | C(CH₃) | CH₂CH₃ | NCH₃ | OCF₃ | OH |
| Ic1.346 | C(CH₃) | CH₂Cl | NCH₃ | SCH₃ | OH |
| Ic1.347 | C(CH₃) | CH₂Cl | NCH₃ | SCH₂CH₃ | OH |
| Ic1.348 | C(CH₃) | CH₂Cl | NCH₃ | SO₂CH₃ | OH |
| Ic1.349 | C(CH₃) | CH₂Cl | NCH₃ | SO₂CH₂CH₃ | OH |
| Ic1.350 | C(CH₃) | CH₂Cl | NCH₃ | SO₂CH(CH₃)₂ | OH |
| Ic1.351 | C(CH₃) | CH₂Cl | NCH₃ | SO₂(CH₂)₂CH₃ | OH |
| Ic1.352 | C(CH₃) | CH₂Cl | NCH₃ | Cl | OH |
| Ic1.353 | C(CH₃) | CH₂Cl | NCH₃ | Br | OH |
| Ic1.354 | C(CH₃) | CH₂Cl | NCH₃ | NO₂ | OH |
| Ic1.355 | C(CH₃) | CH₂Cl | NCH₃ | CHF₂ | OH |
| Ic1.356 | C(CH₃) | CH₂Cl | NCH₃ | CF₃ | OH |
| Ic1.357 | C(CH₃) | CH₂Cl | NCH₃ | OCH₃ | OH |
| Ic1.358 | C(CH₃) | CH₂Cl | NCH₃ | OCH₂CH₃ | OH |
| Ic1.359 | C(CH₃) | CH₂Cl | NCH₃ | OCHF₂ | OH |
| Ic1.360 | C(CH₃) | CH₂Cl | NCH₃ | OCF₃ | OH |
| Ic1.361 | C(CH₂CH₃) | H | O | SCH₃ | OH |
| Ic1.362 | C(CH₂CH₃) | H | O | SCH₂CH₃ | OH |
| Ic1.363 | C(CH₂CH₃) | H | O | SO₂CH₃ | OH |
| Ic1.364 | C(CH₂CH₃) | H | O | SO₂CH₂CH₃ | OH |
| Ic1.365 | C(CH₂CH₃) | H | O | SO₂CH(CH₃)₂ | OH |
| Ic1.366 | C(CH₂CH₃) | H | O | SO₂(CH₂)₂CH₃ | OH |
| Ic1.367 | C(CH₂CH₃) | H | O | Cl | OH |
| Ic1.368 | C(CH₂CH₃) | H | O | Br | OH |
| Ic1.369 | C(CH₂CH₃) | H | O | NO₂ | OH |
| Ic1.370 | C(CH₂CH₃) | H | O | CHF₂ | OH |
| Ic1.371 | C(CH₂CH₃) | H | O | CF₃ | OH |
| Ic1.372 | C(CH₂CH₃) | H | O | OCH₃ | OH |
| Ic1.373 | C(CH₂CH₃) | H | O | OCH₂CH₃ | OH |
| Ic1.374 | C(CH₂CH₃) | H | O | OCHF₂ | OH |
| Ic1.375 | C(CH₂CH₃) | H | O | OCF₃ | OH |
| Ic1.376 | C(CH₂CH₃) | CH₃ | O | SCH₃ | OH |
| Ic1.377 | C(CH₂CH₃) | CH₃ | O | SCH₂CH₃ | OH |
| Ic1.378 | C(CH₂CH₃) | CH₃ | O | SO₂CH₃ | OH |
| Ic1.379 | C(CH₂CH₃) | CH₃ | O | SO₂CH₂CH₃ | OH |
| Ic1.380 | C(CH₂CH₃) | CH₃ | O | SO₂CH(CH₃)₂ | OH |
| Ic1.381 | C(CH₂CH₃) | CH₃ | O | SO₂(CH₂)₂CH₃ | OH |
| Ic1.382 | C(CH₂CH₃) | CH₃ | O | Cl | OH |
| Ic1.383 | C(CH₂CH₃) | CH₃ | O | Br | OH |
| Ic1.384 | C(CH₂CH₃) | CH₃ | O | NO₂ | OH |
| Ic1.385 | C(CH₂CH₃) | CH₃ | O | CHF₂ | OH |
| Ic1.386 | C(CH₂CH₃) | CH₃ | O | CF₃ | OH |
| Ic1.387 | C(CH₂CH₃) | CH₃ | O | OCH₃ | OH |
| Ic1.388 | C(CH₂CH₃) | CH₃ | O | OCH₂CH₃ | OH |
| Ic1.389 | C(CH₂CH₃) | CH₃ | O | OCHF₂ | OH |
| Ic1.390 | C(CH₂CH₃) | CH₃ | O | OCF₃ | OH |
| Ic1.391 | C(CH₂CH₃) | CH₂CH₃ | O | SCH₃ | OH |
| Ic1.392 | C(CH₂CH₃) | CH₂CH₃ | O | SCH₂CH₃ | OH |
| Ic1.393 | C(CH₂CH₃) | CH₂CH₃ | O | SO₂CH₃ | OH |
| Ic1.394 | C(CH₂CH₃) | CH₂CH₃ | O | SO₂CH₂CH₃ | OH |
| Ic1.395 | C(CH₂CH₃) | CH₂CH₃ | O | SO₂CH(CH₃)₂ | OH |
| Ic1.396 | C(CH₂CH₃) | CH₂CH₃ | O | SO₂(CH₂)₂CH₃ | OH |
| Ic1.397 | C(CH₂CH₃) | CH₂CH₃ | O | Cl | OH |
| Ic1.398 | C(CH₂CH₃) | CH₂CH₃ | O | Br | OH |
| Ic1.399 | C(CH₂CH₃) | CH₂CH₃ | O | NO₂ | OH |
| Ic1.400 | C(CH₂CH₃) | CH₂CH₃ | O | CHF₂ | OH |
| Ic1.401 | C(CH₂CH₃) | CH₂CH₃ | O | CF₃ | OH |
| Ic1.402 | C(CH₂CH₃) | CH₂CH₃ | O | OCH₃ | OH |
| Ic1.403 | C(CH₂CH₃) | CH₂CH₃ | O | OCH₂CH₃ | OH |
| Ic1.404 | C(CH₂CH₃) | CH₂CH₃ | O | OCHF₂ | OH |
| Ic1.405 | C(CH₂CH₃) | CH₂CH₃ | O | OCF₃ | OH |
| Ic1.406 | C(CH₂CH₃) | CH₂Cl | O | SCH₃ | OH |
| Ic1.407 | C(CH₂CH₃) | CH₂Cl | O | SCH₂CH₃ | OH |
| Ic1.408 | C(CH₂CH₃) | CH₂Cl | O | SO₂CH₃ | OH |
| Ic1.409 | C(CH₂CH₃) | CH₂Cl | O | SO₂CH₂CH₃ | OH |
| Ic1.410 | C(CH₂CH₃) | CH₂Cl | O | SO₂CH(CH₃)₂ | OH |
| Ic1.411 | C(CH₂CH₃) | CH₂Cl | O | SO₂(CH₂)₂CH₃ | OH |
| Ic1.412 | C(CH₂CH₃) | CH₂Cl | O | Cl | OH |
| Ic1.413 | C(CH₂CH₃) | CH₂Cl | O | Br | OH |
| Ic1.414 | C(CH₂CH₃) | CH₂Cl | O | NO₂ | OH |
| Ic1.415 | C(CH₂CH₃) | CH₂Cl | O | CHF₂ | OH |
| Ic1.416 | C(CH₂CH₃) | CH₂Cl | O | CF₃ | OH |
| Ic1.417 | C(CH₂CH₃) | CH₂Cl | O | OCH₃ | OH |
| Ic1.418 | C(CH₂CH₃) | CH₂Cl | O | OCH₂CH₃ | OH |
| Ic1.419 | C(CH₂CH₃) | CH₂Cl | O | OCHF₂ | OH |
| Ic1.420 | C(CH₂CH₃) | CH₂Cl | O | OCF₃ | OH |
| Ic1.421 | C(CH₂CH₃) | H | S | SCH₃ | OH |
| Ic1.422 | C(CH₂CH₃) | H | S | SCH₂CH₃ | OH |
| Ic1.423 | C(CH₂CH₃) | H | S | SO₂CH₃ | OH |
| Ic1.424 | C(CH₂CH₃) | H | S | SO₂CH₂CH₃ | OH |
| Ic1.425 | C(CH₂CH₃) | H | S | SO₂CH(CH₃)₂ | OH |
| Ic1.426 | C(CH₂CH₃) | H | S | SO₂(CH₂)₂CH₃ | OH |
| Ic1.427 | C(CH₂CH₃) | H | S | Cl | OH |
| Ic1.428 | C(CH₂CH₃) | H | S | Br | OH |
| Ic1.429 | C(CH₂CH₃) | H | S | NO₂ | OH |
| Ic1.430 | C(CH₂CH₃) | H | S | CHF₂ | OH |
| Ic1.431 | C(CH₂CH₃) | H | S | CF₃ | OH |
| Ic1.432 | C(CH₂CH₃) | H | S | OCH₃ | OH |
| Ic1.433 | C(CH₂CH₃) | H | S | OCH₂CH₃ | OH |
| Ic1.434 | C(CH₂CH₃) | H | S | OCHF₂ | OH |
| Ic1.435 | C(CH₂CH₃) | H | S | OCF₃ | OH |
| Ic1.436 | C(CH₂CH₃) | CH₃ | S | SCH₃ | OH |
| Ic1.437 | C(CH₂CH₃) | CH₃ | S | SCH₂CH₃ | OH |
| Ic1.438 | C(CH₂CH₃) | CH₃ | S | SO₂CH₃ | OH |
| Ic1.439 | C(CH₂CH₃) | CH₃ | S | SO₂CH₂CH₃ | OH |
| Ic1.440 | C(CH₂CH₃) | CH₃ | S | SO₂CH(CH₃)₂ | OH |
| Ic1.441 | C(CH₂CH₃) | CH₃ | S | SO₂(CH₂)₂CH₃ | OH |
| Ic1.442 | C(CH₂CH₃) | CH₃ | S | Cl | OH |
| Ic1.443 | C(CH₂CH₃) | CH₃ | S | Br | OH |
| Ic1.444 | C(CH₂CH₃) | CH₃ | S | NO₂ | OH |
| Ic1.445 | C(CH₂CH₃) | CH₃ | S | CHF₂ | OH |
| Ic1.446 | C(CH₂CH₃) | CH₃ | S | CF₃ | OH |
| Ic1.447 | C(CH₂CH₃) | CH₃ | S | OCH₃ | OH |
| Ic1.448 | C(CH₂CH₃) | CH₃ | S | OCH₂CH₃ | OH |
| Ic1.449 | C(CH₂CH₃) | CH₃ | S | OCHF₂ | OH |
| Ic1.450 | C(CH₂CH₃) | CH₃ | S | OCF₃ | OH |
| Ic1.451 | C(CH₂CH₃) | CH₂CH₃ | S | SCH₃ | OH |
| Ic1.452 | C(CH₂CH₃) | CH₂CH₃ | S | SCH₂CH₃ | OH |
| Ic1.453 | C(CH₂CH₃) | CH₂CH₃ | S | SO₂CH₃ | OH |
| Ic1.454 | C(CH₂CH₃) | CH₂CH₃ | S | SO₂CH₂CH₃ | OH |
| Ic1.455 | C(CH₂CH₃) | CH₂CH₃ | S | SO₂CH(CH₃)₂ | OH |
| Ic1.456 | C(CH₂CH₃) | CH₂CH₃ | S | SO₂(CH₂)₂CH₃ | OH |
| Ic1.457 | C(CH₂CH₃) | CH₂CH₃ | S | Cl | OH |
| Ic1.458 | C(CH₂CH₃) | CH₂CH₃ | S | Br | OH |
| Ic1.459 | C(CH₂CH₃) | CH₂CH₃ | S | NO₂ | OH |
| Ic1.460 | C(CH₂CH₃) | CH₂CH₃ | S | CHF₂ | OH |
| Ic1.461 | C(CH₂CH₃) | CH₂CH₃ | S | CF₃ | OH |
| Ic1.462 | C(CH₂CH₃) | CH₂CH₃ | S | OCH₃ | OH |

TABLE 3-continued

| No. | X | R² | Y | R⁴ | R⁸ |
|---|---|---|---|---|---|
| Ic1.463 | C(CH₂CH₃) | CH₂CH₃ | S | OCH₂CH₃ | OH |
| Ic1.464 | C(CH₂CH₃) | CH₂CH₃ | S | OCHF₂ | OH |
| Ic1.465 | C(CH₂CH₃) | CH₂CH₃ | S | OCF₃ | OH |
| Ic1.466 | C(CH₂CH₃) | CH₂Cl | S | SCH₃ | OH |
| Ic1.467 | C(CH₂CH₃) | CH₂Cl | S | SCH₂CH₃ | OH |
| Ic1.468 | C(CH₂CH₃) | CH₂Cl | S | SO₂CH₃ | OH |
| Ic1.469 | C(CH₂CH₃) | CH₂Cl | S | SO₂CH₂CH₃ | OH |
| Ic1.470 | C(CH₂CH₃) | CH₂Cl | S | SO₂CH(CH₃)₂ | OH |
| Ic1.471 | C(CH₂CH₃) | CH₂Cl | S | SO₂(CH₂)₂CH₃ | OH |
| Ic1.472 | C(CH₂CH₃) | CH₂Cl | S | Cl | OH |
| Ic1.473 | C(CH₂CH₃) | CH₂Cl | S | Br | OH |
| Ic1.474 | C(CH₂CH₃) | CH₂Cl | S | NO₂ | OH |
| Ic1.475 | C(CH₂CH₃) | CH₂Cl | S | CHF₂ | OH |
| Ic1.476 | C(CH₂CH₃) | CH₂Cl | S | CF₃ | OH |
| Ic1.477 | C(CH₂CH₃) | CH₂Cl | S | OCH₃ | OH |
| Ic1.478 | C(CH₂CH₃) | CH₂Cl | S | OCH₂CH₃ | OH |
| Ic1.479 | C(CH₂CH₃) | CH₂Cl | S | OCHF₂ | OH |
| Ic1.480 | C(CH₂CH₃) | CH₂Cl | S | OCF₃ | OH |
| Ic1.481 | C(CH₂CH₃) | H | NCH₃ | SCH₃ | OH |
| Ic1.482 | C(CH₂CH₃) | H | NCH₃ | SCH₂CH₃ | OH |
| Ic1.483 | C(CH₂CH₃) | H | NCH₃ | SO₂CH₃ | OH |
| Ic1.484 | C(CH₂CH₃) | H | NCH₃ | SO₂CH₂CH₃ | OH |
| Ic1.485 | C(CH₂CH₃) | H | NCH₃ | SO₂CH(CH₃)₂ | OH |
| Ic1.486 | C(CH₂CH₃) | H | NCH₃ | SO₂(CH₂)₂CH₃ | OH |
| Ic1.487 | C(CH₂CH₃) | H | NCH₃ | Cl | OH |
| Ic1.488 | C(CH₂CH₃) | H | NCH₃ | Br | OH |
| Ic1.489 | C(CH₂CH₃) | H | NCH₃ | NO₂ | OH |
| Ic1.490 | C(CH₂CH₃) | H | NCH₃ | CHF₂ | OH |
| Ic1.491 | C(CH₂CH₃) | H | NCH₃ | CF₃ | OH |
| Ic1.492 | C(CH₂CH₃) | H | NCH₃ | OCH₃ | OH |
| Ic1.493 | C(CH₂CH₃) | H | NCH₃ | OCH₂CH₃ | OH |
| Ic1.494 | C(CH₂CH₃) | H | NCH₃ | OCHF₂ | OH |
| Ic1.495 | C(CH₂CH₃) | H | NCH₃ | OCF₃ | OH |
| Ic1.496 | C(CH₂CH₃) | CH₃ | NCH₃ | SCH₃ | OH |
| Ic1.497 | C(CH₂CH₃) | CH₃ | NCH₃ | SCH₂CH₃ | OH |
| Ic1.498 | C(CH₂CH₃) | CH₃ | NCH₃ | SO₂CH₃ | OH |
| Ic1.499 | C(CH₂CH₃) | CH₃ | NCH₃ | SO₂CH₂CH₃ | OH |
| Ic1.500 | C(CH₂CH₃) | CH₃ | NCH₃ | SO₂CH(CH₃)₂ | OH |
| Ic1.501 | C(CH₂CH₃) | CH₃ | NCH₃ | SO₂(CH₂)₂CH₃ | OH |
| Ic1.502 | C(CH₂CH₃) | CH₃ | NCH₃ | Cl | OH |
| Ic1.503 | C(CH₂CH₃) | CH₃ | NCH₃ | Br | OH |
| Ic1.504 | C(CH₂CH₃) | CH₃ | NCH₃ | NO₂ | OH |
| Ic1.505 | C(CH₂CH₃) | CH₃ | NCH₃ | CHF₂ | OH |
| Ic1.506 | C(CH₂CH₃) | CH₃ | NCH₃ | CF₃ | OH |
| Ic1.507 | C(CH₂CH₃) | CH₃ | NCH₃ | OCH₃ | OH |
| Ic1.508 | C(CH₂CH₃) | CH₃ | NCH₃ | OCH₂CH₃ | OH |
| Ic1.509 | C(CH₂CH₃) | CH₃ | NCH₃ | OCHF₂ | OH |
| Ic1.510 | C(CH₂CH₃) | CH₃ | NCH₃ | OCF₃ | OH |
| Ic1.511 | C(CH₂CH₃) | CH₂CH₃ | NCH₃ | SCH₃ | OH |
| Ic1.512 | C(CH₂CH₃) | CH₂CH₃ | NCH₃ | SCH₂CH₃ | OH |
| Ic1.513 | C(CH₂CH₃) | CH₂CH₃ | NCH₃ | SO₂CH₃ | OH |
| Ic1.514 | C(CH₂CH₃) | CH₂CH₃ | NCH₃ | SO₂CH₂CH₃ | OH |
| Ic1.515 | C(CH₂CH₃) | CH₂CH₃ | NCH₃ | SO₂CH(CH₃)₂ | OH |
| Ic1.516 | C(CH₂CH₃) | CH₂CH₃ | NCH₃ | SO₂(CH₂)₂CH₃ | OH |
| Ic1.517 | C(CH₂CH₃) | CH₂CH₃ | NCH₃ | Cl | OH |
| Ic1.518 | C(CH₂CH₃) | CH₂CH₃ | NCH₃ | Br | OH |
| Ic1.519 | C(CH₂CH₃) | CH₂CH₃ | NCH₃ | NO₂ | OH |
| Ic1.520 | C(CH₂CH₃) | CH₂CH₃ | NCH₃ | CHF₂ | OH |
| Ic1.521 | C(CH₂CH₃) | CH₂CH₃ | NCH₃ | CF₃ | OH |
| Ic1.522 | C(CH₂CH₃) | CH₂CH₃ | NCH₃ | OCH₃ | OH |
| Ic1.523 | C(CH₂CH₃) | CH₂CH₃ | NCH₃ | OCH₂CH₃ | OH |
| Ic1.524 | C(CH₂CH₃) | CH₂CH₃ | NCH₃ | OCHF₂ | OH |
| Ic1.525 | C(CH₂CH₃) | CH₂CH₃ | NCH₃ | OCF₃ | OH |
| Ic1.526 | C(CH₂CH₃) | CH₂Cl | NCH₃ | SCH₃ | OH |
| Ic1.527 | C(CH₂CH₃) | CH₂Cl | NCH₃ | SCH₂CH₃ | OH |
| Ic1.528 | C(CH₂CH₃) | CH₂Cl | NCH₃ | SO₂CH₃ | OH |
| Ic1.529 | C(CH₂CH₃) | CH₂Cl | NCH₃ | SO₂CH₂CH₃ | OH |
| Ic1.530 | C(CH₂CH₃) | CH₂Cl | NCH₃ | SO₂CH(CH₃)₂ | OH |
| Ic1.531 | C(CH₂CH₃) | CH₂Cl | NCH₃ | SO₂(CH₂)₂CH₃ | OH |
| Ic1.532 | C(CH₂CH₃) | CH₂Cl | NCH₃ | Cl | OH |
| Ic1.533 | C(CH₂CH₃) | CH₂Cl | NCH₃ | Br | OH |
| Ic1.534 | C(CH₂CH₃) | CH₂Cl | NCH₃ | NO₂ | OH |
| Ic1.535 | C(CH₂CH₃) | CH₂Cl | NCH₃ | CHF₂ | OH |
| Ic1.536 | C(CH₂CH₃) | CH₂Cl | NCH₃ | CF₃ | OH |
| Ic1.537 | C(CH₂CH₃) | CH₂Cl | NCH₃ | OCH₃ | OH |
| Ic1.538 | C(CH₂CH₃) | CH₂Cl | NCH₃ | OCH₂CH₃ | OH |
| Ic1.539 | C(CH₂CH₃) | CH₂Cl | NCH₃ | OCHF₂ | OH |
| Ic1.540 | C(CH₂CH₃) | CH₂Cl | NCH₃ | OCF₃ | OH |
| Ic1.541 | N | H | O | SCH₃ | OH |
| Ic1.542 | N | H | O | SCH₂CH₃ | OH |
| Ic1.543 | N | H | O | SO₂CH₃ | OH |
| Ic1.544 | N | H | O | SO₂CH₂CH₃ | OH |
| Ic1.545 | N | H | O | SO₂CH(CH₃)₂ | OH |
| Ic1.546 | N | H | O | SO₂(CH₂)₂CH₃ | OH |
| Ic1.547 | N | H | O | Cl | OH |
| Ic1.548 | N | H | O | Br | OH |
| Ic1.549 | N | H | O | NO₂ | OH |
| Ic1.550 | N | H | O | CHF₂ | OH |
| Ic1.551 | N | H | O | CF₃ | OH |
| Ic1.552 | N | H | O | OCH₃ | OH |
| Ic1.553 | N | H | O | OCH₂CH₃ | OH |
| Ic1.554 | N | H | O | OCHF₂ | OH |
| Ic1.555 | N | H | O | OCF₃ | OH |
| Ic1.556 | N | CH₃ | O | SCH₃ | OH |
| Ic1.557 | N | CH₃ | O | SCH₂CH₃ | OH |
| Ic1.558 | N | CH₃ | O | SO₂CH₃ | OH |
| Ic1.559 | N | CH₃ | O | SO₂CH₂CH₃ | OH |
| Ic1.560 | N | CH₃ | O | SO₂CH(CH₃)₂ | OH |
| Ic1.561 | N | CH₃ | O | SO₂(CH₂)₂CH₃ | OH |
| Ic1.562 | N | CH₃ | O | Cl | OH |
| Ic1.563 | N | CH₃ | O | Br | OH |
| Ic1.564 | N | CH₃ | O | NO₂ | OH |
| Ic1.565 | N | CH₃ | O | CHF₂ | OH |
| Ic1.566 | H | CH₃ | O | CF₃ | OH |
| Ic1.567 | N | CH₃ | O | OCH₃ | OH |
| Ic1.568 | N | CH₃ | O | OCH₂CH₃ | OH |
| Ic1.569 | N | CH₃ | O | OCHF₂ | OH |
| Ic1.570 | N | CH₃ | O | OCF₃ | OH |
| Ic1.571 | N | CH₂CH₃ | O | SCH₃ | OH |
| Ic1.572 | N | CH₂CH₃ | O | SCH₂CH₃ | OH |
| Ic1.573 | N | CH₂CH₃ | O | SO₂CH₃ | OH |
| Ic1.574 | N | CH₂CH₃ | O | SO₂CH₂CH₃ | OH |
| Ic1.575 | N | CH₂CH₃ | O | SO₂CH(CH₃)₂ | OH |
| Ic1.576 | N | CH₂CH₃ | O | SO₂(CH₂)₂CH₃ | OH |
| Ic1.577 | N | CH₂CH₃ | O | Cl | OH |
| Ic1.578 | N | CH₂CH₃ | O | Br | OH |
| Ic1.579 | N | CH₂CH₃ | O | NO₂ | OH |
| Ic1.580 | N | CH₂CH₃ | O | CHF₂ | OH |
| Ic1.581 | N | CH₂CH₃ | O | CF₃ | OH |
| Ic1.582 | N | CH₂CH₃ | O | OCH₃ | OH |
| Ic1.583 | N | CH₂CH₃ | O | OCH₂CH₃ | OH |
| Ic1.584 | N | CH₂CH₃ | O | OCHF₂ | OH |
| Ic1.585 | N | CH₂CH₃ | O | OCF₃ | OH |
| Ic1.586 | N | CH₂Cl | O | SCH₃ | OH |
| Ic1.587 | N | CH₂Cl | O | SCH₂CH₃ | OH |
| Ic1.588 | N | CH₂Cl | O | SO₂CH₃ | OH |
| Ic1.589 | N | CH₂Cl | O | SO₂CH₂CH₃ | OH |
| Ic1.590 | N | CH₂Cl | O | SO₂CH(CH₃)₂ | OH |
| Ic1.591 | N | CH₂Cl | O | SO₂(CH₂)₂CH₃ | OH |
| Ic1.592 | N | CH₂Cl | O | Cl | OH |
| Ic1.593 | N | CH₂Cl | O | Br | OH |
| Ic1.594 | N | CH₂Cl | O | NO₂ | OH |
| Ic1.595 | N | CH₂Cl | O | CHF₂ | OH |
| Ic1.596 | N | CH₂Cl | O | CF₃ | OH |
| Ic1.597 | N | CH₂Cl | O | OCH₃ | OH |
| Ic1.598 | N | CH₂Cl | O | OCH₂CH₃ | OH |
| Ic1.599 | N | CH₂Cl | O | OCHF₂ | OH |
| Ic1.600 | N | CH₂Cl | O | OCF₃ | OH |
| Ic1.601 | N | H | S | SCH₃ | OH |
| Ic1.602 | N | H | S | SCH₂CH₃ | OH |
| Ic1.603 | N | H | S | SO₂CH₃ | OH |
| Ic1.604 | N | H | S | SO₂CH₂CH₃ | OH |
| Ic1.605 | N | H | S | SO₂CH(CH₃)₂ | OH |
| Ic1.606 | N | H | S | SO₂(CH₂)₂CH₃ | OH |
| Ic1.607 | N | H | S | Cl | OH |
| Ic1.608 | N | H | S | Br | OH |
| Ic1.609 | N | H | S | NO₂ | OH |
| Ic1.610 | N | H | S | CHF₂ | OH |
| Ic1.611 | N | H | S | CF₃ | OH |
| Ic1.612 | N | H | S | OCH₃ | OH |
| Ic1.613 | N | H | S | OCH₂CH₃ | OH |
| Ic1.614 | N | H | S | OCHF₂ | OH |
| Ic1.615 | N | H | S | OCF₃ | OH |
| Ic1.616 | N | CH₃ | S | SCH₃ | OH |

TABLE 3-continued

| No. | X | R² | Y | R⁴ | R⁸ |
|---|---|---|---|---|---|
| Ic1.617 | N | CH₃ | S | SCH₂CH₃ | OH |
| Ic1.618 | N | CH₃ | S | SO₂CH₃ | OH |
| Ic1.619 | N | CH₃ | S | SO₂CH₂CH₃ | OH |
| Ic1.620 | N | CH₃ | S | SO₂CH(CH₃)₂ | OH |
| Ic1.621 | N | CH₃ | S | SO₂(CH₂)₂CH₃ | OH |
| Ic1.622 | N | CH₃ | S | Cl | OH |
| Ic1.623 | N | CH₃ | S | Br | OH |
| Ic1.624 | N | CH₃ | S | NO₂ | OH |
| Ic1.625 | N | CH₃ | S | CHF₂ | OH |
| Ic1.626 | N | CH₃ | S | CF₃ | OH |
| Ic1.627 | N | CH₃ | S | OCH₃ | OH |
| Ic1.628 | N | CH₃ | S | OCH₂CH₃ | OH |
| Ic1.629 | N | CH₃ | S | OCHF₂ | OH |
| Ic1.630 | N | CH₃ | S | OCF₃ | OH |
| Ic1.631 | N | CH₂CH₃ | S | SCH₃ | OH |
| Ic1.632 | N | CH₂CH₃ | S | SCH₂CH₃ | OH |
| Ic1.633 | N | CH₂CH₃ | S | SO₂CH₃ | OH |
| Ic1.634 | N | CH₂CH₃ | S | SO₂CH₂CH₃ | OH |
| Ic1.635 | N | CH₂CH₃ | S | SO₂CH(CH₃)₂ | OH |
| Ic1.636 | N | CH₂CH₃ | S | SO₂(CH₂)₂CH₃ | OH |
| Ic1.637 | N | CH₂CH₃ | S | Cl | OH |
| Ic1.638 | N | CH₂CH₃ | S | Br | OH |
| Ic1.639 | N | CH₂CH₃ | S | NO₂ | OH |
| Ic1.640 | N | CH₂CH₃ | S | CHF₂ | OH |
| Ic1.641 | N | CH₂CH₃ | S | CF₃ | OH |
| Ic1.642 | N | CH₂CH₃ | S | OCH₃ | OH |
| Ic1.643 | N | CH₂CH₃ | S | OCH₂CH₃ | OH |
| Ic1.644 | N | CH₂CH₃ | S | OCHF₂ | OH |
| Ic1.645 | N | CH₂CH₃ | S | OCF₃ | OH |
| Ic1.646 | N | CH₂Cl | S | SCH₃ | OH |
| Ic1.647 | N | CH₂Cl | S | SCH₂CH₃ | OH |
| Ic1.648 | N | CH₂Cl | S | SO₂CH₃ | OH |
| Ic1.649 | N | CH₂Cl | S | SO₂CH₂CH₃ | OH |
| Ic1.650 | N | CH₂Cl | S | SO₂CH(CH₃)₂ | OH |
| Ic1.651 | N | CH₂Cl | S | SO₂(CH₂)₂CH₃ | OH |
| Ic1.652 | N | CH₂Cl | S | Cl | OH |
| Ic1.653 | N | CH₂Cl | S | Br | OH |
| Ic1.654 | N | CH₂Cl | S | NO₂ | OH |
| Ic1.655 | N | CH₂Cl | S | CHF₂ | OH |
| Ic1.656 | H | CH₂Cl | S | CF₃ | OH |
| Ic1.657 | N | CH₂Cl | S | OCH₃ | OH |
| Ic1.658 | N | CH₂Cl | S | OCH₂CH₃ | OH |
| Ic1.659 | N | CH₂Cl | S | OCHF₂ | OH |
| Ic1.660 | N | CH₂Cl | S | OCF₃ | OH |
| Ic1.661 | N | H | NCH₃ | SCH₃ | OH |
| Ic1.662 | N | H | NCH₃ | SCH₂CH₃ | OH |
| Ic1.663 | N | H | NCH₃ | SO₂CH₃ | OH |
| Ic1.664 | N | H | NCH₃ | SO₂CH₂CH₃ | OH |
| Ic1.665 | N | H | NCH₃ | SO₂CH(CH₃)₂ | OH |
| Ic1.666 | N | H | NCH₃ | SO₂(CH₂)₂CH₃ | OH |
| Ic1.667 | N | H | NCH₃ | Cl | OH |
| Ic1.668 | N | H | NCH₃ | Br | OH |
| Ic1.669 | N | H | NCH₃ | NO₂ | OH |
| Ic1.670 | N | H | NCH₃ | CHF₂ | OH |
| Ic1.671 | N | H | NCH₃ | CF₃ | OH |
| Ic1.672 | N | H | NCH₃ | OCH₃ | OH |
| Ic1.673 | N | H | NCH₃ | OCH₂CH₃ | OH |
| Ic1.674 | N | H | NCH₃ | OCHF₂ | OH |
| Ic1.675 | N | H | NCH₃ | OCF₃ | OH |
| Ic1.676 | N | CH₃ | NCH₃ | SCH₃ | OH |
| Ic1.677 | N | CH₃ | NCH₃ | SCH₂CH₃ | OH |
| Ic1.678 | N | CH₃ | NCH₃ | SO₂CH₃ | OH |
| Ic1.679 | N | CH₃ | NCH₃ | SO₂CH₂CH₃ | OH |
| Ic1.680 | N | CH₃ | NCH₃ | SO₂CH(CH₃)₂ | OH |
| Ic1.681 | N | CH₃ | NCH₃ | SO₂(CH₂)₂CH₃ | OH |
| Ic1.682 | N | CH₃ | NCH₃ | Cl | OH |
| Ic1.683 | N | CH₃ | NCH₃ | Br | OH |
| Ic1.684 | N | CH₃ | NCH₃ | NO₂ | OH |
| Ic1.685 | N | CH₃ | NCH₃ | CHF₂ | OH |
| Ic1.686 | N | CH₃ | NCH₃ | CF₃ | OH |
| Ic1.687 | N | CH₃ | NCH₃ | OCH₃ | OH |
| Ic1.688 | N | CH₃ | NCH₃ | OCH₂CH₃ | OH |
| Ic1.689 | N | CH₃ | NCH₃ | OCHF₂ | OH |
| Ic1.690 | N | CH₃ | NCH₃ | OCF₃ | OH |
| Ic1.691 | N | CH₂CH₃ | NCH₃ | SCH₃ | OH |
| Ic1.692 | N | CH₂CH₃ | NCH₃ | SCH₂CH₃ | OH |
| Ic1.693 | N | CH₂CH₃ | NCH₃ | SO₂CH₃ | OH |
| Ic1.694 | N | CH₂CH₃ | NCH₃ | SO₂CH₂CH₃ | OH |
| Ic1.695 | N | CH₂CH₃ | NCH₃ | SO₂CH(CH₃)₂ | OH |
| Ic1.696 | N | CH₂CH₃ | NCH₃ | SO₂(CH₂)₂CH₃ | OH |
| Ic1.697 | N | CH₂CH₃ | NCH₃ | Cl | OH |
| Ic1.698 | N | CH₂CH₃ | NCH₃ | Br | OH |
| Ic1.699 | N | CH₂CH₃ | NCH₃ | NO₂ | OH |
| Ic1.700 | N | CH₂CH₃ | NCH₃ | CHF₂ | OH |
| Ic1.701 | N | CH₂CH₃ | NCH₃ | CF₃ | OH |
| Ic1.702 | N | CH₂CH₃ | NCH₃ | OCH₃ | OH |
| Ic1.703 | N | CH₂CH₃ | NCH₃ | OCH₂CH₃ | OH |
| Ic1.704 | N | CH₂CH₃ | NCH₃ | OCHF₂ | OH |
| Ic1.705 | N | CH₂CH₃ | NCH₃ | OCF₃ | OH |
| Ic1.706 | N | CH₂Cl | NCH₃ | SCH₃ | OH |
| Ic1.707 | N | CH₂Cl | NCH₃ | SCH₂CH₃ | OH |
| Ic1.708 | N | CH₂Cl | NCH₃ | SO₂CH₃ | OH |
| Ic1.709 | N | CH₂Cl | NCH₃ | SO₂CH₂CH₃ | OH |
| Ic1.710 | N | CH₂Cl | NCH₃ | SO₂CH(CH₃)₂ | OH |
| Ic1.711 | N | CH₂Cl | NCH₃ | SO₂(CH₂)₂CH₃ | OH |
| Ic1.712 | N | CH₂Cl | NCH₃ | Cl | OH |
| Ic1.713 | N | CH₂Cl | NCH₃ | Br | OH |
| Ic1.714 | N | CH₂Cl | NCH₃ | NO₂ | OH |
| Ic1.715 | N | CH₂Cl | NCH₃ | CHF₂ | OH |
| Ic1.716 | N | CH₂Cl | NCH₃ | CF₃ | OH |
| Ic1.717 | N | CH₂Cl | NCH₃ | OCH₃ | OH |
| Ic1.718 | N | CH₂Cl | NCH₃ | OCH₂CH₃ | OH |
| Ic1.719 | N | CH₂Cl | NCH₃ | OCHF₂ | OH |
| Ic1.720 | N | CH₂Cl | NCH₃ | OCF₃ | OH |

Most particular preference is also given to the compounds of the formula Ic2, in particular to the compounds Ic2.1 to Ic2.720 which differ from the corresponding compounds Ic1.1 to Ic1.720 in that $R^{14}$ is methyl.

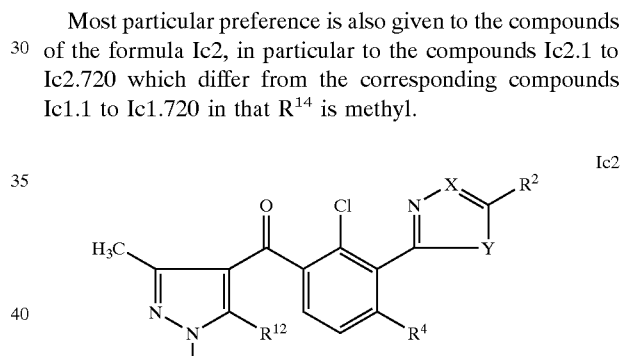

Most particular preference is also given to the compounds of the formula Ic3, in particular to the compounds Ic3.1 to Ic3.720 which differ from the compounds Ic1.1 to Ic1.720 in that $R^{13}$ is cyclopentyl.

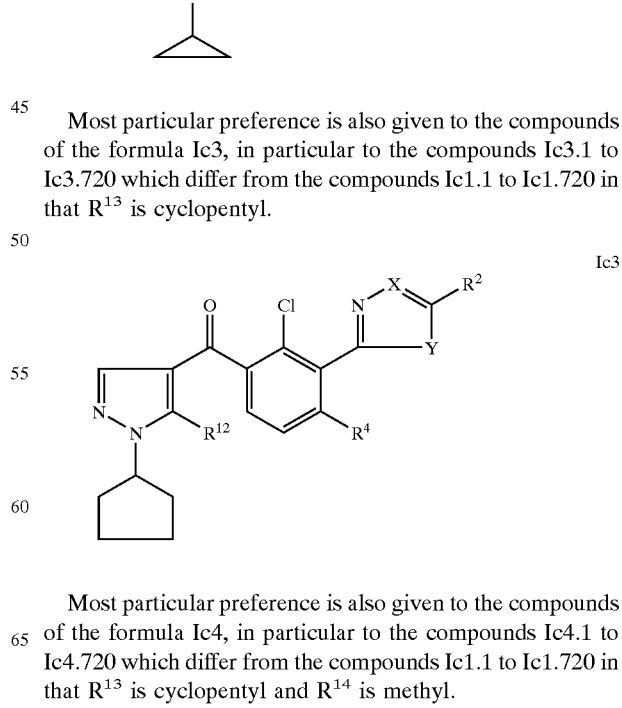

Most particular preference is also given to the compounds of the formula Ic4, in particular to the compounds Ic4.1 to Ic4.720 which differ from the compounds Ic1.1 to Ic1.720 in that $R^{13}$ is cyclopentyl and $R^{14}$ is methyl.

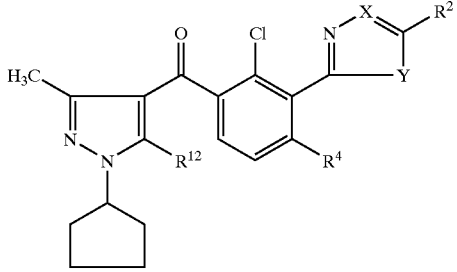

Ic4

Most particular preference is also given to the compounds of the formula Ic5, in particular to the compounds Ic5.1 to Ic5.720 which differ from the compounds Ic1.1 to Ic1.720 in that $R^{13}$ is cyclohexyl.

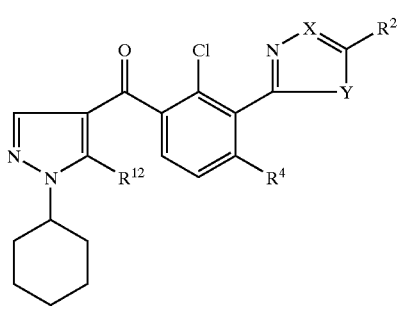

Ic5

Most particular preference is also given to the compounds of the formula Ic6, in particular to the compounds Ic6.1 to Ic6.720 which differ from the compounds Ic1.1 to Ic1.720 in that $R^{13}$ is cyclohexyl and $R^{14}$ is Methyl.

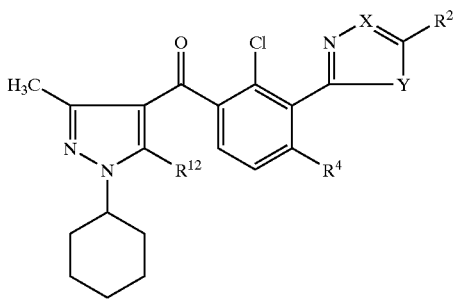

Ic6

Most particular preference is also given to the compounds of the formula Ic7, in particular to the compounds Ic7.1 to Ic7.720 which differ from the compounds Ic1.1 to Ic1.720 in that $R^{13}$ is 2-norbornyl.

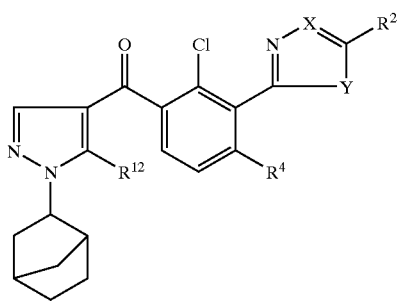

Ic7

Most particular preference is also given to the compounds of the formula Ic8, in particular to the compounds Ic8.1 to Ic8.720 which differ from the compounds Ic1.1 to Ic1.720 in that $R^{13}$ is 2-norbornyl and $R^{14}$ is methyl.

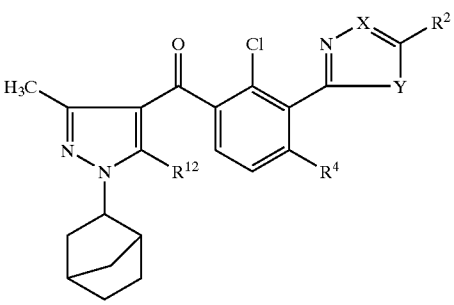

Ic8

Most particular preference is also given to the compounds of the formula Ic9, in particular to the compounds Ic9.1 to Ic9.720 which differ from the compounds Ic1.1 to Ic1.720 in that $R^{13}$ is 2-adamantyl.

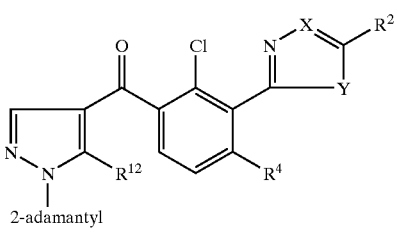

Ic9

Most particular preference is also given to the compounds of the formula Ic10, in particular to the compounds Ic10.1 to Ic10.720 which differ from the compounds Ic1.1 to Ic1.720 in that $R^{13}$ is 2-adamantyl and $R^{14}$ is methyl.

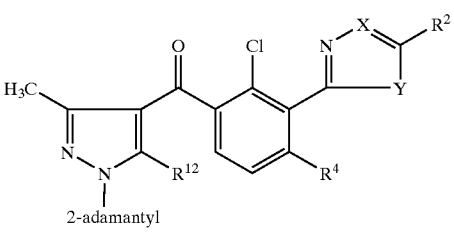

Ic10

Most particular preference is also given to the compounds of the formula Ic11, in particular to the compounds Ic11.1 to Ic11.720 which differ from the corresponding compounds Ic1.1 to Ic1.720 in that $R^1$ is methyl.

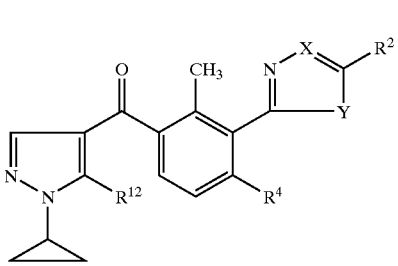

Ic11

Most particular preference is also given to the compounds of the formula Ic12, in particular to the compounds Ic12.1 to Ic12.720 which differ from the corresponding compounds Ic1.1 to Ic1.720 in that $R^1$ is methyl and $R^{14}$ is methyl.

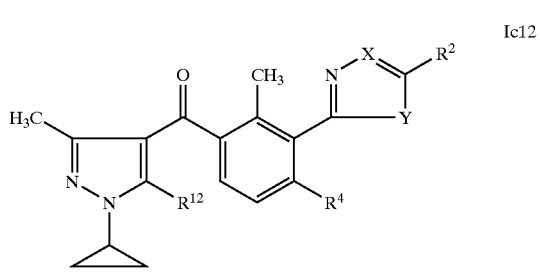

Most particular preference is also given to the compounds of the formula Ic13, in particular to the compounds Ic13.1 to Ic13.720 which differ from the compounds Ic1.1 to Ic1.720 in that $R^1$ is methyl and $R^{13}$ is cyclopentyl.

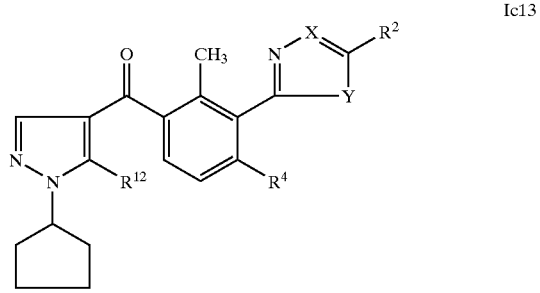

Most particular preference is also given to the compounds of the formula Ic14, in particular to the compounds Ic14.1 to Ic14.720 which differ from the compounds Ic1.1 to Ic1.720 in that $R^1$ is methyl, $R^{13}$ is cyclopentyl and $R^{14}$ is methyl.

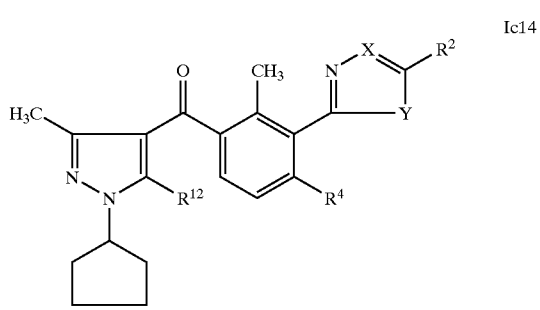

Most particular preference is also given to the compounds of the formula Ic15, in particular to the compounds Ic15.1 to Ic15.720 which differ from the compounds Ic1.1 to Ic1.720 in that $R^1$ is methyl and $R^{13}$ is cyclohexyl.

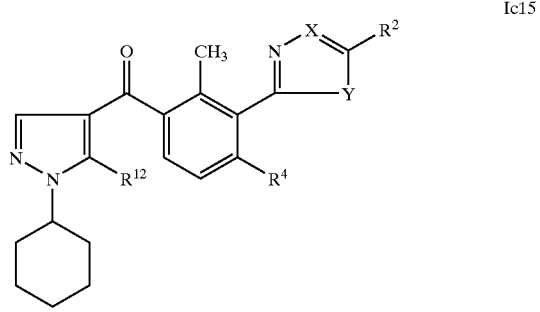

Most particular preference is also given to the compounds of the formula Ic16, in particular to the compounds Ic16.1 to Ic16.720 which differ from the compounds Ic1.1 to Ic1.720 in that $R^1$ is methyl, $R^{13}$ is cyclohexyl and $R^{14}$ is methyl.

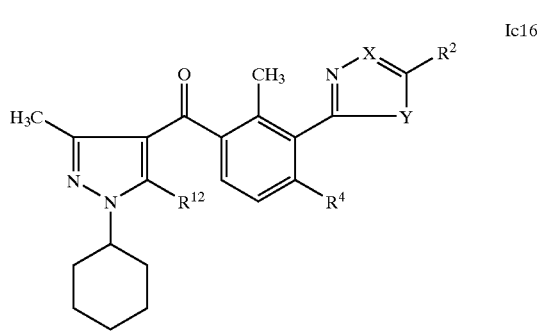

Most particular preference is also given to the compounds of the formula Ic17, in particular to the compounds Ic17.1 to Ic17.720 which differ from the compounds Ic1.1 to Ic1.720 in that $R^1$ is methyl and $R^{13}$ is 2-norbornyl.

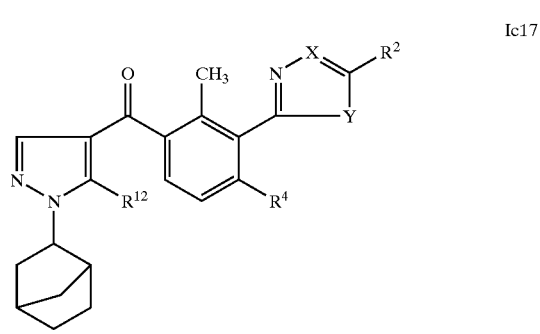

Most particular preference is also given to the compounds of the formula Ic18, in particular to the compounds Ic18.1 to Ic18.720 which differ from the compounds Ic1.1 to Ic1.720 in that $R^1$ is methyl, $R^{13}$ is 2-norbornyl and $R^{14}$ is methyl.

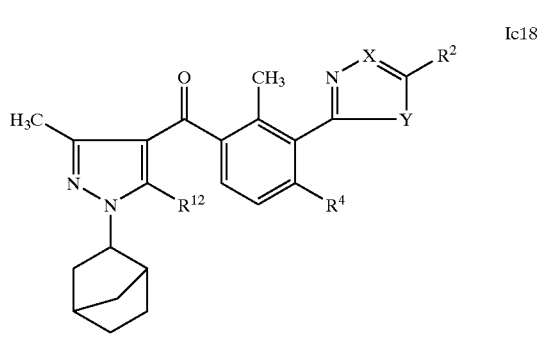

Most particular preference is also given to the compounds of the formula Ic19, in particular to the compounds Ic19.1 to Ic19.720 which differ from the compounds Ic1.1 to Ic1.720 in that $R^1$ is methyl and $R^{13}$ is 2-adamantyl.

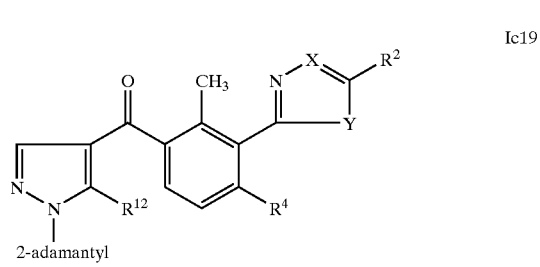

Most particular preference is also given to the compounds of the formula Ic20, in particular to the compounds Ic20.1 to Ic20.720 which differ from the compounds Ic1.1 to Ic1.720 in that $R^1$ is methyl, $R^{13}$ is 2-adamantyl and $R^{14}$ is methyl.

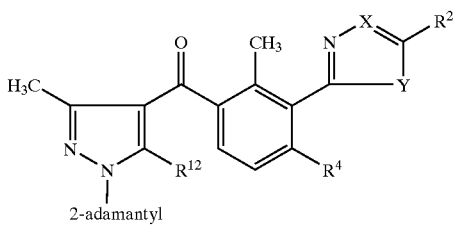

Ic20

Most particular preference is also given to the compounds of the formula Ic21, in particular to the compounds Ic21.1 to Ic21.720 which differ from the corresponding compounds Ic1.1 to Ic1.720 in that $R^1$ is methoxy.

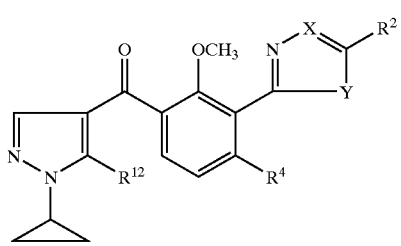

Ic21

Most particular preference is also given to the compounds of the formula Ic22, in particular to the compounds Ic22.1 to Ic22.720 which differ from the corresponding compounds Ic1.1 to Ic1.720 in that $R^1$ is methoxy and $R^{14}$ is methyl.

Ic22

Most particular preference is also given to the compounds of the formula Ic23, in particular to the compounds Ic23.1 to Ic23.720 which differ from the compounds Ic1.1 to Ic1.720 in that $R^1$ is methoxy and $R^{13}$ is cyclopentyl.

Ic23

Most particular preference is also given to the compounds of the formula Ic24, in particular to the compounds Ic24.1 to Ic24.720 which differ from the compounds Ic1.1 to Ic1.720 in that $R^1$ is methoxy, $R^{13}$ is cyclopentyl and $R^{14}$ is methyl.

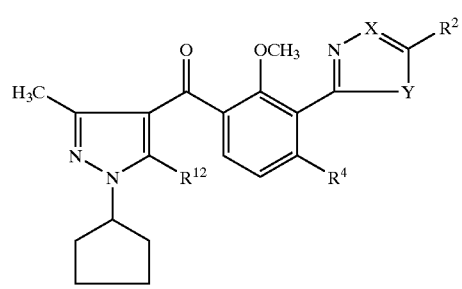

Ic24

Most particular preference is also given to the compounds of the formula Ic25, in particular to the compounds Ic25.1 to Ic25.720 which differ from the compounds Ic1.1 to Ic1.720 in that $R^1$ is methoxy and $R^{13}$ is cyclohexyl.

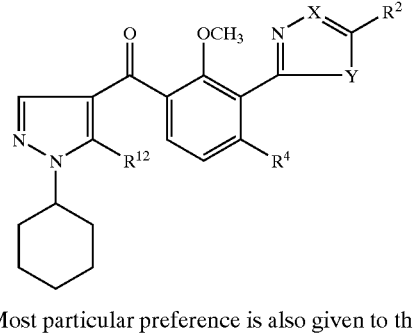

Ic25

Most particular preference is also given to the compounds of the formula Ic26, in particular to the compounds Ic26.1 to Ic26.720 which differ from the compounds Ic1.1 to Ic1.720 in that $R^1$ is methoxy, $R^{13}$ is cyclohexyl and $R^{14}$ is methyl.

Ic26

Most particular preference is also given to the compounds of the formula Ic27, in particular to the compounds Ic27.1 to Ic27.720 which differ from the compounds Ic1.1 to Ic1.720 in that $R^1$ is methoxy and $R^{13}$ is 2-norbornyl.

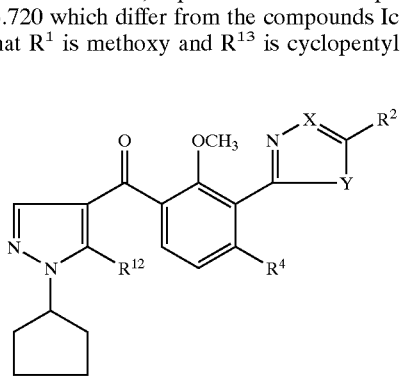

Ic27

Most particular preference is also given to the compounds of the formula Ic28, in particular to the compounds Ic28.1 to Ic28.720 which differ from the compounds Ic1.1 to Ic1.720 in that $R^1$ is methoxy, $R^{13}$ is 2-norbornyl and $R^{14}$ is methyl.

Ic28

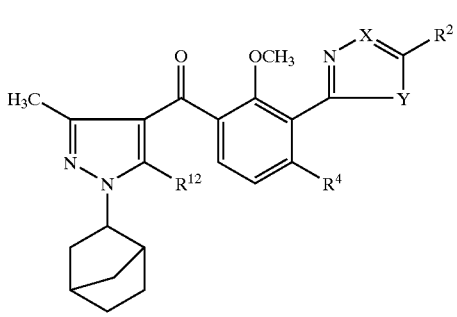

Most particular preference is Also given to the compounds of the formula Ic29, in particular to the compounds Ic29.1 to Ic29.720 which differ from the compounds Ic1.1 to Ic1.720 in that $R^1$ is methoxy and $R^{13}$ is 2-adamantyl.

Ic29

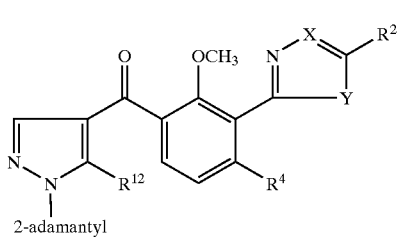

Most particular preference is also given to the compounds of the formula Ic30, in particular to the compounds Ic30.1 to Ic30.720 which differ from the compounds Ic1.1 to Ic1.720 in that $R^1$ is methoxy, $R^{13}$ is 2-adamantyl and $R^{14}$ is methyl.

Ic30

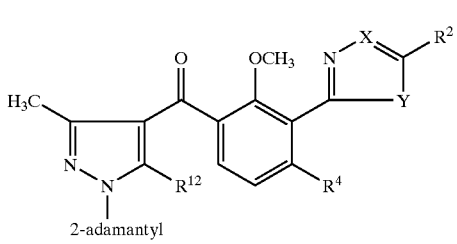

The 1-cycloalkylpyrazolylbenzoyl derivatives of the formula I can be obtained by various routes, for example by the processes below.

Process A

Reaction of pyrazoles of the formula II with an activated benzoic acid IIIα or a benzoic acid IIIβ, which is preferably activated in situ, to give the corresponding acylation product IV, followed by rearrangement, gives compounds of the formula I where $R^{12}$=OH.

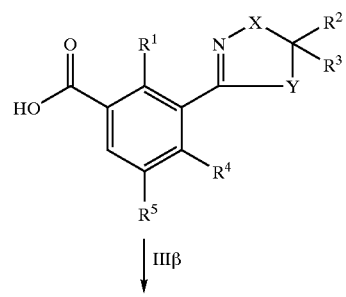

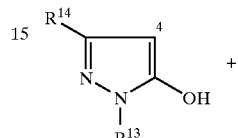

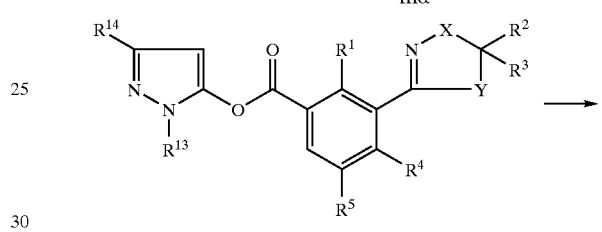

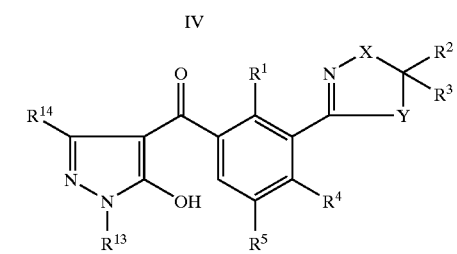

I where $R^{12}$ = OH $L^1$ is a nucleophilically displaceable leaving group, such as halogen, for example bromine, chlorine, hetaryl, for example imidazolyl, pyridyl, carboxylate, for example acetate, trifluoroacetate, etc.

The activated benzoic acid can be employed directly, such as in the case of the benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

It may be advantageous to carry out the acylation reaction in the presence of a base. The reactants and the auxiliary base are advantageously employed in this case in equimolar amounts. A slight excess of auxiliary base, for example from 1.2 to 1.5 molar equivalents, based on II, may be advantageous in certain cases.

Suitable auxiliary bases are tertiary alkylamines, pyridine or alkali metal carbonates. Suitable for use as solvents are, for example, chlorinated hydrocarbons, such as methylene chloride, 1,2-dichloroethane, aromatic hydrocarbons, such as toluene, xylene, chlorobenzene, ethers, such as diethyl ether, methyl tert-butyl ether, dimethoxyethane, tetrahydrofuran, dioxane, polar aprotic solvents, such as acetonitrile, dimethylformamide, dimethyl sulfoxide, or esters, such as ethyl acetate, or mixtures of these.

If the activated carboxylic acid component used is a benzoyl halide, it may be advantageous to cool the reaction mixture to 0–10° C. when adding this reaction partner. The mixture is subsequently stirred at 20–100° C., preferably at 25–50° C., until the reaction has ended. work-up is carried out in a customary manner, for example by pouring the reaction mixture into water and extracting the product of value. Solvents which are particularly suitable for this purpose are methylene chloride, diethyl ether, dimethoxyethane and ethyl acetate. The organic phase is dried and the solvent is removed, after which the crude ester can be employed for the rearrangement without any further purification.

The rearrangement of the esters to the compounds of the formula I is advantageously carried out at 20–40° C. in a solvent and in the presence of a base and, if appropriate, using a cyano compound as catalyst.

Suitable solvents are, for example, acetonitrile, methylene chloride, 1,2-dichlorcethane, dioxane, ethyl acetate, dimethoxyethane, toluene or mixtures of these. Preferred solvents are acetonitrile and dioxane.

Suitable bases are tertiary amines, such as triethylamine or pyridine, or alkali metal carbonates, such as sodium carbonate or potassium carbonate, which are preferably employed in an equimolar amount or an up to four-fold excess, based on the ester. Preference is given to using triethylamine or alkali metal carbonates, preferably in twice the equimolar amount, based on the ester.

Suitable cyano compounds are inorganic cyanides, such as sodium cyanide and potassium cyanide, and organic cyano compounds, such as acetone cyanohydrin and trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up can be carried out in the manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, and the mixture is dried and concentrated. (Examples for the preparation of esters of hydroxypyrazoles and for the rearrangement of the esters are given, for example, in EP-A 282 944 and U.S. Pat. No. 4,643,757).

However, it is also possible to generate the "acylation product" IV in situ by reacting a pyrazole of the formula II, or an alkali metal salt thereof with a 3-(heterocyclyl)benzene derivative of the formula V in the presence of carbon monoxide, a catalyst and a base.

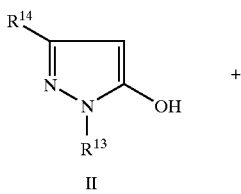

II

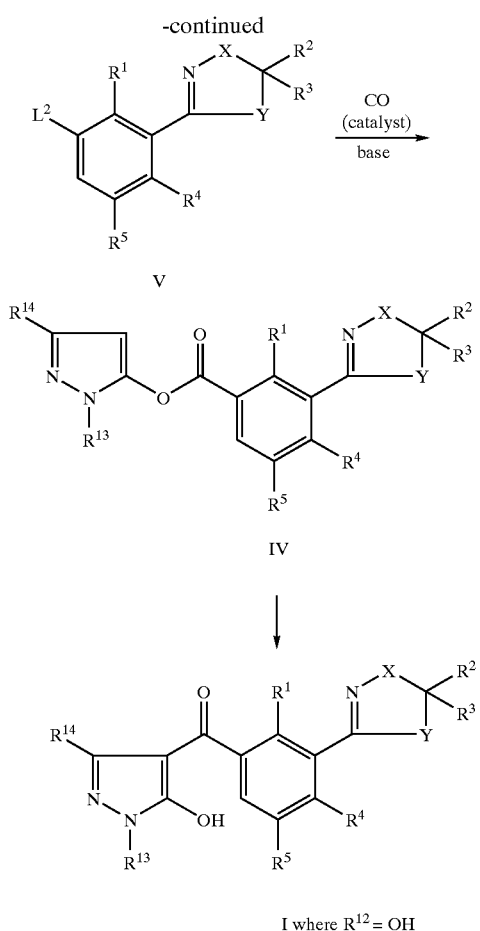

I where $R^{12}$ = OH $L^2$ is a leaving group, such as halogen, for example chlorine, bromine or iodine, or sulfonate, such as mesylate or triflate; preference is given to bromine or triflate.

The "acylation product" IV proceeds to react, directly or indirectly, to give the 1-cycloalkylpyrazolylbenzoyl derivative of the formula I.

Suitable catalysts are palladium-ligand complexes in which the palladium is present in oxidation state 0, metallic palladium, which has optionally been absorbed on a carrier, and preferably palladium(II) salts. The reaction with palladium(II) salts and metallic palladium is preferably carried out in the presence of complex ligands.

An example of a suitable palladium(0)-ligand complex is tetrakis(triphenylphosphine)palladium.

Metallic palladium is preferably absorbed on an inert carrier such as, for example, activated carbon, silica, alumina, barium sulfate or calcium carbonate. The reaction is preferably carried out in the presence of complex ligands such as, for example; triphenylphosphine.

Examples of suitable palladium(II) salts are palladium acetate and palladium chloride. The presence of complex ligands such as, for example, triphenylphosphine is preferred.

Suitable complex ligands for the palladium-ligand complexes, or in whose presence the reaction is preferably carried out with metallic palladium or palladium(II) salts, are tertiary phosphines whose structure is represented by the following formulae:

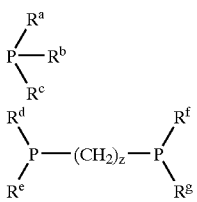

where z is 1 to 4 and the radicals $R^a$ to $R^g$ are $C_1$–$C_6$-alkyl, $C_3$–$C_6$-cycloalkyl, aryl-$C_1$–$C_2$-alkyl or, preferably, aryl. Aryl is, for example, naphthyl and unsubstituted or substituted phenyl such as, for example, 2-tolyl and, in particular, unsubstituted phenyl.

The complex palladium salts can be prepared in a manner known per se starting from commercially available palladium salts such as palladium chloride or palladium acetate and the appropriate phosphines such as, for example, triphenylphosphine or 1,2-bis(diphenylphosphino)ethane. Many of the complexed palladium salts are commercially available. Preferred palladium salts are [(R)(+)2,2'-bis(diphenylphosphino)-1,1'-binaphthyl]palladium(II) chloride, bis(triphenylphosphine)palladium(II) acetate and, in particular, bis(triphenylphosphine)palladium(II) chloride.

The palladium catalyst is usually employed in a concentration of from 0.05 to 5 mol %, and preferably 1–3 mol %.

Suitable bases are tertiary amines, such as, for example, N-methylpiperidine, ethyldiisopropylamine, 1,8-bisdimethylaminonaphthalene or, in particular, triethylamine. Also suitable is alkali metal carbonate, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on the 3-(heterocylyl)benzene derivative of the formula V.

Suitable solvents are nitriles, such as benzonitrile and acetonitrile, amides, such as dimethylformide, dimethylacetamide, tetra-$C_1$–$C_4$-alkylureas or N-methylpyrrolidone and, preferably, ethers, such as tetrahydrofuran and methyl tert-butyl ethers. Particular preference is given to ethers, such as 1,4-dioxane and dimethoxyethane.

Process B

Compounds of the formula I where $R^{12}$=hydroxyl are obtained by reacting compounds of the formula I where $R^{12}$=hydroxyl with alkylating agents, sulfonylating agents or acylating agents $L^3$–$R^{12a}$(VI)

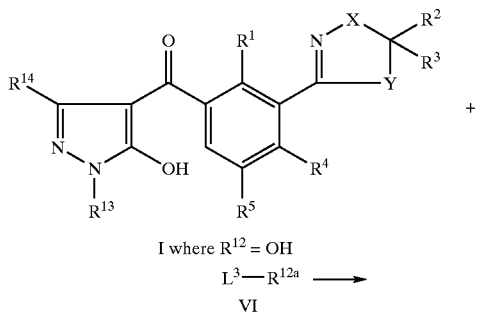

I where $R^{12}$ = OH $L^3$—$R^{12a}$ ⟶

VI

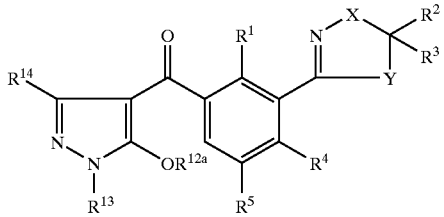

I where $R^{12}$ = $OR^{12a}$ (≡ $R^{12}$ + OH)

$L^3$ is a nucleophilically displaceable leaving group, such as halogen, for example bromine or chlorine, acyloxy, for example acetyloxy or ethylcarbonyloxy, or alkylsulfonyloxy, for example methylsulfonyloxy or trifluoromethylsulfonyloxy.

$R^{12a}$ is $C_1$–$C_6$-alkyl, $C_3$–$C_6$-alkenyl, $C_1$–$C_6$-alkylsulfonyl, $C_1$–$C_6$-alkylcarbonyl, phenylsulfonyl or phenylcarbonyl, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

The compounds of the formula VI can be employed directly, such as, for example, in the case of the sulfonyl halides or sulfonic anhydrides, or be generated in situ, for example activated sulfonic acids (using sulfonic acid and dicyclohexylcarbonyldiimide, carbonyldiimidazole, etc.).

The starting materials are generally employed in equimolar amounts. However, it may also be advantageous to employ an excess of one or the other component.

If appropriate, it may be advantageous to carry out the reaction in the presence of a base. The reactants and the auxiliary base are advantageously employed in equimolar amounts. An excess of auxiliary base, for example from 1.5 to 3 molar equivalents, based on I, may be advantageous in certain cases.

Suitable auxiliary bases are tertiary alkylamines, such as triethylamine, pyridine, alkali metal carbonates, for example sodium carbonate or potassium carbonate, and alkali metal hydrides, for example sodium hydride. Preference is given to using triethylamine and pyridine.

Suitable solvents are, for example, chlorinated hydrocarbons, such as methylene chloride and 1,2-dichloroethane, aromatic hydrocarbons, for example toluene, xylene, chlorobenzene, ethers, such as diethyl ether, methyl tert-butyl ether, tetrahydrofuran and dioxane, polar aprotic solvents, such as acetonitrile, dimethylformamide, dimethyl sulfoxide, or esters, such as ethyl acetate, or mixtures of these.

In general, the reaction temperature is in the range from 0° C. to the boiling point of the reaction mixture.

Work-up can be carried out in the manner known per se to give the product.

The pyrazoles of the formula II used as starting materials are known or can be prepared by processes known per se (for example EP-A 240 001 and J. Prakt. Chem. 315, 383 (1973)). The activated benzoic acids IIIα and the benzoic acids IIIβ are likewise known or can be prepared in the manner known per se (for example WO 96/26206). Furthermore, the 3-(heterocyclyl)benzene derivatives of the formula V are known or can be prepared in the manner known per se (PCT/EP/99/03006).

PREPARATION EXAMPLE
4-[2-Methyl-3-(4,5-dihydroisoxazol-3-yl)-4-methylsulfonylbenzoyl]-1-cyclopentyl-5-hydroxy-1H-pyrazole (compound 4.6)

1.9 g (9.4 mmol) of dicyclohexylcarbodiimide and 1.3 g (8.8 mmol) of 1-cyclopentyl-5-hydroxy-1H-pyrazole were added to a solution of 2.5 g (8.8 mmol) of 2-methyl-3-(4,5-dihydroisoxazol-3-yl)-4-methylsulfonylbenzoic acid in 100 ml of dioxane, and the mixture was stirred at room temperature for 12 hours. Solid components were then filtered off and the filtrate was admixed with 1.5 g (10 mmol)

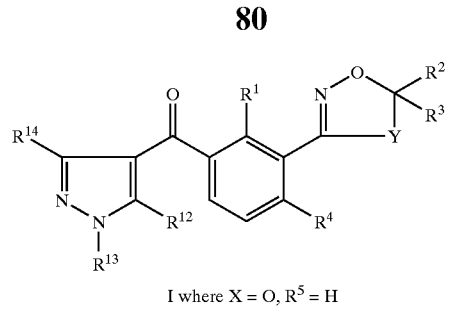

I where X = O, $R^5$ = H

TABLE 4

| No. | $R^1$ | $R^2$ | $R^3$ | Y | $R^4$ | $R^{12}$ | $R^{13}$ | $R^{14}$ | physical data m.p. [° C.]; $^1$H-NMR [δ in ppm] |
|---|---|---|---|---|---|---|---|---|---|
| 4.1 | Cl | H | H | $CH_2$ | $SO_2CH_3$ | OH | cyclopentyl | H | 192–197 |
| 4.2 | Cl | H | H | $CH_2$ | $SO_2CH_3$ | $OCOC_6H_5$ | cyclopentyl | H | 235–240 |
| 4.3 | Cl | H | H | $CH_2$ | $SO_2CH_3$ | $OCO(3\text{-}F\text{—}C_6H_4)$ | cyclopentyl | H | 220–225 |
| 4.4 | Cl | H | H | $CH_2$ | $SO_2CH_3$ | $OCH_3$ | cyclopentyl | H | 195–200 |
| 4.5 | Cl | H | H | $CH_2$ | $SO_2CH_3$ | $OCH_2CH_3$ | cyclopentyl | H | 145–150 |
| 4.6 | $CH_3$ | H | H | $CH_2$ | $SO_2CH_3$ | OH | cyclopentyl | H | 135–140 |
| 4.7 | $CH_3$ | H | H | $CH_2$ | $SO_2CH_3$ | $OCO(3\text{-}F\text{—}C_6H_4)$ | cyclopentyl | H | 1.4–2.0 (m, 8H); 2.0(s, 3H); 3.2 (m, 2H); 4.4(m, 2H); 4.8(m, 1H); 7.6–7.8(m, 7H) |
| 4.8 | $CH_3$ | H | H | $CH_2$ | $SO_2CH_3$ | $OCH(CH_3)_2$ | cyclopentyl | H | 1.2 (d, 6H); 1.4–2.0(m, 8H); 2.7 (s, 3H); 2.9(s, 3H); 3.3(br, 2H); 4.5 (t, 2H), 4.8(br, 1H); 4.9(m, 1H); 7.5 (s, 1H); 7.7(d, 1H); 7.9(d, 1H) |
| 4.9 | Cl | H | H | $CH_2$ | $SO_2CH_3$ | OH | 2-norbornyl | H | 135–140 |
| 4.10 | $CH_3$ | H | H | $CH_2$ | $SO_2CH_3$ | OH | 2-norbornyl | H | 110–115 |
| 4.11 | Cl | H | H | $CH_2$ | $SO_2CH_3$ | $OCOC_6H_5$ | 2-norbornyl | H | 200–205 |
| 4.12 | Cl | H | H | $CH_2$ | $SO_2CH_3$ | $OCO(3\text{-}F\text{—}C_6H_4)$ | 2-norbornyl | H | 85–90 |
| 4.13 | $CH_3$ | H | H | $CH_2$ | $SO_2CH_3$ | $OCOC_6H_5$ | 2-norbornyl | H | 1.0–2.5(m, 10H); 2.1(s, 3H); 3.0 (s, 3H); 3.2(t, 2H); 4.2–4.7(m, 3H); 7.4–8.2(m, 8H) |
| 4.14 | $CH_3$ | H | H | $CH_2$ | $SO_2CH_3$ | $OCO(3\text{-}F\text{—}C_6H_4)$ | 2-norbornyl | H | 1.0–2.6(m, 10H); 2.1(s, 3H); 3.01 (s, 3H); 3.21(t, 2H), 4.3–4.7(m, 3H); 7.4–8.0(m, 7H) |
| 4.15 | Cl | H | H | $CH_2$ | $SO_2CH_3$ | OH | 2-adamantyl | H | 120–125 |
| 4.16 | $CH_3$ | H | H | $CH_2$ | $SO_2CH_3$ | OH | 2-adamantyl | H | 140–145 |
| 4.17 | Cl | H | H | $CH_2$ | $SO_2CH_3$ | OH | cyclopropyl | H | 227–228 |
| 4.19 | $OCH_3$ | H | H | $CH_2$ | $SO_2CH_3$ | OH | cyclopropyl | H | 197–199 |
| 4.19 | Cl | H | H | $CH_2$ | $SO_2CH_3$ | $OSO_2(4\text{-}CH_3\text{—}C_6H_4)$ | cyclopropyl | H | 81–82 |
| 4.20 | Cl | H | H | $CH_2$ | $SO_2CH_3$ | $OCH(CH_3)_2$ | cyclopropyl | H | 179–190 |
| 4.21 | Cl | H | H | $CH_2$ | $SO_2CH_3$ | $OCOC_6H_5$ | cyclopropyl | H | oil |
| 4.22 | Cl | H | H | $CH_2$ | $SO_2CH_3$ | $OCO(3\text{-}F\text{—}C_6H_4)$ | cyclopropyl | H | 198–200 |
| 4.23 | $OCH_3$ | H | H | $CH_2$ | $SO_2CH_3$ | OH | cyclopropyl | H | 160–161 |
| 4.24 | $CH_3$ | H | H | $CH_2$ | $SO_2CH_3$ | OH | cyclopropyl | H | 178–179 | of potassium carbonate and refluxed for 4 hours. The solvent was removed, the residue was then taken up in water and the mixture was washed with ethyl acetate, and then adjusted to pH 3 using 10% strength hydrochloric acid and extracted with methylene chloride. The solvent of the resulting organic phase was distilled off, the residue was taken up in 300 ml of aqueous potassium carbonate solution, insoluble components were filtered off, the pH was adjusted to 3 using 10% strength hydrochloric acid and the resulting precipitate was separated off and dried. Yield: 1.5 g (42% of theory) of 4-[2-methyl-3-(4,5-dihydro-isoxazol-3-yl)-4-methylsulfonylbenzoyl]-1-cyclopentyl-5-hydroxy-1H-pyrazole M.p.: 135–140° C.

In addition to the compound above, Table 4 lists other 1-cycloalkylpyrazolylbenzoyl derivatives of the formula I which were prepared or are preparable in a similar manner;

The 1-cycloalkylpyrazolylbenzoyl derivatives of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I, or the herbicidal. compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. altissima, *Beta vulgaris* spec. rapa, *Brassica napus* var. napus, *Brassica*

*napus* var. *napobrassica*, *Brassica rapa* var. *silvestris*, *Camellia sinensis*, *Carthamus tinctorius*, *Carya illinoinensis*, *Citrus limon*, *Citrus sinensis*, *Coffea arabica* (*Coffea canephora*, *Coffea liberica*), *Cucumis sativus*, *Cynodon dactylon*, *Daucus carota*, *Elaeis guineensis*, *Fragaria vesca*, *Glycine max*, *Gossypium hirsutum*, (*Gossypium arboreum*, *Gossypium herbaceum*, *Gossypium vitifolium*), *Helianthus annuus*, *Hevea brasiliensis*, *Hordeum vulgare*, *Humulus lupulus*, *Ipomoea batatas*, *Juglans regia*, *Lens culinaris*, *Linum usitatissimum*, *Lycopersicon lycopersicum*, Malus spec., *Manihot esculenta*, *Medicago sativa*, Musa spec., *Nicotiana tabacum* (*N. rustica*), *Olea europaea*, *Oryza sativa*, *Phaseolus lunatus*, *Phaseolus vulgaris*, *Picea abies*, Pinus spec., *Pisum sativum*, *Prunus avium*, *Prunus persica*, *Pyrus communis*, *Ribes sylvestre*, *Ricinus communis*, *Saccharum officinarum*, *Secale cereale*, *Solanum tuberosum*, *Sorghum bicolor* (*S. vulgare*), *Theobroma cacao*, *Trifolium pratense*, *Triticum aestivum*, *Triticum durum*, *Vicia faba*, *Vitis vinifera* and *Zea mays*.

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusting agents, materials for broadcasting or granules, by means of spraying, atomizing, dusting, broadcasting or watering. The use forms depend on the intended aims; in any case, they should ensure the finest distribution possible of the active compounds according to the invention.

The herbicidal compositions comprise a herbicidally effective amount of at least one compound of the formula I or an agriculturally useful salt of I, and auxiliaries which are customarily used for formulating of crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ether, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol asters, lignin-sulfite waste liquors or methylcellulose.

Powders, materials for broadcasting and dusting agents can be prepared by mixing or grinding the active compounds together with a solid carrier.

Granules, e.g. coated granules, impregnated granules and homogeneous granules, can be prepared by binding the active compounds to solid carriers solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise about from 0.001 to 98% by weight, preferably 0.01 to 95% by weight of at least one active compound. The active compounds are employed in a purity of from 90% to 100%, preferably 95% to 100% (according to the NMR spectrum).

The following formulation examples illustrate the preparation of such formulations:

I. 20 parts by weight of compound No. 4.6 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of compound no. 4.6 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of compound No. 4.6 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of compound No. 4.6 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill.

Finely distributing the mixture in 20,000 parts by weight of water gives a spray mixture which comprises 0.1% by weight of the active compound.

V. 3 parts by weight of compound No. 4.6 are mixed with 97 parts by weight of finely divided kaolin. This gives a dust which comprises 3% by weight of the active compound.

VI. 20 parts by weight of compound No. 4.6 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of compound No. 4.6 is dissolved in a mixture composed of 70 parts by weight of cyclohexanone, 20 parts by weight of etboxylated isooctylphenol and 10 parts by weight of ethoxylated castor oil. This gives a stable emulsion concentrate.

VIII. 1 part by weight of compound No. 4.6 of the formula I is dissolved in a mixture composed of 80 parts by weight of cyclohexanone and 20 parts by weight of Wettol® EM 31 (=nonionic emulsifier based on ethoxylated castor oil).

This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of compound of the formula I are from 0.001 to 3.0, preferably 0.01 to 1.0 kg/ha of active substance (a.s.), depending on the control target, the season, the target plants and the growth stage.

To widen the activity spectrum and to achieve synergistic effects, the 1-cycloalkylpyrazolylbenzoyl derivatives of the formula I may be mixed with a large number of representatives of other herbicidal or growth-regulating active compound groups and applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-((het)aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexeneone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Use Examples

The herbicidal activity of the 1-cycloalkylpyrazolyl benzoyl derivatives of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this is adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.5 or 0.25 kg of a.s. (active substance)/ha.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were of the following species:

| Scientific name | Common name |
| --- | --- |
| Brachiaria plantaginea | alexander grass |
| Chenopodium album | lamb's-quarters |
| Echinochloa crus-galli | barnyard grass |
| Polygonum persicaria | lady's-thumb |

At application rates of 0.5 or 0.25 kg/ha, the compound 4.6 (Table 4) showed very good post-emergence action against the abovementioned undesirable plants.

We claim:

1. A 1-cycloalkylpyrazolylbenzoyl derivative of the formula I

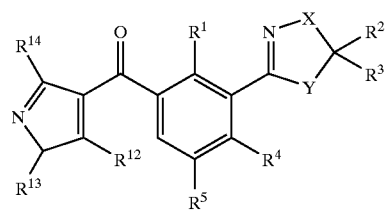

where
X is O;

Y is $CR^{10}R^{11}$;

$R^1$ is nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl or $C_1$–$C_4$-haloalkylsulfonyl;

$R^2, R^3, R^{10}, R^{11}$ are hydrogen, $C_1$–$C_4$-alkyl or $C_1$–$C_4$-haloalkyl;

or $R^3$ and $R^{11}$ together form a bond;

$R^4$ is halogen, nitro, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl or $C_1$–$C_4$-haloalkylsulfonyl;

$R^5$ is hydrogen, halogen or $C_1$–$C_4$-alkyl;

$R^{12}$ is hydroxyl, $C_1$–$C_6$-alkoxy; $C_3$–$C_6$-alkenyloxy, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is a cyclic ring system containing 3 to 14 ring atoms which
may be partially or fully halogenated; or
may carry one to three of the following groups: $C_1$–$C_4$-alkyl, $C_1$–$C_4$-alkoxy, $C_1$–$C_4$-haloalkyl or $C_1$–$C_4$-haloalkoxy; or
may be partially or fully halogenated, and carry one to three of the following groups: $C_1$–$C_4$-alkyl, $C_1$–$C_4$-alkoxy, $C_1$–$C_4$-haloalkyl or $C_1$–$C_4$-haloalkoxy;

$R^{14}$ is hydrogen or $C_1$–$C_4$-alkyl;

and its agriculturally useful salts.

2. A 1-cycloalkylpyrazolylbenzoyl derivative of the formula I as claimed in claim 1 where $R^1$ is nitro, halogen, $C_1$–$C_4$-alkyl or $C_1$–$C_4$-alkoxy;

$R^4$ is halogen, nitro, $C_1$–$C_4$-haloalkyl, $C_1$–$C_4$-alkoxy, $C_1$–$C_4$-haloalkoxy, $C_1$–$C_4$-alkylthio or $C_1$–$C_4$-alkylsulfonyl.

3. A 1-cycloalkylpyrazolylbenzoyl derivative of the formula I as claimed in claim 1, where $R^1$ is halogen, $C_1$–$C_4$-alkyl or $C_1$–$C_4$-alkoxy;

$R^4$ is $C_1$–$C_4$-alkylsulfonyl;

$R^{13}$ is $C_3$–$C_6$-cycloalkyl.

4. A 1-cycloalkylpyrazolylbenzoyl derivative of the formula I as claimed in claim 1, where $R^5$ is hydrogen.

5. A process for preparing 1-cycloalkylpyrazolylbenzoyl derivatives of the formula I where $R^{12}$=hydroxyl as claimed in claim 1, which comprises acylating a pyrazole of the formula II

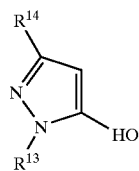

with an activated benzoic acid IIIa or a benzoic acid IIIb,

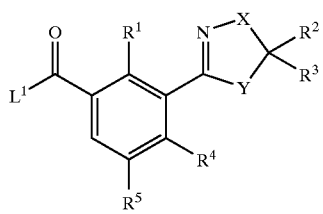

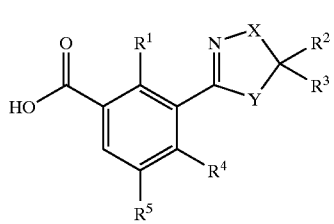

where the variables X, Y, $R^1$ to $R^5$ and $R^{13}$ to $R^{14}$ are as defined in claim 1 and $L^1$ is a nucleophilically displaceable leaving group, rearranging the acylation product in the presence or the absence of a catalyst to give the compounds of the formula I where $R^{12}$ is hydroxyl, and, optionally, to prepare 1-cycloalkylpyrazolylbenzoyl derivatives of the formula I where $R^{12}$≠ hydroxyl by reacting the product with a compound of the formula VI $$L^3-R^{12a} \qquad VI$$

where

L3 is a nucleophilically displaceable leaving group;

$R^{12a}$ is $C_1$–$C_6$-alkyl, $C_3$–$C_6$-alkenyl, $C_1$–$C_6$-alkylsulfonyl, $C_1$–$C_6$-alkylcarbonyl, phenylsulfonyl or phenylcarbonyl, where the phenyl radical of the two last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy.

6. A composition comprising a herbicidally effective amount of at least one 1-cycloalkylpyrazolylbenzoyl derivative of the formula I or an agriculturally useful salt of I as claimed in claim 1 and auxiliaries which are customarily used for formulating crop protection agents.

7. A method for controlling undesirable vegetation, which comprises allowing a herbicidally effective amount of at least one 1-cycloalkylpyrazolylbenzoyl derivative of the formula I or an agriculturally useful salt of the compound of formula I as claimed in claim 1 to act on plants, their habitat or seeds, or on their habitat and seeds.

* * * * *

UNITED STATES PATENT AND TRADEMARK OFFICE
CERTIFICATE OF CORRECTION

PATENT NO. : 6,713,436 B1
DATED : March 30, 2004
INVENTOR(S) : Neidlein et al.

It is certified that error appears in the above-identified patent and that said Letters Patent is hereby corrected as shown below:

Column 84,
Lines 58-65, change:

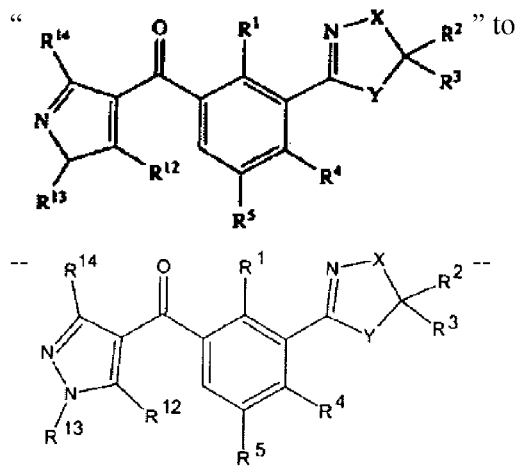

Signed and Sealed this

Nineteenth Day of April, 2005

JON W. DUDAS
*Director of the United States Patent and Trademark Office*